US012571799B2

(12) United States Patent
Nishikawa et al.

(10) Patent No.:    US 12,571,799 B2
(45) Date of Patent:        Mar. 10, 2026

(54) BIOMARKERS FOR DETERMINING THE EFFICACY OF IMMUNE CHECKPOINT INHIBITORS

(71) Applicants:ONO PHARMACEUTICAL CO., LTD., Osaka (JP); NATIONAL CANCER CENTER, Tokyo (JP)

(72) Inventors: Hiroyoshi Nishikawa, Kashiwa (JP); Yukiya Ohyama, Osaka (JP); Atsushi Honda, Osaka (JP); Atsushi Oyagi, Osaka (JP); Toru Kakinuma, Osaka (JP); Masayuki Murata, Osaka (JP)

(73) Assignees: ONO PHARMACEUTICAL CO., LTD., Osaka (JP); NATIONAL CANCER CENTER, Tokyo (JP)

( * ) Notice: Subject to any disclaimer, the term of this patent is extended or adjusted under 35 U.S.C. 154(b) by 780 days.

(21) Appl. No.: 17/632,423

(22) PCT Filed: Aug. 4, 2020

(86) PCT No.: PCT/JP2020/029882

§ 371 (c)(1),
(2) Date: Feb. 2, 2022

(87) PCT Pub. No.: WO2021/025031

PCT Pub. Date: Feb. 11, 2021

(65) Prior Publication Data

US 2022/0283167 A1      Sep. 8, 2022

(30) Foreign Application Priority Data

Aug. 5, 2019    (JP) ................................. 2019-144011
Nov. 29, 2019    (JP) ................................. 2019-216881

(51) Int. Cl.
*G01N 33/574*        (2006.01)
*C12N 5/0783*        (2010.01)

(52) U.S. Cl.
CPC ..... *G01N 33/57484* (2013.01); *C12N 5/0636* (2013.01); *G01N 2333/70521* (2013.01)

(58) Field of Classification Search
CPC .................................................. C07K 16/2818
USPC ...................................................... 424/133.1
See application file for complete search history.

(56) References Cited

PUBLICATIONS

Bendell et al (Journal of Clinical Oncology, Cancers of the Colon, Rectum, and Anus, 2018, Abstract 560).*
Tabernero et al (Journal of Clinical Oncology, Developmental Therapeutics—Immunology, 2017, 35(15 suppl) Abstract 3002).*
Hellman et al (Cancer Cell, 2018, 33: 853-861).*
Rieneke Van De Ven et al., "High PD-1 expression on regulatory and effector T-cells in lung cancer draining lymph nodes", ERJ Open Research, vol. 3, No. 2, Apr. 1, 2017, pp. 1-9.
Adil I. Daud et al., "Tumor immune profiling predicts response to anti-PD-1 therapy in human melanoma", The Journal of Clinical Investigation, vol. 126, No. 9, Sep. 1, 2016, pp. 3447-3452, (7 pages).
Adil I. Daud et al., "Supplemental Figures: Tumor immune profiling predicts response to anti-PD-1 therapy in human melanoma", Journal of Clinical Investigation, Sep. 1, 2016, 5 pages.
Yoshiko Takeuchi et al., "Roles of regulatory T cells in cancer immunity", International Immunology, vol. 28, No. 8, Aug. 22, 2016, pp. 401-409.
Communication issued on Apr. 17, 2024 by the Israel Patent Office (ILPO) for Israeli Patent Application No. 290266.
International Search Report (PCT/ISA/210) issued Nov. 2, 2020 by the International Searching Authority in counterpart International Patent Application No. PCT/JP2020/029882.
Written Opinion (PCT/ISA/237) issued Nov. 2, 2020 by the International Searching Authority in counterpart International Patent Application No. PCT/JP2020/029882.
Communication dated Aug. 29, 2024, issued by the New Zealand Intellectual Property Office in New Zealand Application No. 784813.
Communication dated Sep. 10, 2024, issued by the Japanese Patent Office in Japanese Application No. 2021-537327.
Office Action issued on Nov. 5, 2024 by the Singapore Patent Office in corresponding SG Patent Application No. 11202200995Q.

* cited by examiner

*Primary Examiner* — Sean E Aeder
(74) *Attorney, Agent, or Firm* — Sughrue Mion, PLLC

(57)        ABSTRACT

A method for identifying a patient with malignant tumor which can be expected to benefit more from an immune checkpoint inhibitor, and agent for suppressing the progression of, suppressing the recurrence of, and/or treating malignant tumor, being prescribed based thereon, comprising use of a combination of two sets of evaluation items and specific condition defined by each of combination thereof.

14 Claims, 9 Drawing Sheets

Fig. 5

BIOMARKERS FOR DETERMINING THE EFFICACY OF IMMUNE CHECKPOINT INHIBITORS

CROSS-REFERENCE TO RELATED APPLICATIONS

This is a U.S. National Stage of International Application No. PCT/JP2020/029882 filed Aug. 4, 2020, claiming priority from Japanese Patent Application No. 2019-144011 filed Aug. 5, 2019 and Japanese Patent Application No. 2019-216881 filed Nov. 29, 2019, the entire disclosures of which are incorporated by reference herein.

TECHNICAL FIELD

The present invention relates to methods for identifying patients with malignant tumors which can be expected to benefit more from immune checkpoint inhibitors (hereinafter, may be abbreviated as the "method for identifying patients of the present invention"), and agents for suppressing the progression of, suppressing the recurrence of and/or treating malignant tumors characterized by prescriptions based thereon.

BACKGROUND ART

Cancer immunotherapy is a therapy for suppressing or treating the progression of malignant tumors by strengthening the immunity against malignant tumors by acting on the immune surveillance mechanism inherent in patients with malignant tumors, unlike conventional therapies such as surgery, radiation therapy, and drug therapy using antineoplastic drugs and molecular targeting drugs. Recent researches on tumor immunity has revealed that the progression of malignant tumors is related to the immunosuppressive environment, mainly in the vicinity of tumor, and that the tumor itself utilizes a system to evade the immune surveillance mechanism. So-called immune checkpoint molecules, such as PD-1 or its ligand PD-L1, are known to be used in such evasion systems, and these inhibitors have already achieved some success in clinical practice.

However, it is still true that there are patients with malignant tumors which do not respond well to these immune checkpoint inhibitors, and there is an urgent need to identify efficacy markers capable of identifying patients which can be expected to benefit therefrom.

Although there have been reports suggesting that the ratio of the number of CD8$^+$ T cells to the number of Treg cells in peripheral blood may correlate with the prognosis of patients with malignant tumors (non-patent literature 1), there is no report of therapy capable of predicting the efficacy of an immune checkpoint inhibitor prior to administration by evaluating the combination of at least two items in the present invention, and prescribing such an immune checkpoint inhibitor to a patient identified based on the biomarker.

CITATION LIST

Non-Patent Literature

Non-Patent Literature 1: Journal of Clinical Oncology 34, no. 8 (March 2016) 833-842.

SUMMARY OF INVENTION

Technical Problem

The purpose of the present invention is to provide methods for identifying patients with malignant tumors which can be expected to benefit more from immune checkpoint inhibitors and agents for suppressing the progression of, suppressing the recurrence of and/or treating malignant tumors characterized by a prescription based thereon.

Solution to Problem

The inventors of the present invention found, as a consequence of their diligent investigation, that the specific conditions defined by the evaluation items described in the present specification and combinations of each two sets of them could be biomarkers capable of predicting the efficacy of immune checkpoint inhibitors, and completed the present invention.

That is, the present invention relates to the followings:

[1] An agent for suppressing the progression of, suppressing the recurrence of and/or treating malignant tumor, comprising an immune checkpoint inhibitory substance as an active ingredient, being administered to a patient with malignant tumor of which CD8$^+$ T cells and Foxp3$^+$ T cells in tumor tissue or blood meet (1) the condition represented by the following formula:

$$Y_1 \geq a_{1-1} \times X_1 + Y_{1-1} \qquad \text{[Formula 1]}$$

[wherein $Y_1$ represents the percentage (%) of CCR7 expressing cells among the CD8$^+$ T cells, $a_{1-1}$ represents a value of about −637, $X_1$ represents the square root of the ratio of the MFI of PD-1 expression in the CD8$^+$ T cells to the mean fluorescence intensity (hereafter, be abbreviated as MFI) of PD-1 expression in the Foxp3$^+$ T cells, and $Y_{1-1}$ represents an arbitrary value from about 784 to about 914], or (2) the two conditions represented by (i) the following formula:

$$a_{1-2} \times X_1 + Y_{1-2} \qquad \text{[Formula 2]}$$

[wherein $Y_{1-2}$ represents an arbitrary value from about 39.0 to about 50.9, $a_{1-2}$ represents a value of about −24.0, and other symbols have the same meanings as above], and (ii) the following formula:

$$Y_1 \leq a_{1-3} \times X_1 + Y_{1-3} \qquad \text{[Formula 3]}$$

[wherein $a_{1-3}$ represents a value of about 666, $Y_{1-3}$ represents an arbitrary value from about −652 to about −522, and other symbols have the same meanings as above] (hereinafter, the combination of conditions represented by the formulas of the items (1) and (2) (i) and (2) (ii) herein may be abbreviated as "Biomarker 1". Furthermore, in the present specification, an "agent for suppressing the progression of, suppressing the recurrence of and/or treating malignant tumor comprising an immune checkpoint inhibitory substance as an active ingredient" of the present invention may be collectively abbreviated as a "therapeutic agent of the present invention or the like").

[2] The agent according to the preceding item [1], wherein $Y_{1-1}$ represents an arbitrary value from about 853 to about 914.

[3] The agent according to the preceding item [1] or [2], wherein $Y_{1-2}$ represents an arbitrary value from about 39.0 to about 44.6.

[4] The agent according to any one of the preceding items [1] to [3], wherein $Y_{1-3}$ represents an arbitrary value from about −652 to about −591.

[5] The agent according to the preceding item [1], [3] or [4], wherein $Y_{1-1}$ represents an arbitrary value from about 784 to about 853.

[6] The agent according to the preceding item [1], [2], [4] or [5], wherein $Y_{1-2}$ represents an arbitrary value from about 44.6 to about 50.9.

[7] The agent according to any one of the preceding items [1] to [3], [5] and [6], wherein $Y_{1-3}$ represents an arbitrary value from about −591 to about −522.

[8] The agent according to the preceding item [1], [3], [4], [6] or [7], wherein $Y_{1-1}$ is about 853.

[9] The agent according to the preceding item [1], [2], [4], [5], [7], or [8], wherein $Y_{1-2}$ is about 44.6.

[10] The agent according to any one of the preceding items [1] to [3], [5], [6], [8] and [9], wherein $Y_{1-3}$ is about −591.

[11] An agent for suppressing the progression of, suppressing the recurrence of and/or treating malignant tumor, comprising an immune checkpoint inhibitory substance as an active ingredient, being administered to a patient with malignant tumor of which CD8$^+$ T cells and Foxp3$^+$ T cells in tumor tissue or blood meet (1) the condition represented by the following formula:

$$Y_1 \geq 637 \times X_1 + 853 \qquad \text{[Formula 4]}$$

[wherein all symbols have the same meanings as the preceding item [1]], or (2) the two conditions represented by (i) the following formula:

$$Y_1 \leq 240 \times X_1 + 44.6 \qquad \text{[Formula 5]}$$

[wherein all symbols have the same meanings as the preceding item [1]], and (ii) the following formula:

$$Y_1 \leq 666 \times X_1 - 591 \qquad \text{[Formula 6]}$$

[wherein all symbols have the same meanings as the preceding item [1]].

[12] An agent for suppressing the progression of, suppressing the recurrence of and/or treating malignant tumor, comprising an immune checkpoint inhibitory substance as an active ingredient, being administered to a patient with malignant tumor of which Treg cells (Fr.III) and CD8$^+$ T cells in tumor tissue or blood meet (1) the condition represented by the following formula:

$$Y_2 \geq a_{2-1} \times X_2 + Y_{2-1} \qquad \text{[Formula 7]}$$

[wherein $Y_2$ represents the percentage (%) of PD-1 expressing cells among the Treg cells (Fr. III), and $a_{2-1}$ represents a value of about 0.765, $X_2$ represents the percentage (%) of PD-1 expressing cells among the CD8$^+$ T cells, and $Y_{2-1}$ represents an arbitrary value from about 50.6 to about 59.2], or (2) the condition represented by the following formula:

$$Y_2 \leq a_{2-2} \times X_2 + Y_{2-2} \qquad \text{[Formula 8]}$$

[wherein $a_{2-2}$ represents a value of about 1.56, $Y_{2-2}$ represents an arbitrary value from about −44.1 to about −14.5, and other symbols have the same meanings as above] (hereinafter, the combination of conditions represented by the formulas of the items (1) and (2) herein may be abbreviated as "Biomarker 2").

[13] The agent according to the preceding item [12], wherein $Y_{2-1}$ represents an arbitrary value from about 54.1 to about 59.2.

[14] The agent according to the preceding item [12] or [13], wherein $Y_{2-2}$ represents an arbitrary value from about −44.1 to about −26.6.

[15] The agent according to the preceding item [12] or [14], wherein $Y_{2-1}$ represents an arbitrary value from about 50.6 to about 54.1.

[16] The agent according to the preceding item [12], [13] or [15], wherein $Y_{2-2}$ represents an arbitrary value from about −26.6 to about −14.5.

[17] The agent according to the preceding item [12], [14] or [16], wherein $Y_{2-1}$ is about 54.1.

[18] The agent according to the preceding item [12], [13], [15] or [17], wherein $Y_{2-2}$ is about −26.6.

[19] An agent for suppressing the progression of, suppressing the recurrence of and/or treating malignant tumor, comprising an immune checkpoint inhibitory substance as an active ingredient, being administered to a patient with malignant tumor of which Treg cells (Fr.III) and CD8$^+$ T cells in tumor tissue or blood meet (1) the condition represented by the following formula:

$$Y_2 \geq 0.765 \times X_2 + 54.1 \qquad \text{[Formula 9]}$$

[wherein all symbols have the same meanings as the preceding item [12]], or (2) the condition represented by the following formula:

$$Y_2 \leq 1.56 \times X_2 - 26.6 \qquad \text{[Formula 10]}$$

[wherein all symbols have the same meanings as the preceding item [12]].

[20] An agent for suppressing the progression of, suppressing the recurrence of and/or treating malignant tumor, comprising an immune checkpoint inhibitory substance as an active ingredient, being administered to a patient with malignant tumor of which CD8$^+$ T cells and Foxp3$^+$ T cells in tumor tissue or blood meet (1) the condition represented by (i) the following formula:

$$\mathrm{Log}_{10}(Y_3 + 1) \geq a_{3-1} \times X_3 + Y_{3-1} \qquad \text{[Formula 11]}$$

[wherein $Y_3$ represents the number of PD-1 expressing cells among the CD8$^+$ T cells, $a_{3-1}$ represents a value to about −1.59, $X_3$ represents the square root of the ratio of the MFI of PD-1 expression in the CD8$^+$ T cells to the MFI of PD-1 expression in the Foxp3$^+$ T cells, and $Y_{3-1}$ represents an arbitrary value from about 4.09 to about 4.89], or (ii) the following formula:

$$\mathrm{Log}_{10}(Y_3) \geq a_{3-4} \times X_3 + Y_{3-4} \qquad \text{[Formula 12]}$$

[wherein all symbols have the same meanings as above], or (2) the condition represented by (i) the following formula:

$$\mathrm{Log}_{10}(Y_3 + 1) \geq a_{3-2} \times X_3 + Y_{3-2} \qquad \text{[Formula 13]}$$

[wherein $a_{3-2}$ represents a value of about −9.05, $Y_{3-2}$ represents an arbitrary value from about 10.7 to about 13.3, and other symbols have the same meanings as above], or (ii) the following formula:

$$\mathrm{Log}_{10}(Y_3) \geq a_{3-2} \times X_3 + Y_{3-2} \qquad \text{[Formula 14]}$$

[wherein all symbols have the same meanings as above] (hereinafter, the combination of conditions represented by the formulas of the items (1) and (2) herein may be abbreviated as "Biomarker 3").

[21] The agent according to the preceding item [20], wherein $Y_{3-1}$ represents an arbitrary value from about 4.42 to about 4.89.

[22] The agent according to the preceding item [20] or [21], wherein $Y_{3-2}$ represents an arbitrary value from about 11.7 to about 13.3.

[23] The agent according to the preceding item [20] or [22], wherein $Y_{3-1}$ represents an arbitrary value from about 4.09 to about 4.42.

[24] The agent according to the preceding item [20], [21] or [23], wherein $Y_{3-2}$ represents an arbitrary value from about 10.7 to about 11.7.

[25] The agent according to the preceding item [20], [22] or [24], wherein $Y_{3-1}$ is about 4.42.

[26] The agent according to the preceding item [20], [21], [23] or [25], wherein $Y_{3-2}$ is about 11.7.

[27] An agent for suppressing the progression of, suppressing the recurrence of and/or treating malignant tumor, comprising an immune checkpoint inhibitory substance as an active ingredient, being administered to a patient with malignant tumor of which CD8$^+$ T cells and Foxp3$^+$ T cells in tumor tissue or blood meet (1) the condition represented by (i) the following formula:

$$\mathrm{Log}_{10}(Y_3+1)\geq -1.59\times X_3+4.42 \qquad \text{[Formula 15]}$$

[wherein all symbols have the same meanings as the preceding item [20]], or (ii) the following formula:

$$\mathrm{Log}_{10}(Y_3)\geq -1.59\times X_3+4.42 \qquad \text{[Formula 16]}$$

[wherein all symbols have the same meanings as the preceding item [20]], or (2) the condition represented by (i) the following formula:

$$\mathrm{Log}_{10}(Y_3+1)\geq -9.05\times X_3+11.7 \qquad \text{[Formula 17]}$$

[wherein all symbols have the same meanings as the preceding item [20]], or (ii) the following formula:

$$\mathrm{Log}_{10}(Y_3)\geq -9.05\times X_3+11.7 \qquad \text{[Formula 18]}$$

[wherein all symbols have the same meanings as the preceding item [20]].

[28] An agent for suppressing the progression of, suppressing the recurrence of and/or treating malignant tumor, comprising an immune checkpoint inhibitory substance as an active ingredient, being administered to a patient with malignant tumor of which CD8$^+$ T cells and Foxp3$^+$ T cells in tumor tissue or blood meet (1) the condition represented by the following formula:

$$Y_4\geq a_{4-1}\times X_4+Y_{4-1} \qquad \text{[Formula 19]}$$

[wherein $Y_4$ represents the square root of the ratio of the MFI of PD-1 expression in the CD8$^+$ T cells to the MFI of PD-1 expression in the Foxp3$^+$ T cells, $a_{4-1}$ represents a value of about −0.00273, $X_4$ represents the percentage (%) of PD-1 expressing cells among the CD8$^+$ T cells, and $Y_{4-1}$ represents an arbitrary value from about 0.905 to 1.46], or (2) the condition represented by the following formula:

$$Y_4\geq a_{4-2}\times X_4+Y_{4-2} \qquad \text{[Formula 20]}$$

[wherein $a_{4-2}$ represents a value of about −0.0294, $Y_{4-2}$ represents an arbitrary value from about 2.18 to about 3.31, and other symbols have the same meanings as above] (hereinafter, the combination of conditions represented by the formulas of the items (1) and (2) herein may be abbreviated as "Biomarker 4").

[29] The agent according to the preceding item [28], wherein $Y_{4-1}$ represents an arbitrary value from about 1.18 to about 1.46.

[30] The agent according to the preceding item [28] or [29], wherein $Y_{4-2}$ represents an arbitrary value from about 2.74 to about 3.31.

[31] The agent according to the preceding item [28] or [30], wherein $Y_{4-1}$ represents an arbitrary value from about 0.905 to about 1.18.

[32] The agent according to the preceding item [28], [29] or [31], wherein $Y_{4-2}$ represents an arbitrary value from about 2.18 to about 2.74.

[33] The agent according to the preceding item [28], [30] or [32], wherein $Y_{4-1}$ is about 1.18.

[34] The agent according to the preceding item [28], [29], [31] or [33], wherein $Y_{4-2}$ is about 2.74.

[35] An agent for suppressing the progression of, suppressing the recurrence of and/or treating malignant tumor, comprising an immune checkpoint inhibitory substance as an active ingredient, being administered to a patient with malignant tumor of which CD8$^+$ T cells and Foxp3$^+$ T cells in tumor tissue or blood meet (1) the condition represented by the following formula:

$$Y_4\geq -0.00273\times X_4+1.18 \qquad \text{[Formula 21]}$$

[wherein all symbols have the same meanings as the preceding item [28]], or (2) the condition represented by the following formula:

$$Y_4\geq -0.0294\times X_4+2.74 \qquad \text{[Formula 22]}$$

[wherein all symbols have the same meanings as the preceding item [28]].

[36] An agent for suppressing the progression of, suppressing the recurrence of and/or treating malignant tumor, comprising an immune checkpoint inhibitory substance as an active ingredient, being administered to a patient with malignant tumor of which Foxp3$^+$ T cells and CD8$^+$ T cells in tumor tissue or blood meet the condition represented by the following formula:

$$Y_5\geq a_5\times X_5+Y_5 \qquad \text{[Formula 23]}$$

[wherein $Y_5$ represents the percentage (%) of PD-1 expressing cells among the Foxp3$^+$ T cells, as represents a value of about 2.34, $X_5$ represents the percentage (%) of PD-1 expressing cells among the CD8$^+$ T cells, and $Y_{5-1}$ represents an arbitrary value from about −117 to about 131] (hereinafter, the condition represented by the above formula herein may be abbreviated as "Biomarker 5").

[37] The agent according to the preceding item [36], wherein $Y_{5-1}$ represents an arbitrary value from about −117 to about −54.4.

[38] The agent according to the preceding item [36], wherein $Y_{5-1}$ represents an arbitrary value from about −54.4 to about 131.

[39] The agent according to the preceding item [36], wherein $Y_{5-1}$ is about −54.4.

[40] An agent for suppressing the progression of, suppressing the recurrence of and/or treating malignant tumor, comprising an immune checkpoint inhibitory substance as an active ingredient, being administered to a patient with malignant tumor of which Foxp3$^+$ T cells and CD8$^+$ T cells in tumor tissue or blood meet the condition represented by the following formula:

$$Y_5\geq 2.34\times X_5-54.4 \qquad \text{[Formula 24]}$$

[wherein all symbols have the same meanings as the preceding item [36]].

[41] An agent for suppressing the progression of, suppressing the recurrence of and/or treating malignant tumor, comprising an immune checkpoint inhibitory substance as an active ingredient, being administered to a patient with malignant tumor of which Treg cells (Fr.II) and CD8$^+$ T cells in tumor tissue or blood meet (1) the condition represented by the following formula:

$$Y_6\geq a_{6-1}\times X_6+Y_{6-1} \qquad \text{[Formula 25]}$$

7

[wherein $Y_6$ represents the percentage (%) of PD-1 expressing cells among the Treg cells (Fr. II), $a_{6-1}$ represents a value of about 1.69, $X_6$ represents the percentage (%) of PD-1 expressing cells among the CD8$^+$ T cells, and $Y_{6-1}$ represents an arbitrary value from about 21.4 to about 44.1], or (2) the condition represented by the following formula:

$$Y_6 \leq a_{6-2} \times X_6 + Y_{6-2} \qquad \text{[Formula 26]}$$

[wherein $a_{6-2}$ represents a value of about 1.78, $Y_{6-2}$ represents an arbitrary value from about −80.6 to about −21.0, and other symbols have the same meanings as above] (hereinafter, the combination of conditions represented by the formulas of the items (1) and (2) herein may be abbreviated as "Biomarker 6").

[42] The agent according to the preceding item [41], wherein $Y_{6-1}$ represents an arbitrary value from about 31.8 to about 44.1.

[43] The agent according to the preceding item [41] or [42], wherein $Y_{6-2}$ represents an arbitrary value from about −80.6 to about −48.2.

[44] The agent according to the preceding item [41] or [43], wherein $Y_{6-1}$ represents an arbitrary value from about 21.4 to about 31.8.

[45] The agent according to the preceding item [41], [42] or [44], wherein $Y_{6-2}$ represents an arbitrary value from about −48.2 to about −21.0.

[46] The agent according to the preceding item [41], [43] or [45], wherein $Y_{6-1}$ is about 31.8.

[47] The agent according to the preceding item [41], [42], [44] or [46], wherein $Y_{6-2}$ is about −48.2.

[48] An agent for suppressing the progression of, suppressing the recurrence of and/or treating malignant tumor, comprising an immune checkpoint inhibitory substance as an active ingredient, being administered to a patient with malignant tumor of which Treg cells (Fr.II) and CD8$^+$ T cells in tumor tissue or blood meet (1) the condition represented by the following formula:

$$Y_6 \geq 1.69 \times X_6 + 31.8 \qquad \text{[Formula 27]}$$

[wherein all symbols have the same meanings as the preceding item [41]], or (2) the condition represented by the following formula:

$$Y_6 \leq 1.78 \times X_6 - 48.2 \qquad \text{[Formula 28]}$$

[wherein all symbols have the same meanings as the preceding item [41]].

[49] An agent for suppressing the progression of, suppressing the recurrence of and/or treating malignant tumor, comprising an immune checkpoint inhibitory substance as an active ingredient, being administered to a patient with malignant tumor of which CD4$^+$ T cells and CD8$^+$ T cells in tumor tissue or blood meet (1) the condition represented by the following formula:

$$Y_7 \leq a_{7-1} \times X_7 + Y_{7-1} \qquad \text{[Formula 29]}$$

[wherein $Y_7$ represents the percentage (%) of PD-1 expressing cells among the CD4$^+$ T cells, $a_{7-1}$ represents a value of about 0.227, $X_7$ represents the percentage (%) of PD-1 expressing cells among the CD8$^+$ T cells, and $Y_{7-1}$ represents an arbitrary value from about −13.9 to 4.03], or (2) the condition represented by the following formula:

$$Y_7 \leq a_{7-2} \times X_7 + Y_{7-2} \qquad \text{[Formula 30]}$$

[wherein $a_{7-2}$ represents a value of about 3.32, $Y_{7-2}$ represents an arbitrary value from about −199 to 58.2, and other symbols have the same meanings as above] (hereinafter, the combination of conditions represented by the formulas of the items (1) and (2) herein may be abbreviated as "Biomarker 7").

[50] The agent according to the preceding item [49], wherein $Y_{7-1}$ represents an arbitrary value from about −13.9 to about −6.56.

[51] The agent according to the preceding item [49] or [50], wherein $Y_{7-2}$ represents an arbitrary value from about −199 to about −93.5.

[52] The agent according to the preceding item [49] or [51], wherein $Y_{7-1}$ represents an arbitrary value from about −6.56 to about 4.03.

[53] The agent according to the preceding item [49], [50] or [52], wherein $Y_{7-2}$ represents an arbitrary value from about −93.5 to about 58.2.

[54] The agent according to the preceding item [49], [51] or [53], wherein $Y_{7-1}$ is about −6.56.

[55] The agent according to the preceding item [49], [50], [52] or [54], wherein $Y_{7-2}$ is about −93.5.

[56] An agent for suppressing the progression of, suppressing the recurrence of and/or treating malignant tumor, comprising an immune checkpoint inhibitory substance as an active ingredient, being administered to a patient with malignant tumor of which CD4$^+$ T cells and CD8$^+$ T cells in tumor tissue or blood meet (1) the condition represented by the following formula:

$$Y_7 \leq 0.227 \times X_7 - 6.56 \qquad \text{[Formula 31]}$$

[wherein all symbols have the same meanings as the preceding item [49]], or (2) the condition represented by the following formula:

$$Y_7 \leq 3.32 \times X_7 - 93.5 \qquad \text{[Formula 32]}$$

[wherein all symbols have the same meanings as the preceding item [49]].

[57] An agent for suppressing the progression of, suppressing the recurrence of and/or treating malignant tumor, comprising an immune checkpoint inhibitory substance as an active ingredient, being administered to a patient with malignant tumor of which CD3$^+$ cells, Treg cells (Fr.II) and CD4$^+$ T cells in tumor tissue or blood meet the condition represented by the following formula:

$$a_{8-1} \times X_8 + Y_{8-1} \leq Y_8 \leq a_{8-2} \times X_8 + Y_{8-2} \qquad \text{[Formula 33]}$$

[wherein $Y_8$ represents the square root of the ratio of the MFI of PD-1 expression in the CD3$^+$ cells to the MFI of PD-1 expression in the Treg cells (Fr. II), $a_{8-1}$ represents a value of about −0.00338, $X_8$ represents the percentage (%) of PD-1 expressing cells among the CD4$^+$ T cells, $Y_{8-1}$ represents an arbitrary value from about 0.939 to about 1.37, $a_{8-2}$ represents a value of about 0.270, and $Y_{8-2}$ represents an arbitrary value from about −6.98 to about −0.654] (hereinafter, the combination of conditions represented by the above formula herein, may be abbreviated as "Biomarker 8").

[58] The agent according to the preceding item [57], wherein $Y_{8-1}$ represents an arbitrary value from about 1.17 to about 1.37.

[59] The agent according to the preceding item [57] or [58], wherein $Y_{8-2}$ represents an arbitrary value from about −6.98 to about −4.10.

[60] The agent according to the preceding item [57] or [59], wherein $Y_{8-1}$ represents an arbitrary value from about 0.939 to about 1.17.

[61] The agent according to the preceding item [57], [58] or [60], wherein $Y_{8-2}$ represents an arbitrary value from about −4.10 to about −0.654.

[62] The agent according to the preceding item [57], [59] or [61], wherein $Y_{8-1}$ is about 1.17.

[63] The agent according to the preceding item [57], [58], [60] or [62], wherein $Y_{8-2}$ is about −4.10.

[64] An agent for suppressing the progression of, suppressing the recurrence of and/or treating malignant tumor, comprising an immune checkpoint inhibitory substance as an active ingredient, being administered to a patient with malignant tumor of which CD3$^+$ cells, Treg cells (Fr.II) and CD4$^+$ T cells in tumor tissue or blood meet the condition represented by the following formula:

$$-0.00338 \times X_8 + 1.17 \leq Y_8 \leq 0.270 \times X_8 - 4.10 \qquad \text{[Formula 34]}$$

[wherein all symbols have the same meanings as the preceding item [57]].

[65] An agent for suppressing the progression of, suppressing the recurrence of and/or treating malignant tumor, comprising an immune checkpoint inhibitory substance as an active ingredient, being administered to a patient with malignant tumor of which Foxp3$^+$ T cells and CD8$^+$ T cells in tumor tissue or blood meet the condition represented by the following formula:

$$Y_{9-1} - Y_{9-2} \leq a_9 \qquad \text{[Formula 35]}$$

[wherein, $Y_{9-1}$ represents the MFI of PD-1 expression in the Foxp3$^+$ T cells, $Y_{9-2}$ represents the MFI of PD-1 expression in the CD8$^+$ T cells, and $a_9$ represents an arbitrary value from about −716 to about 166] (hereinafter, the conditions represented by the above formula herein may be abbreviated as "Biomarker 9").

[66] The agent according to the preceding item [65], wherein $a_9$ represents an arbitrary value from about −462 to about 166.

[67] The agent according to the preceding item [65], wherein $a_9$ represents an arbitrary value from about −716 to about −3.96.

[68] The agent according to the preceding item [65], wherein $a_9$ represents an arbitrary value from about −462 to about −3.96.

[69] The agent according to the preceding item [65], wherein $a_9$ is about −208.

[70] An agent for suppressing the progression of, suppressing the recurrence of and/or treating malignant tumor, comprising an immune checkpoint inhibitory substance as an active ingredient, being administered to a patient with malignant tumor of which Treg cells (Fr.II) and CD8$^+$ T cells in tumor tissue or blood meet the condition represented by the following formula:

$$Y_{10-1} - Y_{10-2} \leq a_{10} \qquad \text{[Formula 36]}$$

[wherein $Y_{10-1}$ represents the MFI of PD-1 expression in the Treg cells (Fr. II), $Y_{10-2}$ represents the MFI of PD-1 expression in the CD8$^+$ T cells, and $a_{10}$ represents an arbitrary value from about −842 to about 133] (hereinafter, the conditions represented by the above formula herein may be abbreviated as "Biomarker 10").

[71] The agent according to the preceding item [70], wherein $a_{10}$ represents an arbitrary value from about −505 to about 133.

[72] The agent according to the preceding item [70], wherein $a_{10}$ represents an arbitrary value from about −842 to about −2.40.

[73] The agent according to the preceding item [70], wherein $a_{10}$ represents an arbitrary value from about −505 to about −2.40.

[74] The agent according to the preceding item [70], wherein $a_{10}$ is about −131.

[75] The agent according to any one of the preceding items [1] to [74], wherein the immune checkpoint inhibitory substance is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3, antibody LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

[76] The agent according to the preceding item [75], wherein the anti-PD-1 antibody is Nivolumab, Cemiplimab, Pembrolizumab, Spartalizumab, Tislelizumab, Dostarlimab, Toripalimab, Camrelizumab, Genolimzumab, Sintilimab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM 388D4, ENUM 244C8, GLS010, CS1003, BAT-1306, AK103, BI 754091, LZM009, CMAB819, Sym021, SSI-361, JY034, HX008, ISU106 or CX-188.

[77] The agent according to the preceding item [75], wherein the anti-PD-L1 antibody is Atezolizumab, Avelumab, Durvalumab, Manelimab, Pacmilimab, Envafolimab, Cosibelimab, BMS-936559, STI-1014, HLX20, SHR-1316, CS1001, MSB2311, BGB-A333, KL-A167, AK106, AK104, ZKAB001, FAZ053, CBT-502 or JS003.

[78] The agent according to the preceding item [75], wherein the anti-CTLA-4 antibody is Ipilimumab, Zalifrelimab, Nurulimab or Tremelimumab.

[79] The agent according to any one of the preceding items [1] to [78], wherein the malignant tumor is solid cancer or hematological cancer.

[80] The agent according to the preceding item [79], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinoma), nasopharyngeal cancer, uterine cancer (e.g., cervical cancer, endometrial cancer and endometrial cancer), anal cancer (e.g., anal canal cancer), colorectal cancer (e.g., high-frequency microsatellite instability (hereafter, be abbreviated as "MSI-H") and/or deficient mismatch repair (hereafter, be abbreviated as "dMMR") positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[81] The agent according to the preceding item [79], wherein the hematological cancer is one or more cancers selected from multiple myeloma, malignant lymphoma (e.g., non-Hodgkin's lymphoma (e.g., follicular lymphoma, diffuse large B-cell lymphoma, MALT lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), primary central nervous system malignant lymphoma, myelodysplastic syndrome and myeloproliferative syndrome.

[82] The agent according to the preceding item [79], wherein the malignant tumor is non-small cell lung cancer or gastric cancer.

[83] The agent according to any one of the preceding items [1] to [79], wherein the malignant tumor is pediatric cancer or primary unknown cancer.

[84] The agent according to any one of the preceding items [1] to [83], wherein the malignant tumor is on which the therapeutic effect of other anti-neoplastic drug is insufficient or not sufficient.

[85] The agent according to any one of the preceding items [1] to [84], wherein the malignant tumor is those which became worse after treatment with other anti-neoplastic drug.

[86] The agent according to any one of the preceding items [1] to [83], wherein the patient with malignant tumor has no history of treatment with other anti-neoplastic drugs.

[87] The agent according to any one of the preceding items [1] to [86], which is prescribed for postoperative or preoperative adjuvant therapy.

[88] The agent according to any one of the preceding items [1] to [87], wherein the malignant tumor is incurable or unresectable, metastatic, recurrent, refractory and/or distant metastatic.

[89] The agent according to any one of the preceding items [1] to [88], wherein the percentage of PD-L1 expressing tumor cells among tumor cells in tumor tissue (hereinafter, be abbreviated as "TPS"), or the value given by dividing the number of PD-L1 positive cells (tumor cells, lymphocytes and macrophages) by the total number of tumor cells and multiplying by 100 (hereinafter, be abbreviated as "CPS") is 50% or more, 25% or more, 10% or more, 5% or more or 1% or more.

[90] The agent according to any one of the preceding items [1] to [88], wherein the TPS or CPS is less than 50%, less than 25%, less than 10%, less than 5% or less than 1%.

[91] The agent according to any one of the preceding items [1] to [90], wherein the malignant tumor is with MSI-H and/or dMMR.

[92] The agent according to any one of the preceding items [1] to [90], wherein the malignant tumor is without MSI-H and/or dMMR or with low-frequency microsatellite instability (hereinafter be abbreviated as "MSI-L").

[93] The agent according to any one of the preceding items [80] to [92], wherein malignant melanoma or non-small cell lung cancer is BRAF V600E mutation positive.

[94] The agent according to any one of the preceding items [80] to [92], wherein malignant melanoma or non-small cell lung cancer is BRAF V600 wild-type.

[95] The agent according to any one of the preceding items [80] to [94], wherein non-small cell lung cancer is EGFR mutation positive and/or ALK fusion gene positive.

[96] The agent according to any one of the preceding items [80] to [94], wherein non-small cell lung cancer is EGFR mutation negative and/or ALK fusion gene negative.

[97] The agent according to any one of the preceding items [1] to [96], wherein the tumor mutation burden (hereinafter, be abbreviated as "TMB") of malignant tumor is high frequency (the number of mutations per 106 bases is 10 or more).

[98] The agent according to any one of the preceding items [1] to [96], wherein the TMB of malignant tumor is low frequency (the number of mutations per 106 bases is less than 10).

[99] The agent according to any one of the preceding items [1] to [98], which is further prescribed in combination with other anti-neoplastic drugs.

[100] The agent according to any one of the preceding items [84] to [86] and [99], wherein other anti-neoplastic drug is one or more selected from an alkylating agent, platinum preparation, antimetabolite (e.g., antifolate, pyridine metabolism inhibitor and purine metabolism inhibitor), ribonucleotide reductase inhibitor, nucleotide analog, topoisomerase inhibitor, microtubule polymerization inhibitor, microtubule depolymerization inhibitor, antitumor antibiotic, cytokine preparation, anti-hormonal drug, molecular targeting drug and cancer immunotherapeutic drug.

[101] The agent according to any one of the preceding items [1] to [100], wherein the patient with malignant tumor is a patient prior to administration of the agent comprising the immune checkpoint inhibitor as an active ingredient.

[102] The agent according to any one of the preceding items [1] to [101], wherein the tumor tissue is at least the tumor mass itself or tissue containing tumor-infiltrating vicinity or lymph nodes adjacent to tumor.

[1-1] A method for suppressing the progression of, suppressing the recurrence of and/or treating malignant tumor, comprising administering an effective dose of an immune checkpoint inhibitor to a patient with malignant tumor of which $CD8^+$ T cells and $Foxp3^+$ T cells in tumor tissue or blood meet (or has been confirmed to meet)

(1) the condition represented by the following formula:

$$Y_1 \geq a_{1\text{-}1} \times X_1 + Y_{1\text{-}1} \qquad \text{[Formula 37]}$$

[wherein all symbols have the same meanings as the preceding item [1]], or (2) the two conditions represented by (i) the following formula:

$$Y_1 \leq a_{1\text{-}2} \times X_1 + Y_{1\text{-}2} \qquad \text{[Formula 38]}$$

[wherein all symbols have the same meanings as the preceding item [1]], and (ii) the following formula:

$$Y_1 \leq a_{1\text{-}3} \times X_1 + Y_{1\text{-}3} \qquad \text{[Formula 39]}$$

[wherein all symbols have the same meanings as the preceding item [1]].

[1-2] A method for suppressing the progression of, suppressing the recurrence of and/or treating malignant tumor, comprising administering an effective dose of an immune checkpoint inhibitor to a patient with malignant tumor of which Treg cells (Fr.III) and $CD8^+$ T cells in tumor tissue or blood meet (or has been confirmed to meet)

(1) the condition represented by the following formula:

$$Y_2 \geq a_{2\text{-}1} \times X_2 + Y_{2\text{-}1} \qquad \text{[Formula 40]}$$

[wherein all symbols have the same meanings as the preceding item [12]], or (2) the condition represented by the following formula:

$$Y_2 \leq a_{2-2} \times X_2 + Y_{2-2} \qquad \text{[Formula 41]}$$

[wherein all symbols have the same meanings as the preceding item [12]].

[1-3] A method for suppressing the progression of, suppressing the recurrence of and/or treating malignant tumor, comprising administering an effective dose of an immune checkpoint inhibitor to a patient with malignant tumor of which $CD8^+$ T cells and $Foxp3^+$ T cells in tumor tissue or blood meet (or has been confirmed to meet)

(1) the condition represented by (i) the following formula:

$$\mathrm{Log}_{10}(Y_3+1) \geq a_{3-1} \times X_3 + Y_{3-1} \qquad \text{[Formula 42]}$$

[wherein all symbols have the same meanings as the preceding item [20]], or (ii) the following formula:

$$\mathrm{Log}_{10}(Y_3) \geq a_{3-1} \times X_3 + Y_3 \qquad \text{[Formula 43]}$$

[wherein all symbols have the same meanings as the preceding item [20]], or (2) the condition represented by (i) the following formula:

$$\mathrm{Log}_{10}(Y_3+1) \geq a_{3-2} \times X_3 + Y_{3-2} \qquad \text{[Formula 44]}$$

[wherein all symbols have the same meanings as the preceding item [20]], or (ii) the following formula:

$$\mathrm{Log}_{10}(Y_3) \geq a_{3-2} \times X_3 + Y_{3-2} \qquad \text{[Formula 45]}$$

[wherein all symbols have the same meanings as the preceding item [20]].

[1-4] A method for suppressing the progression of, suppressing the recurrence of and/or treating malignant tumor, comprising administering an effective dose of an immune checkpoint inhibitor to a patient with malignant tumor of which $CD8^+$ T cells and $Foxp3^+$ T cells in tumor tissue or blood meet (or has been confirmed to meet)

(1) the condition represented by the following formula:

$$Y_4 \geq a_{4-1} \times X_4 + Y_{4-1} \qquad \text{[Formula 46]}$$

[wherein all symbols have the same meanings as the preceding item [28]], or (2) the condition represented by the following formula:

$$Y_4 \geq a_{4-2} \times X_4 + Y_{4-2} \qquad \text{[Formula 47]}$$

[wherein all symbols have the same meanings as the preceding item [28]].

[1-5] A method for suppressing the progression of, suppressing the recurrence of and/or treating malignant tumor, comprising administering an effective dose of an immune checkpoint inhibitor to a patient with malignant tumor of which $Foxp3^+$ T cells and $CD8^+$ T cells in tumor tissue or blood meet (or has been confirmed to meet) the condition represented by the following formula:

$$Y_5 \geq a_5 \times X_5 + Y_5 \qquad \text{[Formula 48]}$$

[wherein all symbols have the same meanings as the preceding item [36]].

[1-6] A method for suppressing the progression of, suppressing the recurrence of and/or treating malignant tumor, comprising administering an effective dose of an immune checkpoint inhibitor to a patient with malignant tumor of which Treg cells (Fr.II) and $CD8^+$ T cells in tumor tissue or blood meet (or has been confirmed to meet)

(1) the condition represented by the following formula:

$$Y_6 \geq a_{6-1} \times X_6 + Y_{6-1} \qquad \text{[Formula 49]}$$

[wherein all symbols have the same meanings as the preceding item [41]], or (2) the condition represented by the following formula:

$$Y_6 \leq a_{6-2} \times X_6 + Y_{6-2} \qquad \text{[Formula 50]}$$

[wherein all symbols have the same meanings as the preceding item [41]].

[1-7] A method for suppressing the progression of, suppressing the recurrence of and/or treating malignant tumor, comprising administering an effective dose of an immune checkpoint inhibitor to a patient with malignant tumor of which $CD4^+$ T cells and $CD8^+$ T cells in tumor tissue or blood meet (or has been confirmed to meet)

(1) the condition represented by the following formula:

$$Y_7 \leq a_{7-1} \times X_7 + Y_{7-1} \qquad \text{[Formula 51]}$$

[wherein all symbols have the same meanings as the preceding item [49]], or (2) the condition represented by the following formula:

$$Y_7 \leq a_{7-2} \times X_7 + Y_{7-2} \qquad \text{[Formula 52]}$$

[wherein all symbols have the same meanings as the preceding item [49]].

[1-8] A method for suppressing the progression of, suppressing the recurrence of and/or treating malignant tumor, comprising administering an effective dose of an immune checkpoint inhibitor to a patient with malignant tumor of which $CD3^+$ cells, Treg cells (Fr.II) and $CD4^+$ T cells in tumor tissue or blood meet (or has been confirmed to meet) the condition represented by the following formula:

$$a_{8-1} \times X_8 + Y_{8-1} \leq Y_8 \leq a_{8-2} \times X_8 + Y_{8-2} \qquad \text{[Formula 53]}$$

[wherein all symbols have the same meanings as the preceding item [57]].

[1-9] A method for suppressing the progression of, suppressing the recurrence of and/or treating malignant tumor, comprising administering an effective dose of an immune checkpoint inhibitor to a patient with malignant tumor of which $Foxp3^+$ T cells and $CD8^+$ T cells in tumor tissue or blood meet (or has been confirmed to meet) the condition represented by the following formula:

$$Y_{9-1} - Y_{9-2} \leq a_9 \qquad \text{[Formula 54]}$$

[wherein all symbols have the same meanings as the preceding item [65]].

[1-10] A method for suppressing the progression of, suppressing the recurrence of and/or treating malignant tumor, comprising administering an effective dose of an immune checkpoint inhibitor to a patient with malignant tumor of which Treg cells (Fr.II) and $CD8^+$ T cells in tumor tissue or blood meet (or has been confirmed to meet) the condition represented by the following formula:

$$Y_{10-1} - Y_{10-2} \leq a_{10} \qquad \text{[Formula 55]}$$

[wherein all symbols have the same meanings as the preceding item [70]].

Note here that the respective therapeutic methods in the items [1-1] to [1-10] above may include the process of identifying the patient with malignant tumor to be treated, based on each biomarker.

[2-1] A method for identifying a patient with malignant tumor which can be expected to benefit more from an immune checkpoint inhibitor or patient with malignant tumor which is unexpected to benefit from an immune checkpoint inhibitor, by measuring (1) the number of $CD8^+$ T cells in a sample derived from tumor tissues or blood of a patient with malignant tumor and the number of CCR7 expressing cells thereamong and (2) the respective PD-1 expressions in the CD8⁺ T cells and Foxp3⁺ T cells in the same sample, by flow cytometry or immunostaining, respectively, and determining (1a) the percentage (%) of CCR7 expressing cells among the CD8⁺ T cells and (2a) the ratio of the MFI of PD-1 expression in the CD8⁺ T cells to the MFI of PD-1 expression in the Foxp3⁺ T cells, respectively, and then being based on combination of the percentage (%) and the ratio or square root of the ratio.

[2-2] The method according to the preceding item [2-1], which is for identifying a patient of which the CD8⁺ T cells and Foxp3⁺ T cells meet (1) the condition represented by the following formula:

$$Y_1 \geq a_{1\text{-}1} \times X_1 + Y_{1\text{-}1} \qquad \text{[Formula 56]}$$

[wherein all symbols have the same meanings as the preceding item [1]], or (2) the two conditions represented by (i) the following formula:

$$Y_1 \leq a_{1\text{-}2} \times X_1 + Y_{1\text{-}2} \qquad \text{[Formula 57]}$$

[wherein all symbols have the same meanings as the preceding item [1]], and (ii) the following formula:

$$Y_1 \leq a_{1\text{-}3} \times X_1 + Y_{1\text{-}3} \qquad \text{[Formula 58]}$$

[wherein all symbols have the same meanings as the preceding item [1]], as a patient with malignant tumor which can be expected to benefit more from the immune checkpoint inhibitor.

[2-3] The method according to the preceding item [2-2], wherein $Y_{1\text{-}1}$ represents an arbitrary value from about 853 to about 914.

[2-4] The method according to the preceding item [2-2] or [2-3], wherein $Y_{1\text{-}2}$ represents an arbitrary value from about 39.0 to about 44.6.

[2-5] The method according to any one of the preceding items [2-2] to [2-4], wherein $Y_{1\text{-}3}$ represents an arbitrary value from about −652 to about −591.

[2-6] The method according to the preceding item [2-2], [2-4] or [2-5], wherein $Y_{1\text{-}1}$ represents an arbitrary value from about 784 to about 853.

[2-7] The method according to the preceding item [2-2], [2-3], [2-5] or [2-6], wherein $Y_{1\text{-}2}$ represents an arbitrary value from about 44.6 to about 50.9.

[2-8] The method according to any one of the preceding items [2-2] to [2-4], [2-6] and [2-7], wherein $Y_{1\text{-}3}$ represents an arbitrary value from about −591 to about −522.

[2-9] The method according to the preceding item [2-2], [2-4], [2-5], [2-7] or [2-8], where $Y_{1\text{-}1}$ is about 853.

[2-10] The method according to the preceding item [2-2], [2-3], [2-5], [2-6], [2-8] or [2-9], wherein $Y_{1\text{-}2}$ is about 44.6.

[2-11] The method according to any one of the preceding items [2-2] to [2-4], [2-6], [2-7], [2-9] and [2-10], wherein $Y_{1\text{-}3}$ is about −591.

[2-12] A method for identifying a patient with malignant tumor which can be expected to benefit more from an immune checkpoint inhibitor or patient with malignant tumor which is unexpected to benefit from an immune checkpoint inhibitor, by measuring the respective numbers of Treg cells (Fr. III) and CD8⁺ T cells in a sample derived from tumor tissues or blood of a patient with malignant tumor and the respective numbers of PD-1 expressing cells thereamong, by flow cytometry or immunostaining, respectively, and determining the percentages (%) of PD-1 expressing cells among the Treg cells (Fr. III) and CD8⁺ T cells, respectively, and then being based on combination of the two percentages (%).

[2-13] The method according to the preceding item [2-12], which is for identifying a patient of which the Treg cells (Fr.III) and CD8⁺ T cells meet (1) the condition represented by the following formula:

$$Y_2 \geq a_{2\text{-}1} \times X_2 + Y_{2\text{-}1} \qquad \text{[Formula 59]}$$

[wherein all symbols have the same meanings as the preceding item [12]], or (2) the condition represented by the following formula:

$$Y_2 \leq a_{2\text{-}2} \times X_2 + Y_{2\text{-}2} \qquad \text{[Formula 60]}$$

[wherein all symbols have the same meanings as the preceding item [12]], as a patient with malignant tumor which can be expected to benefit more from the immune checkpoint inhibitor.

[2-14] The method according to the preceding item [2-13], wherein $Y_{2\text{-}1}$ represents an arbitrary value from about 54.1 to about 59.2.

[2-15] The method according to the preceding item [2-13] or [2-14], wherein $Y_{2\text{-}2}$ represents an arbitrary value from about −44.1 to about −26.6.

[2-16] The method according to the preceding item [2-13] or [2-15], wherein $Y_{2\text{-}1}$ represents an arbitrary value from about 50.6 to about 54.1.

[2-17] The method according to the preceding item [2-13], [2-14] or [2-16], wherein $Y_{2\text{-}2}$ represents an arbitrary value from about −26.6 to about −14.5.

[2-18] The method according to the preceding item [2-13], [2-15] or [2-17], wherein $Y_{2\text{-}1}$ is about 54.1.

[2-19] The method according to the preceding item [2-13], [2-14], [2-16] or [2-18], wherein $Y_2$-2 is about −26.6.

[2-20] A method for identifying a patient with malignant tumor which can be expected to benefit more from an immune checkpoint inhibitor or patient with malignant tumor which is unexpected to benefit from an immune checkpoint inhibitor, by measuring (1) the number of PD-1 expressing cells among CD8⁺ T cells in a sample derived from tumor tissues or blood of a patient with malignant tumor and (2) the respective PD-1 expressions in the CD8⁺ T cells and Foxp3⁺ T cells in the same sample, by flow cytometry or immunostaining, respectively, and determining the ratio of the MFI of PD-1 expression in the CD8⁺ T cells to the MFI of PD-1 expression in the Foxp3⁺ T cells, and then being based on combination of (i) the number of PD-1 expressing cells, the common logarithm of the same number of cells and the common logarithm of the value given by adding 1 to the same number of cells and (ii) the ratio or square root of the ratio.

[2-21] The method according to the preceding item [2-20], which is for identifying a patient of which the CD8⁺ T cells and Foxp3⁺ T cells meet (1) the condition represented by (i) the following formula:

$$\text{Log}_{10}(Y_3+1) \geq a_{3\text{-}1} \times X_3 + Y_{3\text{-}1} \qquad \text{[Formula 61]}$$

[wherein all symbols have the same meanings as the preceding item [20]], or (ii) the following formula:

$$\text{Log}_{10}(Y_3) \geq a_{3\text{-}4} \times X_3 + Y_{3\text{-}4} \qquad \text{[Formula 62]}$$

[wherein all symbols have the same meanings as the preceding item [20]], or (2) the condition represented by (i) the following formula:

$$\text{Log}_{10}(Y_3+1) \geq a_{3\text{-}2} \times X_3 + Y_{3\text{-}2} \qquad \text{[Formula 63]}$$

[wherein all symbols have the same meanings as the preceding item [20]], or (ii) the following formula:

$$\text{Log}_{10}(Y_3) \geq a_{3\text{-}2} \times X_3 + Y_{3\text{-}2} \qquad \text{[Formula 64]}$$

[wherein all symbols have the same meanings as the preceding item, as a patient with malignant tumor which can be expected to benefit more from the immune checkpoint inhibitor.

[2-22] The method according to the preceding item [2-21], wherein $Y_{3\text{-}1}$ represents an arbitrary value from about 4.42 to about 4.89.

[2-23] The method according to the preceding item [2-21] or [2-22], wherein $Y_{3\text{-}2}$ represents an arbitrary value from about 111.711.7 to about 13.3.

[2-24] The method according to the preceding item [2-21] or [2-23], wherein $Y_{3\text{-}1}$ represents an arbitrary value from about 4.09 to about 4.42.

[2-25] The method according to the preceding item [2-21], [2-22] or [2-24], wherein $Y_{3\text{-}2}$ represents an arbitrary value from about 10.7 to about 11.7.

[2-26] The method according to the preceding item [2-21], [2-23] or [2-25], wherein $Y_{3\text{-}1}$ is about 4.42.

[2-27] The method according to the preceding item [2-21], [2-22], [2-24] or [2-26], wherein $Y_{3\text{-}2}$ is about 11.7.

[2-28] A method for identifying a patient with malignant tumor which can be expected to benefit more from an immune checkpoint inhibitor or patient with malignant tumor which is unexpected to benefit from an immune checkpoint inhibitor, by measuring (1) the respective PD-1 expressions in CD8$^+$ T cells and Foxp3$^+$ T cells in a sample derived from tumor tissues or blood of a patient with malignant tumor and (2) the number of the CD8$^+$ T cells and the number of PD-1 expressing cells thereamong, by flow cytometry or immunostaining, respectively, and determining (1a) the ratio of the MFI of PD-1 expression in the CD8$^+$ T cells to the MFI of PD-1 expression in the Foxp3$^+$ T cells and (2a) the percentage (%) of PD-1 expressing cells among the CD8$^+$ T cells, respectively, and then being based on combination of the ratio or square root of the ratio and the percentage (%).

[2-29] The method according to the preceding item [2-28], which is for identifying a patient of which the CD8$^+$ T cells and Foxp3$^+$ T cells meet
(1) the condition represented by the following formula:

$$Y_4 \geq a_{4\text{-}1} \times X_4 + Y_{4\text{-}1} \qquad \text{[Formula 65]}$$

[wherein all symbols have the same meanings as the preceding item [28]], or
(2) the condition represented by the following formula:

$$Y_4 \geq a_{4\text{-}2} \times X_4 + Y_{4\text{-}2} \qquad \text{[Formula 66]}$$

[wherein all symbols have the same meanings as the preceding item [28]], as a patient with malignant tumor which can be expected to benefit more from the immune checkpoint inhibitor.

[2-30] The method according to the preceding item [2-29], wherein $Y_{4\text{-}1}$ represents an arbitrary value from about 1.18 to about 1.46.

[2-31] The method according to the preceding item [2-29] or [2-30], wherein $Y_{4\text{-}2}$ represents an arbitrary value from about 2.74 to about 3.31.

[2-32] The method according to the preceding item [2-29] or [2-31], wherein $Y_{4\text{-}1}$ represents an arbitrary value from about 0.905 to about 1.18.

[2-33] The method according to the preceding item [2-29], [2-30] or [2-32], wherein $Y_{4\text{-}2}$ represents an arbitrary value from about 2.18 to about 2.74.

[2-34] The method according to the preceding item [2-29], [2-31] or [2-33], wherein $Y_{4\text{-}1}$ is about 1.18.

[2-35] The method according to the preceding item [2-29], [2-30], [2-32] or [2-34], wherein $Y_4$-2 is about 2.74.

[2-36] A method for identifying a patient with malignant tumor which can be expected to benefit more from an immune checkpoint inhibitor or patient with malignant tumor which is unexpected to benefit from an immune checkpoint inhibitor, by measuring the respective numbers of Foxp3$^+$ T cells and CD8$^+$ T cells in a sample derived from tumor tissues or blood of a patient with malignant tumor and the respective numbers of PD-1 expressing cells thereamong, by flow cytometry or immunostaining, respectively, and determining the respective percentages (%) of PD-1 expressing cells among the Foxp3$^+$ T cells and CD8$^+$ T cells, and then being based on combination of the two percentages (%).

[2-37] The method according to the preceding item [2-36], which is for identifying a patient of which the Foxp3$^+$ T cells and CD8$^+$ T cells meet the condition represented by the following formula:

$$Y_5 \geq a_5 \times X_5 + Y_{5\text{-}1} \qquad \text{[Formula 67]}$$

[wherein all symbols have the same meanings as the preceding item [36]], as a patient with malignant tumor which can be expected to benefit more from the immune checkpoint inhibitor.

[2-38] The method according to the preceding item [2-37], wherein $Y_{5\text{-}1}$ represents an arbitrary value from about $-117$ to about $-54.4$.

[2-39] The method according to the preceding item [2-37], wherein $Y_{5\text{-}1}$ represents an arbitrary value from about $-54.4$ to about 131.

[2-40] The method according to the preceding item [2-37], wherein $Y_{5\text{-}1}$ is about $-54.4$.

[2-41] A method for identifying a patient with malignant tumor which can be expected to benefit more from an immune checkpoint inhibitor or patient with malignant tumor which is unexpected to benefit from an immune checkpoint inhibitor, by measuring the respective numbers of Treg cells (Fr.II) and CD8$^+$ T cells in a sample derived from tumor tissues or blood of a patient with malignant tumor and the respective numbers of PD-1 expressing cells thereamong, by flow cytometry or immunostaining, respectively, and determining the respective percentages (%) of PD-1 expressing cells among the Treg cells (Fr.II) and CD8$^+$ T cells, and then being based on combination of the two percentages (%).

[2-42] The method according to the preceding item [2-41], which is for identifying a patient of which the Treg cells (Fr.II) and CD8$^+$ T cells meet
(1) the condition represented by the following formula:

$$Y_6 \geq a_{6\text{-}1} \times X_6 + Y_{6\text{-}1} \qquad \text{[Formula 68]}$$

[wherein all symbols have the same meanings as the preceding item [41]], or
(2) the condition represented by the following formula:

$$Y_6 \leq a_{6\text{-}2} \times X_6 + Y_{6\text{-}2} \qquad \text{[Formula 69]}$$

[wherein all symbols have the same meanings as the preceding item [41]], as a patient with malignant tumor which can be expected to benefit more from the immune checkpoint inhibitor.

[2-43] The method according to the preceding item [2-42], wherein $Y_{6\text{-}1}$ represents an arbitrary value from about 31.8 to about 44.1.

[2-44] The method according to the preceding item [2-42] or [2-43], wherein $Y_{6\text{-}2}$ represents an arbitrary value from about $-80.6$ to about $-48.2$.

[2-45] The method according to the preceding item [2-42] or [2-44], wherein $Y_{6-1}$ represents an arbitrary value from about 21.4 to about 31.8.

[2-46] The method according to the preceding item [2-42], [2-43] or [2-45], wherein $Y_{6-2}$ represents an arbitrary value from about −48.2 to about −21.0.

[2-47] The method according to the preceding item [2-42], [2-44] or [2-46], wherein $Y_{6-1}$ is about 31.8.

[2-48] The method according to the preceding item [2-42], [2-43], [2-45] or [2-47], wherein $Y_6$-2 is about −48.2.

[2-49] A method for identifying a patient with malignant tumor which can be expected to benefit more from an immune checkpoint inhibitor or patient with malignant tumor which is unexpected to benefit from an immune checkpoint inhibitor, by measuring the respective numbers of CD4$^+$ T cells and CD8$^+$ T cells in a sample derived from tumor tissues or blood of a patient with malignant tumor and the respective numbers of PD-1 expressing cells thereamong, by flow cytometry or immunostaining, respectively, and determining the respective percentages (%) of PD-1 expressing cells among the CD4$^+$ T cells and CD8$^+$ T cells, and then being based on combination of the two percentages (%).

[2-50] The method according to the preceding item [2-49], which is for identifying a patient of which the CD4$^+$ T cells and CD8$^+$ T cells meet (1) the condition represented by the following formula:

$$Y_7 \leq a_{7-1} \times X_7 + Y_{7-1} \qquad \text{[Formula 70]}$$

[wherein all symbols have the same meanings as the preceding item [49]], or (2) the condition represented by the following formula:

$$Y_7 \leq a_{7-2} \times X_7 + Y_{7-2} \qquad \text{[Formula 71]}$$

[wherein all symbols have the same meanings as the preceding item [49]], as a patient with malignant tumor which can be expected to benefit more from the immune checkpoint inhibitor.

[2-51] The method according to the preceding item [2-50], wherein $Y_{7-1}$ represents an arbitrary value from about −13.9 to about −6.56.

[2-52] The method according to the preceding item [2-50] or [2-51], wherein $Y_{7-2}$ represents an arbitrary value from about −199 to about −93.5.

[2-53] The method according to the preceding item [2-50] or [2-52], wherein $Y_{7-1}$ represents an arbitrary value from about −6.56 to about 4.03.

[2-54] The method according to the preceding item [2-50], [2-51] or [2-53], wherein $Y_{7-2}$ represents an arbitrary value from about −93.5 to about 58.2.

[2-55] The method according to the preceding item [2-50], [2-52] or [2-54], wherein $Y_{7-1}$ is about −6.56.

[2-56] The method according to the preceding item [2-50], [2-51], [2-53] or [2-55], wherein $Y_{7-2}$ is about −93.5.

[2-57] A method for identifying a patient with malignant tumor which can be expected to benefit more from an immune checkpoint inhibitor or patient with malignant tumor which is unexpected to benefit from an immune checkpoint inhibitor, by measuring (1) the respective PD-1 expressions in CD3$^+$ cells and Treg cells (Fr. II) in a sample derived from tumor tissues or blood of a patient with malignant tumor and (2) the number of CD4$^+$ T cells in the same sample and the number of PD-1 expressing cells thereamong, by flow cytometry or immunostaining, respectively, and determining (1a) the ratio of the MFI of PD-1 expression in the CD3$^+$ cells to the MFI of PD-1 expression in the Treg cells (Fr. II) and (2a) the percentage (%) of PD-1 expressing cells among the CD4$^+$ T cells, respectively, and then being based on combination of the ratio or square root of the ratio and the percentage (%).

[2-58] The method according to the preceding item [2-57], which is for identifying a patient of which the CD3$^+$ cells, Foxp3$^+$ T cells and CD4$^+$ T cells meet the condition represented by the following formula:

$$a_{8-1} \times X_8 + Y_{8-1} \leq Y_8 \leq a_{8-2} \times X_8 + Y_{8-2} \qquad \text{[Formula 72]}$$

[wherein all symbols have the same meanings as the preceding item [57]], as a patient with malignant tumor which can be expected to benefit more from the immune checkpoint inhibitor.

[2-59] The method according to the preceding item [2-58], wherein $Y_{8-1}$ represents an arbitrary value from about 1.17 to about 1.37.

[2-60] The method according to the preceding item [2-58] or [2-59], wherein $Y_{8-2}$ represents an arbitrary value from about −6.98 to about −4.10.

[2-61] The method according to the preceding item [2-58] or [2-60], wherein $Y_{8-1}$ represents an arbitrary value from about 0.939 to about 1.17.

[2-62] The method according to the preceding item [2-58], [2-59] or [2-61], wherein $Y_{8-2}$ represents an arbitrary value from about −4.10 to about −0.654.

[2-63] The method according to the preceding item [2-59], [2-61] or [2-62], wherein $Y_{8-1}$ is about 1.17.

[2-64] The method according to the preceding item [2-58], [2-59], [2-61] or [2-63], wherein $Y_{8-2}$ is about −4.10.

[2-65] A method for identifying a patient with malignant tumor which can be expected to benefit more from an immune checkpoint inhibitor or patient with malignant tumor which is unexpected to benefit from an immune checkpoint inhibitor, by measuring the respective PD-1 expressions in Foxp3$^+$ T cells and CD8$^+$ T cells in a sample derived from tumor tissues or blood of a patient with malignant tumor, by flow cytometry or immunostaining, respectively, and determining the value given by subtracting the MFI of PD-1 expression in the CD8$^+$ T cells from the MFI of PD-1 expression in the Foxp3$^+$ T cells, and then being based on the same value.

[2-66] The method according to the preceding item [2-65], which is for identifying a patient of which the Foxp3$^+$ T cells and CD8$^+$ T cells meet the condition represented by the following formula:

$$Y_{9-1} - Y_{9-2} \leq a_9 \qquad \text{[Formula 73]}$$

[wherein all symbols have the same meanings as the preceding item [65]], as a patient with malignant tumor which can be expected to benefit more from the immune checkpoint inhibitor.

[2-67] The method according to the preceding item [2-66], wherein $a_9$ represents an arbitrary value from about −462 to about 166.

[2-68] The method according to the preceding item [2-66], wherein $a_9$ represents an arbitrary value from about −716 to about −3.96.

[2-69] The method according to the preceding item [2-66], wherein $a_9$ represents an arbitrary value from about −462 to about −3.96.

[2-70] The method according to the preceding item [2-66], wherein $a_9$ is about −208.

[2-71] A method for identifying a patient with malignant tumor which can be expected to benefit more from an immune checkpoint inhibitor or patient with malignant tumor which is unexpected to benefit from an immune checkpoint inhibitor, by measuring the respective PD-1 expressions in Treg cells (Fr.II) and CD8$^+$ T cells in a sample derived from tumor tissues or blood of a patient with malignant tumor, by flow cytometry or immunostaining, respectively, and determining the value given by subtracting the MFI of PD-1 expression in the CD8$^+$ T cells from the MFI of PD-1 expression in the Treg cells (Fr.II), and then being based on the same value.

[2-72] The method according to the preceding item [2-71], which is for identifying a patient of which the Treg cells (Fr.II) and CD8$^+$ T cells meet the condition represented by the following formula:

$$Y_{10-1}-Y_{10-2} \leq a_{10} \qquad \text{[Formula 74]}$$

[wherein all symbols have the same meanings as the preceding item [70]], as a patient with malignant tumor which can be expected to benefit more from the immune checkpoint inhibitor.

[2-73] The method according to the preceding item [2-72], wherein $a_{10}$ represents an arbitrary value from about −505 to about 133.

[2-74] The method according to the preceding item [2-72], wherein $a_{10}$ represents an arbitrary value from about −842 to about −2.40.

[2-75] The method according to the preceding item [2-72], wherein $a_{10}$ represents an arbitrary value from about −505 to about −2.40.

[2-76] The method according to the preceding item [2-72], wherein $a_{10}$ is about −131.

[2-77] The method according to any one of the preceding items [2-1] to [2-76], wherein the immune checkpoint inhibitor is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

[2-78] The method according to the preceding item [2-77], wherein the anti-PD-1 antibody is Nivolumab, Cemiplimab, Pembrolizumab, Spartalizumab, Tislelizumab, Dostarlimab, Toripalimab, Camrelizumab, Genolimzumab, Sintilimab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM 388D4, ENUM 244C8, GLS010, CS1003, BAT-1306, AK103, BI 754091, LZM009, CMAB819, Sym021, SSI-361, JY034, HX008, ISU106 or CX-188.

[2-79] The method according to the preceding item [2-77], wherein the anti-PD-L1 antibody is Atezolizumab, Avelumab, Durvalumab, Manelimab, Pacmilimab, Envafolimab, Cosibelimab, BMS-936559, STI-1014, HLX20, SHR-1316, CS1001, MSB2311, BGB-A333, KL-A167, AK106, AK104, ZKAB001, FAZ053, CBT-502 or JS003.

[2-80] The method according to the preceding item [2-77], wherein the anti-CTLA-4 antibody is Ipilimumab, Zalifrelimab, Nurulimab or Tremelimumab.

[2-81] The method according to any one of the preceding items [2-1] to [2-80], wherein the malignant tumor is solid cancer or hematological cancer.

[2-82] The method according to the preceding item [2-81], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, naslapharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinoma), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[2-83] The method according to the preceding item [2-81], wherein the hematological cancer is one or more cancers selected from multiple myeloma, malignant lymphoma (e.g., non-Hodgkin's lymphoma (e.g., follicular lymphoma, diffuse large B-cell lymphoma, MALT lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), primary central nervous system malignant lymphoma, myelodysplastic syndrome and myeloproliferative syndrome.

[2-84] The method according to the preceding item [2-81], wherein the malignant tumor is non-small cell lung cancer or gastric cancer.

[2-85] The method according to any one of the preceding items [2-1] to [2-81], wherein the malignant tumor is pediatric cancer or primary unknown cancer.

[2-86] The method according to any one of the preceding items [2-1] to [2-85], wherein the malignant tumor is on which the therapeutic effect of other anti-neoplastic drug is insufficient or not sufficient.

[2-87] The method according to any one of the preceding items [2-1] to [2-86], wherein the malignant tumor is those which became worse after treatment with other anti-neoplastic drug.

[2-88] The method according to any one of the preceding items [2-1] to [2-85], wherein the patient with malignant tumor has no history of treatment with other anti-neoplastic drugs.

[2-89] The method according to any one of the preceding items [2-1] to [2-88], which is prescribed for postoperative or preoperative adjuvant therapy.

[2-90] The method according to any one of the preceding items [2-1] to [2-89], wherein the malignant tumor is incurable or unresectable, metastatic, recurrent, refractory and/or distant metastatic.

[2-91] The method according to any one of the preceding items [2-1] to [2-90], wherein the TPS or CPS is 50% or more, 25% or more, 5% or more or 1% or more.

[2-92] The method according to any one of the preceding items [2-1] to [2-90], wherein the TPS or CPS is less than 50%, less than 25%, less than 5% or less than 1%.

[2-93] The method according to any one of the preceding items [2-1] to [2-92], wherein the malignant tumor is with MSI-H and/or dMMR.

[2-94] The method according to any one of the preceding items [2-1] to [2-92], wherein the malignant tumor is without MSI-H and/or dMMR or with MSI-L.

[2-95] The method according to any one of the preceding items [2-82] to [2-94], wherein malignant melanoma or non-small cell lung cancer is BRAF V600E mutation positive.

[2-96] The method according to any one of the preceding items [2-82] to [2-94], wherein malignant melanoma or non-small cell lung cancer is BRAF V600 wild-type.

[2-97] The method according to any one of the preceding items [2-82] to [2-96], wherein non-small cell lung cancer is EGFR mutation positive and/or ALK fusion gene positive.

[2-98] The method according to any one of the preceding items [2-82] to [2-96], wherein non-small cell lung cancer is EGFR mutation negative and/or ALK fusion gene negative.

[2-99] The method according to any one of the preceding items [2-1] to [2-98], wherein the TMB of malignant tumor is high frequency.

[2-100] The method according to any one of the preceding items [2-1] to [2-98], wherein the TMB of malignant tumor is low frequency.

[2-101] The method according to any one of the preceding items [2-1] to [2-100], wherein the patient with malignant tumor is a patient prior to administration of the immune checkpoint inhibitor.

[2-102] The method according to any one of the preceding items [2-1] to [2-101], wherein the tumor tissue is at least the tumor mass itself or tissue containing tumor-infiltrating vicinity or lymph nodes adjacent to tumor.

[3-0] Use of any one, preferably combination of any two of evaluation items selected from (1) the percentage (%) of CCR7 expressing cells among CD8$^+$ T cells in tumor tissue or blood from a patient with malignant tumor, (2) the number of PD-1 expressing cells among the CD8$^+$ T cells, the common logarithm of the same number of cells, or the common logarithm of the value given by adding 1 to the same number of cells, (3) the ratio of the MFI of PD-1 expression in the CD8$^+$ T cells to the MFI of PD-1 expression in the same origin Foxp3$^+$ T cells, or the square root of the ratio, (4) the percentage (%) of PD-1 expressing cells among the same origin Treg cells (Fr.III), (5) the percentage (%) of PD-1 expressing cells among the Foxp3$^+$ T cells, (6) the percentage (%) of PD-1 expressing cells among the same origin Treg cells (Fr. II), (7) the percentage (%) of PD-1 expressing cells among the same origin CD4$^+$ T cells, (8) the percentage (%) of PD-1 expressing cells among the CD8$^+$ T cells, (9) the ratio of the MFI of PD-1 expression in the same origin CD3$^+$ cells to the MFI of PD-1 expression in the Treg cells (Fr. II), or the square root of the ratio,

(10) the percentage (%) of PD-1 expressing cells among the CD4$^+$ T cells,

(11) the value given by subtracting the MFI of PD-1 expression in the CD8$^+$ T cells from the MFI of PD-1 expression in the Foxp3$^+$ T cells, and

(12) the value given by subtracting the MFI of PD-1 expression in the CD8$^+$ T cells from the MFI of PD-1 expression in the Treg cells (Fr. II), as a biomarker for predicting the efficacy of suppressing the progression of, suppressing the recurrence of and/or treating malignant tumor with an immune checkpoint inhibitor.

[3-1] The use of combination of (1) (i) the percentage (%) of CCR7 expressing cells among CD8$^+$ T cells in tumor tissue or blood from the patient with malignant tumor, or (ii) the number of PD-1 expressing cells among the CD8$^+$ T cells, the common logarithm of the same number of cells, or the common logarithm of the value given by adding 1 to the same number of cells, and (2) the ratio of the MFI of PD-1 expression in the CD8$^+$ T cells to the MFI of PD-1 expression in the same origin Foxp3$^+$ T cells, or the square root of the ratio, as the biomarker according to the preceding item [3-0].

[3-2] The use of combination of (1) any one selected from (i) the percentage (%) of PD-1 expressing cells among Treg cells (Fr.III) in tumor tissue or blood from the patient with malignant tumor, (ii) the ratio of the MFI of PD-1 expression in the same origin CD8$^+$ T cells to the MFI of PD-1 expression in the same origin Foxp3$^+$ T cells, or the square root of the ratio, (iii) the percentage (%) of PD-1 expressing cells among the Foxp3$^+$ T cells, (iv) the percentage (%) of PD-1 expressing cells among the same origin Treg cells (Fr. II), and (v) the percentage (%) of PD-1 expressing cells among the same origin CD4$^+$ T cells, and (2) the percentage (%) of PD-1 expressing cells among the CD8$^+$ T cells, as the biomarker according to the preceding item [3-0].

[3-3] The use of combination of (1) the percentage (%) of CCR7 expressing cells among the CD8$^+$ T cells, and (2) the ratio of the MFI of PD-1 expression in the CD8$^+$ T cells to the MFI of PD-1 expression in the Foxp3$^+$ T cells, or the square root of the ratio, as the biomarker according to the preceding item [3-1].

[3-4] The use of combination of the respective percentages (%) of PD-1 expressing cells among the Treg cells (Fr.III) and CD8$^+$ T cells, as the biomarker according to the preceding item [3-2].

[3-5] The use of combination of (1) the number of PD-1 expressing cells among the CD8$^+$ T cells, the common logarithm of the same number of cells, or the common logarithm of the value given by adding 1 to the same number of cells, and (2) the ratio of the MFI of PD-1 expression in the CD8$^+$ T cells to the MFI of PD-1 expression in the Foxp3$^+$ T cells, or the square root of the ratio, as the biomarker according to the preceding item [3-1].

[3-6] The use of combination of (1) the ratio of the MFI of PD-1 expression in the CD8$^+$ T cells to the MFI of PD-1 expression in the Foxp3$^+$ T cells, or the square root of the ratio, and (2) the percentage (%) of PD-1 expressing cells among the CD8$^+$ T cells, as the biomarker according to the preceding item [3-2].

[3-7] The use of combination of the respective percentages (%) of PD-1 expressing cells among the Foxp3$^+$ T cells and CD8$^+$ T cells, as the biomarker according to the preceding item [3-2].

[3-8] The use of combination of the respective percentages (%) of PD-1 expressing cells among the Treg cells (Fr. II) and CD8$^+$ T cells, as the biomarker according to the preceding item [3-2].

[3-9] The use of combination of the respective percentages (%) of PD-1 expressing cells among the CD4$^+$ T cells and CD8$^+$ T cells, as the biomarker according to the preceding item [3-2].

[3-10] The use of combination of (1) the ratio of the MFI of PD-1 expression in the CD3$^+$ cells to the MFI of PD-1 expression in the Treg cells (Fr. II), or the square root of the ratio, and (2) the percentage (%) of PD-1 expressing cells among the CD4$^+$ T cells, as the biomarker according to the preceding item [3-0].

[3-11] Use of the value given by subtracting the MFI of PD-1 expression in the same origin CD8$^+$ T cells from the MFI of PD-1 expression in Foxp3$^+$ T cells in tumor tissue or blood from a patient with malignant tumor, as a biomarker for predicting the efficacy of suppressing the progression of, suppressing the recurrence of and/or treating malignant tumor with an immune checkpoint inhibitor.

[3-12] Use of the value given by subtracting the MFI of PD-1 expression in the same origin CD8$^+$ T cells from the MFI of PD-1 expression in Treg cells (Fr. II) in tumor tissue or blood from a patient with malignant tumor, as a biomarker for predicting the efficacy of suppressing the progression of, suppressing the recurrence of and/or treating malignant tumor with an immune checkpoint inhibitor.

[3-13] The use according to any one of the preceding items [3-0] to [3-12], wherein the immune checkpoint inhibitor is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

[3-14] The use according to the preceding item [3-13], wherein the anti-PD-1 antibody is Nivolumab, Cemiplimab, Pembrolizumab, Spartalizumab, Tislelizumab, Dostarlimab, Toripalimab, Camrelizumab, Genolimzumab, Sintilimab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM 388D4, ENUM 244C8, GLS010, CS1003, BAT-1306, AK103, BI 754091, LZM009, CMAB819, Sym021, SSI-361, JY034, HX008, ISU106 or CX-188.

[3-15] The use according to the preceding item [3-13], wherein the anti-PD-L1 antibody is Atezolizumab, Avelumab, Durvalumab, Manelimab, Pacmilimab, Envafolimab, Cosibelimab, BMS-936559, STI-1014, HLX20, SHR-1316, CS1001, MSB2311, BGB-A333, KL-A167, AK106, AK104, ZKAB001, FAZ053, CBT-502 or JS003.

[3-16] The use according to the preceding item [3-13], wherein the anti-CTLA-4 antibody is Ipilimumab, Zalifrelimab, Nurulimab or Tremelimumab.

[3-17] The use according to any one of the preceding items [3-0] to [3-16], wherein the malignant tumor is solid cancer or hematological cancer.

[3-18] The use according to the preceding item [3-17], wherein the solid cancer is one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, naopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinoma), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

[3-19] The use according to the preceding item [3-17], wherein the hematological cancer is one or more cancers selected from multiple myeloma, malignant lymphoma (e.g., non-Hodgkin's lymphoma (e.g., follicular lymphoma, diffuse large B-cell lymphoma, MALT lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia, T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), primary central nervous system malignant lymphoma, myelodysplastic syndrome and myeloproliferative syndrome.

[3-20] The use according to any one of the preceding items [3-0] to [3-16], wherein the malignant tumor is pediatric cancer or primary unknown cancer.

[3-21] The use according to any one of the preceding items [3-0] to [3-20], wherein the patient with malignant tumor is a patient prior to administration of the immune checkpoint inhibitor.

[3-22] The use according to any one of the preceding items [3-0] to [3-21], wherein the tumor tissue is at least the tumor mass itself or tissue containing tumor-infiltrating vicinity or lymph nodes adjacent to tumor.

Advantage Effects of Invention

By measuring the biomarkers of the present invention, it is possible to identify the patient with malignant tumor which can be expected to benefit more from the immune checkpoint inhibitor.

Figure 2:
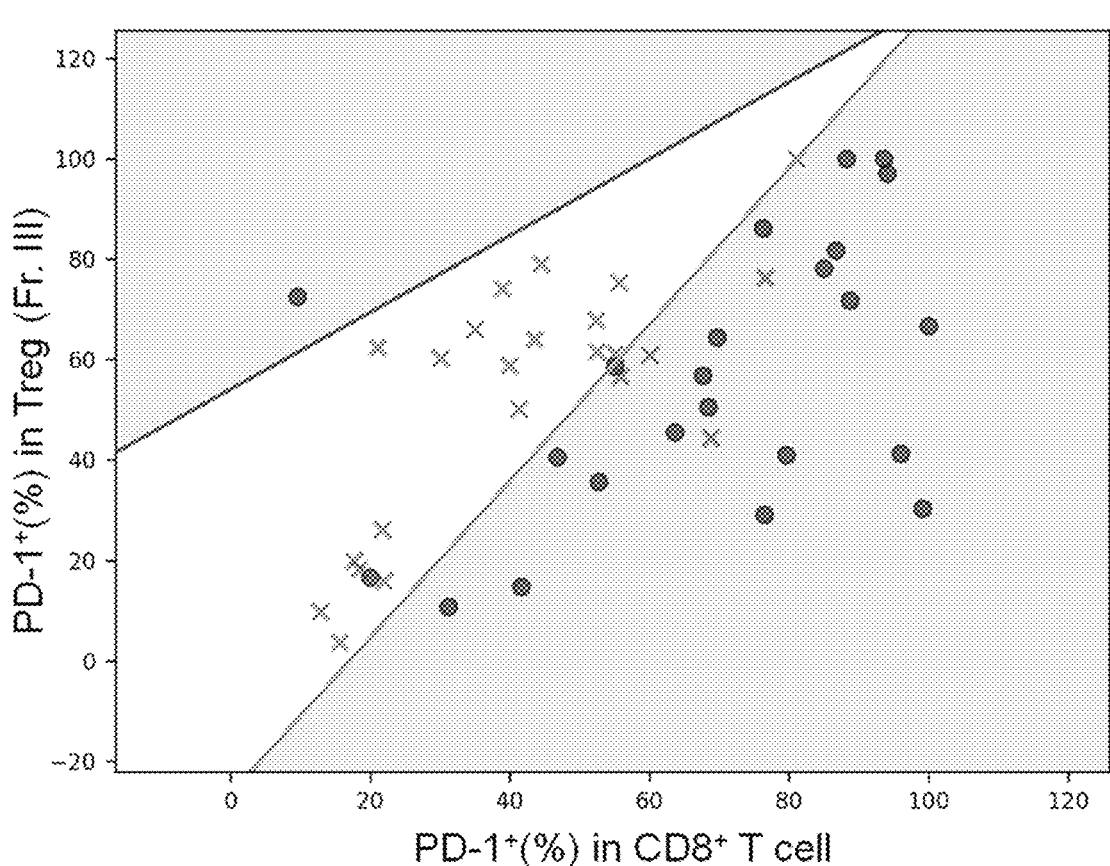

FIG. 2 It shows a result in which the Responder group (black circles in the figure) and Non-responder group (x marks in the figure) among patients with gastric cancer (29 cases) and patients with non-small cell lung cancer (17 cases) treated with Nivolumab were plotted on a graph with the percentage (%) of PD-1 expressing cells among Treg cells (Fr. III) in tumor tissue of each of the patient before administration of Nivolumab on the vertical axis, and the percentage (%) of PD-1 expressing cells among CD8+ T cells on the horizontal axis. The two solid lines in the figure represent the classification lines derived by machine learning as described above, and the shaded areas on the upper left and lower right sides of the figure indicate that a patient with tumor plotted therein can be expected to benefit from Nivolumab.

Figure 3:
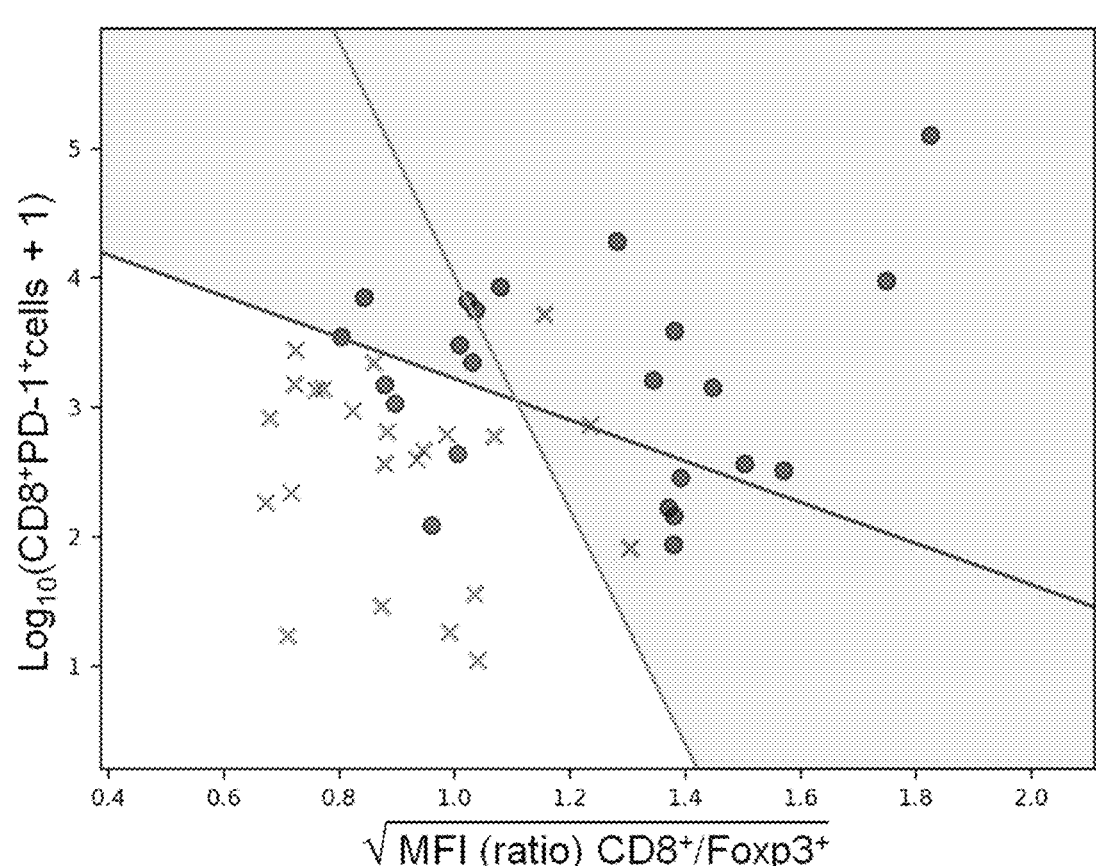

FIG. 3 It shows a result in which the Responder group (black circles in the figure) and Non-responder group (x marks in the figure) among patients with gastric cancer (29 cases) and patients with non-small cell lung cancer (17 cases) treated with Nivolumab were plotted on a graph with the common logarithm of the value given by adding 1 to the number of PD-1 expressing cells among CD8+ T cells in tumor tissue of each of the patient before administration of Nivolumab on the vertical axis, and the square root of the ratio of the MFI of PD-1 expression in the CD8+ T cells to the MFI of PD-1 expression in the same origin Foxp3+ T cells on the horizontal axis. The two solid lines in the figure represent the classification lines derived by machine learning as described above, and the shaded area, except for the lower left side of the figure, indicates that a patient with tumor plotted therein can be expected to benefit from Nivolumab.

Figure 4:
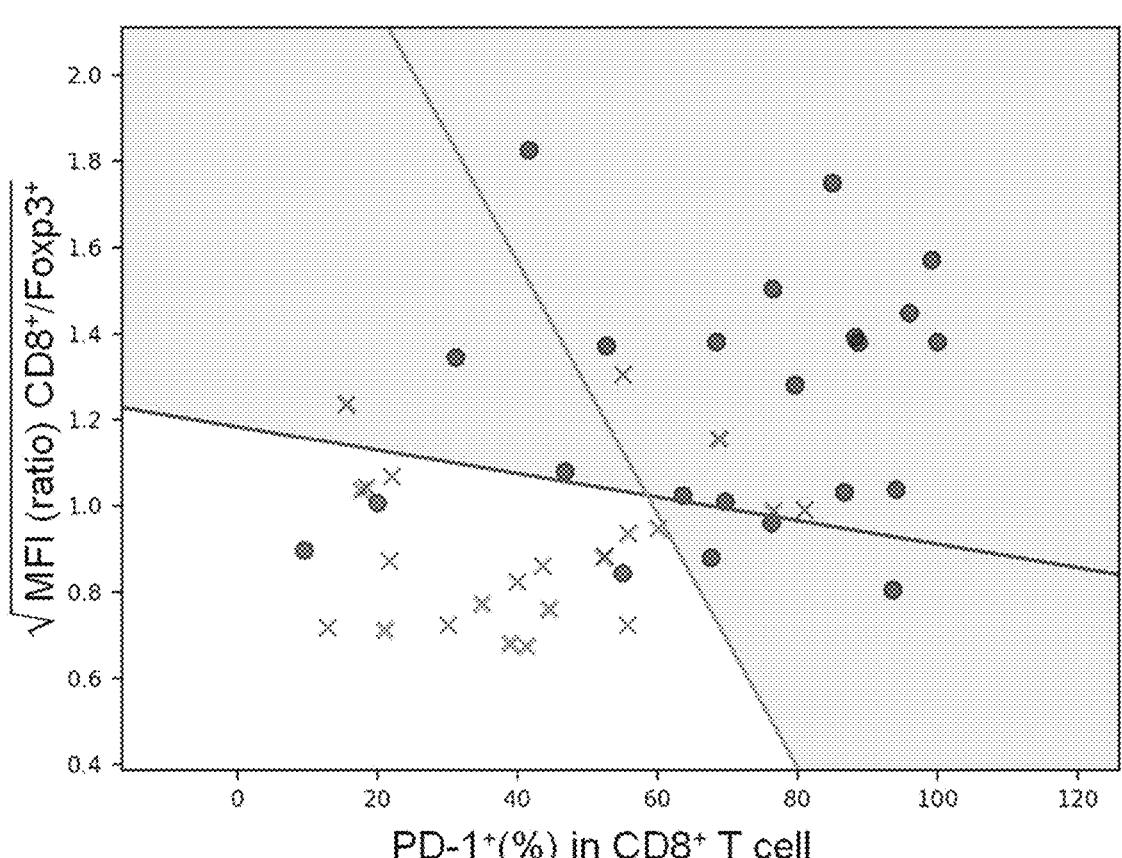

FIG. 4 It shows a result in which the Responder group (black circles in the figure) and Non-responder group (x marks in the figure) among patients with gastric cancer (29 cases) and patients with non-small cell lung cancer (17 cases) treated with Nivolumab were plotted on a graph with the square root of the ratio of the MFI of PD-1 expression in the same origin CD8+ T cells to the MFI of PD-1 expression in Foxp3+ T cells in tumor tissue of each of the patient before administration of Nivolumab on the vertical axis, and the percentage (%) of PD-1 expressing cells among CD8+ T cells on the horizontal axis. The two solid lines in the figure represent the classification lines derived by machine learning as described above, and the shaded areas, except for the lower left side of the figure, indicate that a patient with tumor plotted therein can be expected to benefit from Nivolumab.

Figure 5:
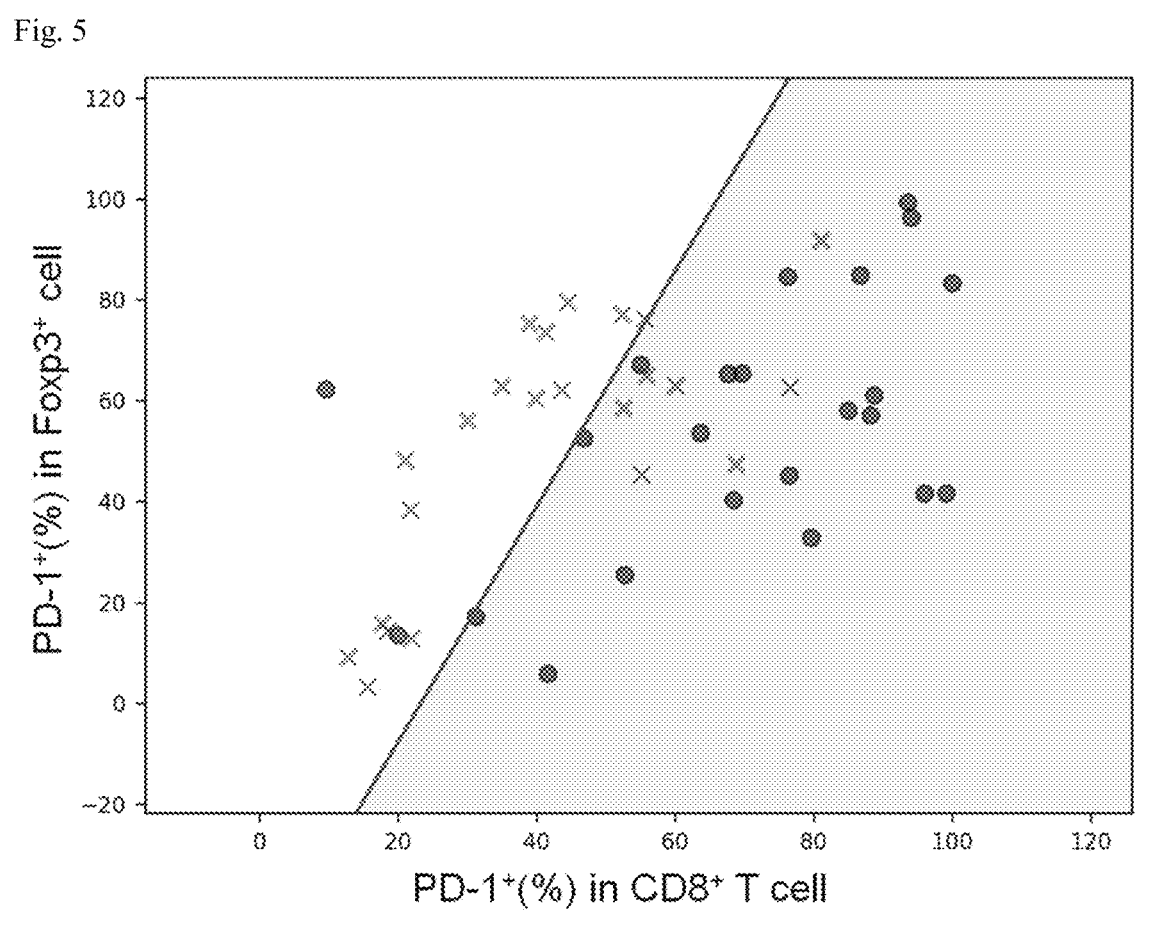

FIG. 5 It shows a result in which the Responder group (black circles in the figure) and Non-responder group (x marks in the figure) among patients with gastric cancer (29 cases) and patients with non-small cell lung cancer (17 cases) treated with Nivolumab were plotted on a graph with the percentage (%) of PD-1 expressing cells among the Foxp3+ T cells in tumor tissue of each of the patient before administration of Nivolumab on the vertical axis, and the percentage (%) of PD-1 expressing cells among the same origin CD8+ T cells on the horizontal axis. The solid line in the figure represents the classification line derived by machine learning as described above, and the shaded area on the right side of the figure indicates that a patient with tumor plotted therein can be expected to benefit from Nivolumab.

Figure 6:
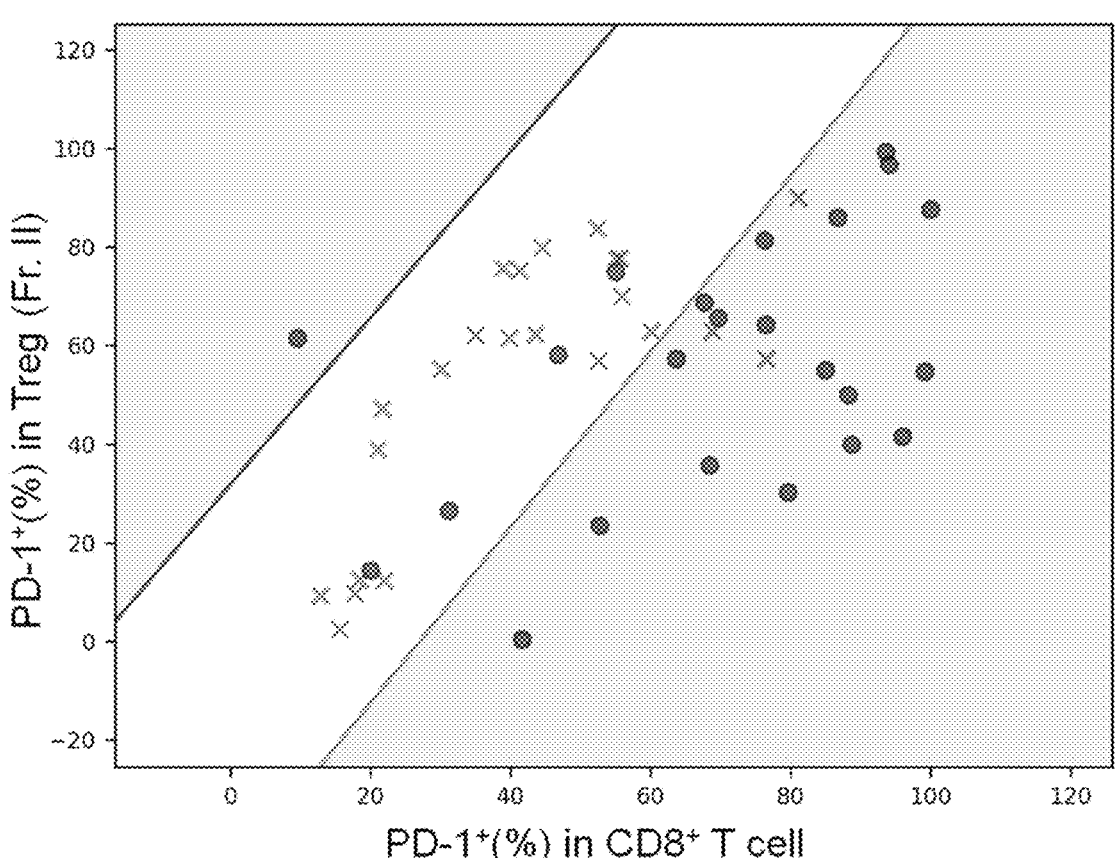

FIG. 6 It shows a result in which the Responder group (black circles in the figure) and Non-responder group (x marks in the figure) among patients with gastric cancer (29 cases) and patients with non-small cell lung cancer (17 cases) treated with Nivolumab were plotted on a graph with the percentage (%) of PD-1 expressing cells among Treg cells (Fr.II) in tumor tissue of each of the patient before administration of Nivolumab on the vertical axis, and the percentage (%) of PD-1 expressing cells among the same origin CD8+ T cells on the horizontal axis. The two solid lines in the figure represent the classification lines derived by machine learning as described above, and the shadow areas on the upper left and lower right sides of the figure indicate that a patient with tumor plotted therein can be expected to benefit from Nivolumab.

Figure 7:
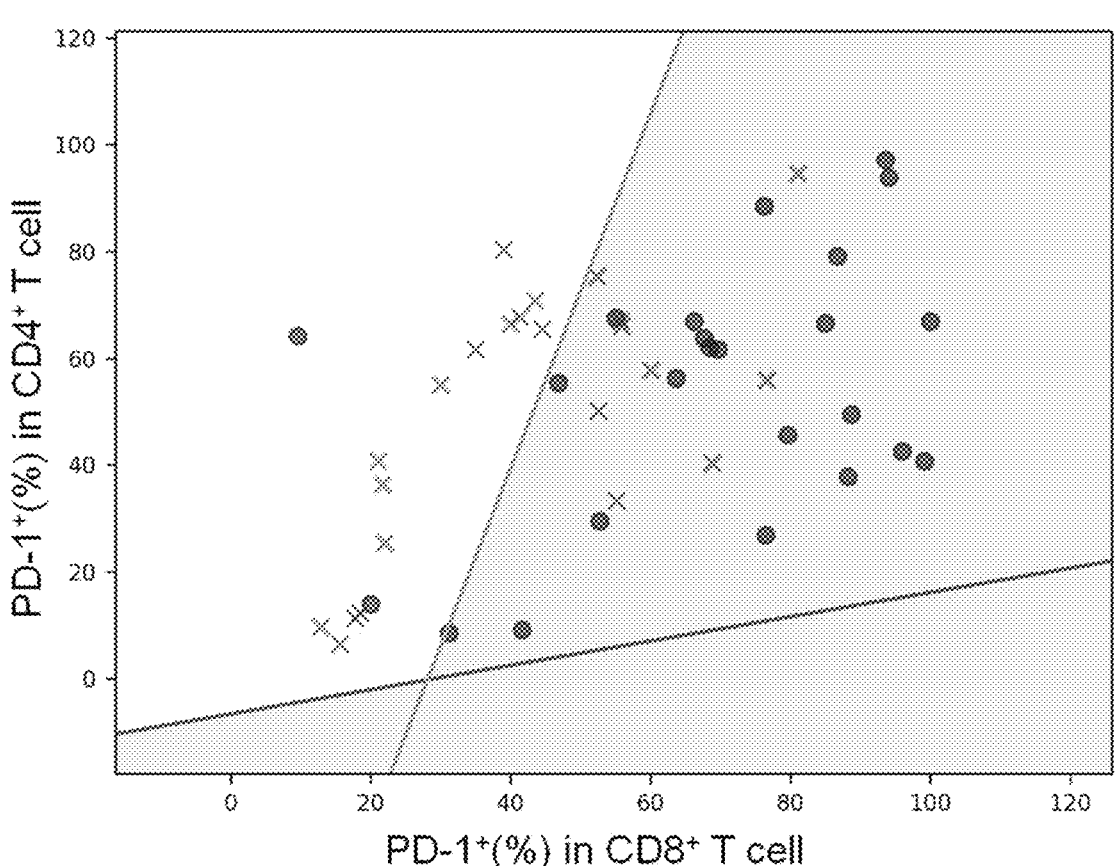

FIG. 7 It shows a result in which the Responder group (black circles in the figure) and Non-responder group (x marks in the figure) among patients with gastric cancer (29 cases) and patients with non-small cell lung cancer (18 cases) treated with Nivolumab were plotted on a graph with the percentage (%) of PD-1 expressing cells among CD4+ T cells in tumor tissue of each of the patient before administration of Nivolumab on the vertical axis, and the percentage (%) of PD-1 expressing cells among the same origin CD8+ T cells on the horizontal axis. The two solid lines in the figure represent the classification lines derived by machine learning as described above, and the shadow areas, except for the upper left side of the figure, indicate that a patient with tumor plotted therein can be expected to benefit from Nivolumab.

Figure 8:
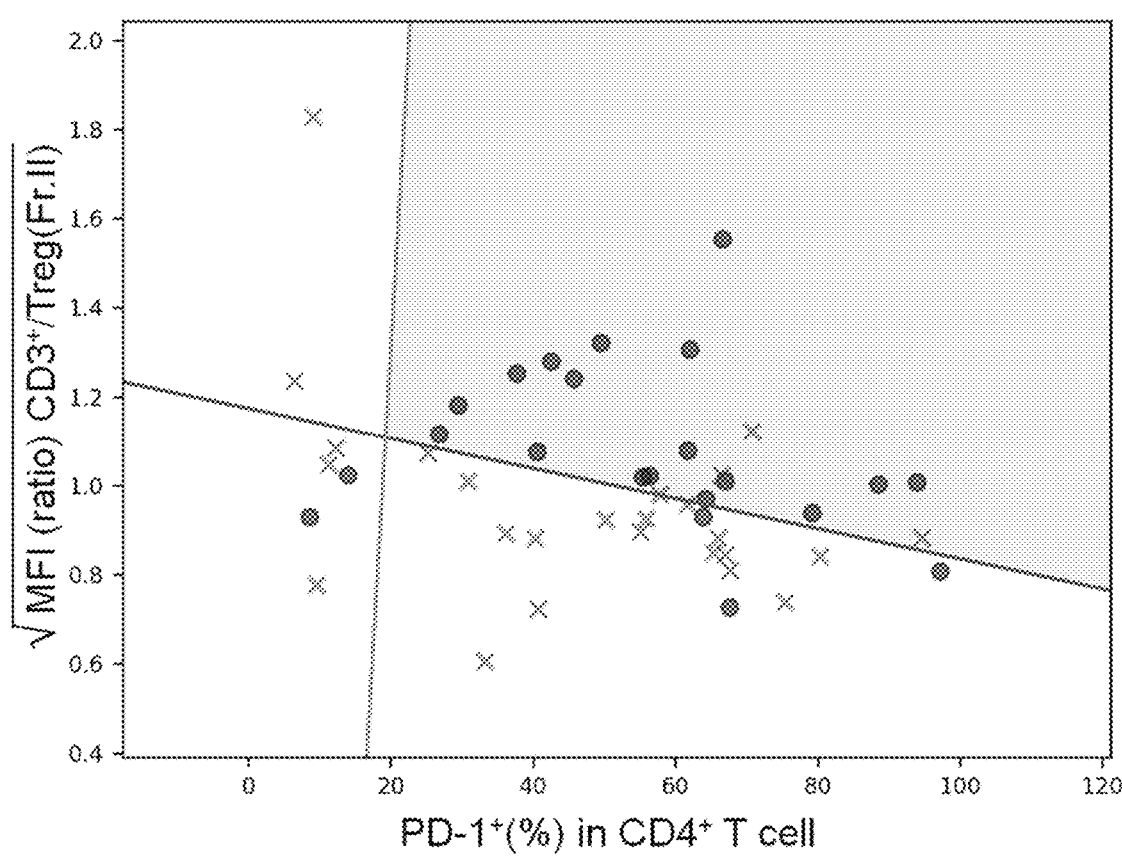

FIG. 8 It shows a result in which the Responder group (black circles in the figure) and Non-responder group (x marks in the figure) among patients with gastric cancer (29 cases) and patients with non-small cell lung cancer (18 cases) treated with Nivolumab were plotted on a graph with the square root of the ratio of the MFI of PD-1 expression in the same origin CD3+ cells to the MFI of PD-1 expression in Treg cells (Fr.II) in tumor tissue of each of the patient before administration of Nivolumab on the vertical axis, and the percentage (%) of PD-1 expressing cells among the same origin CD4+ T cells on the horizontal axis. The two solid lines in the figure represent the classification lines derived by machine learning as described above, and the shadow area on the upper left side of the figure indicate that a patient with tumor plotted therein can be expected to benefit from Nivolumab.

Figure 9:
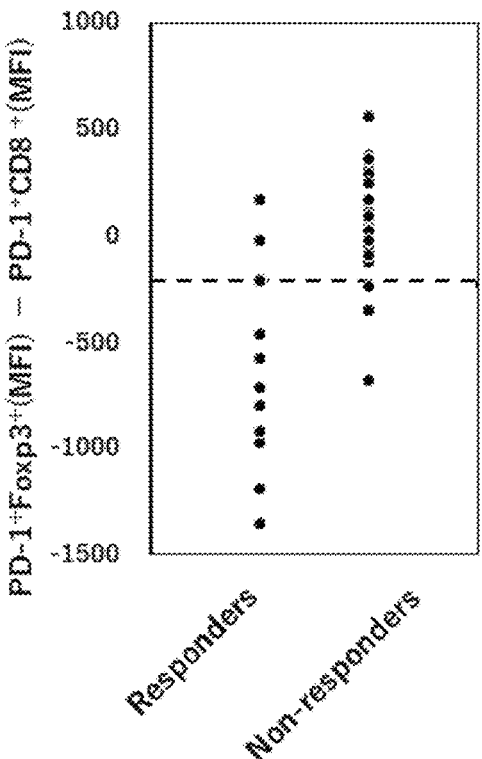

FIG. 9 It shows a result in which the Responder group and Non-responder group among patients with gastric cancer (29 cases) and patients with non-small cell lung cancer (18 cases) treated with Nivolumab were plotted on a graph with the value given by subtracting the MFI of PD-1 expression in the same origin CD8+ T cells from the MFI of PD-1 expression in Foxp3+ T cells in tumor tissue of each of the patient before administration of Nivolumab on the vertical axis. The dotted line in the figure represents the classification line derived by ROC analysis (Receiver Operating Characteristic analysis), which indicates that a patient with tumor in which the value is less than or equal to the value indicated by the classification line can be expected to benefit from Nivolumab.

Figure 10:
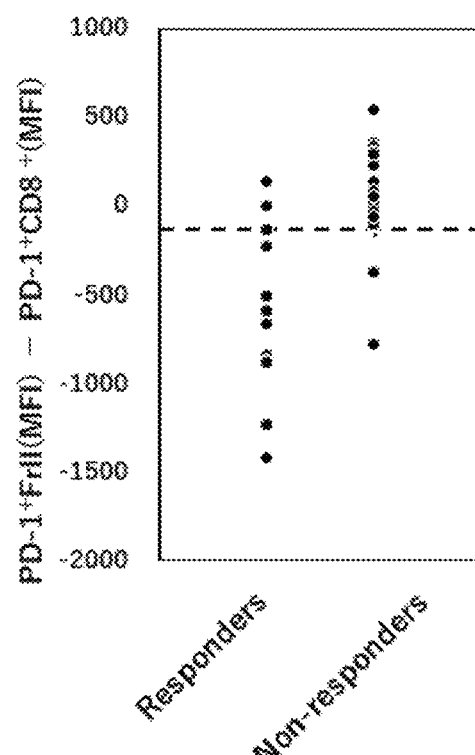

FIG. 10 It shows a result in which the Responder group and Non-responder group among patients with gastric cancer (29 cases) and patients with non-small cell lung cancer (18 cases) treated with Nivolumab were plotted on a graph with the value given by subtracting the MFI of PD-1 expression in the same origin CD8$^+$ T cells from the MFI of PD-1 expression in Treg cells (Fr.II) in tumor tissue of each of the patient before administration of Nivolumab on the vertical axis. The dotted line in the figure represents the classification line derived by ROC analysis, which indicates that a patient with tumor in which the value is less than or equal to the value indicated by the classification line can be expected to benefit from Nivolumab.

DESCRIPTION OF EMBODIMENTS

Examples of the "immune checkpoint inhibitor" in the present specification include an anti-PD-1 antibody (e.g., Nivolumab, Cemiplimab, Pembrolizumab, Spartalizumab, Tislelizumab, Dostarlimab, Toripalimab Camrelizumab, Genolimzumab, Sintilimab, Lodapolimab, Retifanlimab, Balstilimab, Serplulimab, Budigalimab, Prolgolimab, Sasanlimab Cetrelimab, Zimberelimab, Penpulimab, AMP-514, STI-A1110, ENUM 388D4, ENUM 244C8, GLS010, CS1003, BAT-1306, AK103, BI 754091, LZM009, CMAB819, Sym021, SSI-361, JY034, HX008, ISU106 or CX-188, etc.), anti-PD-L1 antibody (e.g., Atezolizumab, Avelumab, Durvalumab, Manelimab, Pacmilimab, Envafolimab Cosibelimab, BMS-936559, STI-1014, HLX20, SHR-1316, CS1001, MSB2311, BGB-A333, KL-A167, AK106, AK104, ZKAB001, FAZ053, CBT-502 and JS003, etc.), PD-1 antagonist (e.g., AUNP-12, each compound such as BMS-M1 to BMS-M10 (see WO2014/151634, WO2016/039749, WO2016/057624, WO2016/077518, WO2016/100285, WO2016/100608, WO2016/126646, WO2016/149351, WO2017/151830 and WO2017/176608), BMS-1, BMS-2, BMS-3, BMS-8, BMS-37, BMS-200, BMS-202, BMS-230, BMS-242, BMS-1001, BMS 1166 (see WO2015/034820, WO2015/160641, WO2017/066227 and Oncotarget. 2017 Sep. 22; 8(42): 72167-72181), each compound such as Incyte-1 to Incyte-6 (see WO2017/070089, WO2017/087777, WO2017/106634, WO2017/112730, WO2017/192961 and WO2017/205464), each compound such as CAMC-1 to CAMC-4 (see WO2017/202273, WO2017/202274, WO2017/202275 and WO2017/202276), RG_1 (see WO2017/118762) and DPPA-1 (see Angew. Chem. Int. Ed. 2015, 54, 11760-11764), etc.), PD-L1/VISTA antagonist (e.g., CA-170 etc.), PD-L1/TIM3 antagonist (e.g., CA-327 etc.), anti-PD-L2 antibody, PD-L1 fusion protein, PD-L2 fusion protein (e.g., AMP-224 etc.), anti-CTLA-4 antibody (e.g., Ipilimumab, Zalifrelimab, Nurulimab and Tremelimumab, etc.), anti-LAG-3 antibody (e.g., Relatlimab, Ieramilimab, Fianlimab, Encelimab and Mavezelimab, etc.), LAG-3 fusion protein (e.g., IMP321 etc.), anti-Tim3 antibody (e.g., MBG 453 and Cobolimab, etc.), anti-KIR antibody (e.g., Lirilumab, IPH2101, LY3321367 and MK-4280, etc.), anti-BTLA antibody, anti-TIGIT antibody (e.g., Tiragolumab, Etigilimab, Vibostolimab and BMS-986207, etc.), anti-VISTA antibody (e.g., Onvatilimab etc.), anti-CSF-1R antibody or CSF-1R inhibitor (e.g., Cabiralizumab, Emactuzumab, LY3022855, MCS-110, IMC-CS4, AMG820 Pexidartinib, BLZ945 and ARRY-382, etc.). Furthermore, in the present specification, pharmaceutical agents containing these substances as active ingredients are referred to as "immune checkpoint inhibitors". Note here that Nivolumab can be manufactured according to the method described in WO2006/121168, Pembrolizumab can be manufactured according to the method described in WO2008/156712, BMS-936559 can be manufactured according to the method described in WO2007/005874, and Ipilimumab can be manufactured according to the method described in WO2001/0144.

The "immune checkpoint inhibitor" in the present invention is preferably an anti-PD-1 antibody and anti-PD-L1 antibody, and in particular, preferable examples of anti-PD-1 antibodies include Nivolumab, Cemiplimab, Pembrolizumab, Spartalizumab Tislelizumab, Dostarlimab, Toripalimab, Camrelizumab, Genolimzumab, Sintilimab, Lodapolimab, Retifanlimab, Balstilimab, Serplulimab, Budigalimab, Prolgolimab, Sasanlimab, Cetrelimab, Zimberelimab and Penpulimab, and examples of anti-PD-L1 antibodies include Atezolizumab, Avelumab, Durvalumab, Manelimab, Pacmilimab, Envafolimab, Cosibelimab and BMS-936559.

Examples of the "evaluation items" in the biomarkers of the present invention include the following (1) to (12), those are, (1) the percentage (%) of CCR7 expressing cells among CD8$^+$ T cells in tumor tissue or blood from a patient with malignant tumor, (2) the number of PD-1 expressing cells among the CD8$^+$ T cells, the common logarithm of the same number of cells, or the common logarithm of the value given by adding 1 to the same number of cells, (3) the ratio of the MFI of PD-1 expression in the CD8$^+$ T cells to the MFI of PD-1 expression in the same origin Foxp3$^+$ T cells, or the square root of the ratio, (4) the percentage (%) of PD-1 expressing cells among the same origin Treg cells (Fr.III), (5) the percentage (%) of PD-1 expressing cells among the Foxp3$^+$ T cells, (6) the percentage (%) of PD-1 expressing cells among the same origin Treg cells (Fr. II), (7) the percentage (%) of PD-1 expressing cells among the same origin CD4$^+$ T cells, (8) the percentage (%) of PD-1 expressing cells among the CD8$^+$ T cells, (9) the ratio of the MFI of PD-1 expression in the same origin CD3$^+$ cells to the MFI of PD-1 expression in the Treg cells (Fr. II), or the square root of the ratio,

(10) the percentage (%) of PD-1 expressing cells among the CD4$^+$ T cells,

(11) the value given by subtracting the MFI of PD-1 expression in the CD8$^+$ T cells from the MFI of PD-1 expression in the Foxp3$^+$ T cells, and

(12) the value given by subtracting the MFI of PD-1 expression in the CD8$^+$ T cells from the MFI of PD-1 expression in the Treg cells (Fr. II).

In the present specification, CD8$^+$ T cells mean cells which are positive for surface antigen CD8 among T cells and can be identified, for example, as CD3-positive, CD4-negative and CD8-positive cells.

In the present specification, CD4$^+$ T cells mean cells which are positive for CD4 among T cells In the present specification, CD3$^+$ cells mean cells which are positive for CD3.

In the present specification, Foxp3$^+$ T cells mean cells which are positive for Foxp3 among T cells.

In the present specification, Treg cells can be identified, for example, as CD3-positive, CD4-positive, CD8-negative and Foxp3-positive cells, and in the present specification, "Treg cells (Fr. II)" (synonymous with "Fraction II Treg cells" or "eTreg cells") are effector Treg cells which have particularly strong immunosuppressive effects and are responsible for immunosuppressive activity among Treg cells, and can be identified as, for example, CD45RA-negative, CD25-positive and Foxp3-strongly positive Treg cells (Immunity, Volume 30, Issue 6, 2009, See pp. 899-911 and International Immunology, Volume 28, No. 8, 2016, pp. 401-409). Furthermore, in the present specification, "Treg cells (Fr. III)" (synonymous with "Fraction III Treg cells") can be identified as, for example, CD45RA-negative, CD25-positive, and Foxp3-weakly positive Treg cells. Note here that in the present specification, "positive" means that a marker molecule is expressed on cell surface and the specific binding of antibody to the marker molecule can be confirmed with a certain intensity, and "negative" means that the specific binding of antibody to the marker molecule cannot be confirmed with a certain intensity.

Examples of "tumor tissues" from which the immune cells constituting each evaluation item in the present invention are harvested include at least a tumor mass itself and tissue containing tumor-infiltrating vicinity or lymph nodes adjacent to tumor and the like, which can be harvested by publically known methods, such as forceps biopsy, puncture aspiration, needle biopsy, surgical biopsy or surgical operation for tumor removal. Furthermore, in the present invention, examples of "blood" from which the immune cells constituting each evaluation item are harvested include peripheral blood. Samples derived from the tumor tissue may be extracted after mechanically crushing the tumor tissue by publically known methods, or further if necessary, may also be isolated and further purified to be immune cells constituting each evaluation item. The destruction of the tumor tissue can also be enzymatically done. On the other hand, the samples derived from blood may be blood itself, or further if necessary, may also be isolated and further purified to be immune cells constituting each evaluation item, by specific gravity centrifugation method or the like.

In the present invention, the number of CD8$^+$ T cells, the number of CD4$^+$ T cells, the number of Foxp3$^+$ T cells, the respective number of Treg cells (Fr. II) and Treg cells (Fr. III), and the number of PD-1 expressing cells thereof and the number of CCR7 expressing CD8$^+$ T cells can be measured and calculated, for example, by flow cytometry, immunostaining or the like. Specifically, mononuclear cells isolated from tumor tissue and peripheral blood are stained with fluorescent-labeled antibodies. Herein, the fluorescent-labeled antibodies may also be those labeled with unlabeled primary antibody and fluorescent-labeled secondary antibodies thereto. The mononuclear cells stained with the same antibody are detected by flow cytometry. Herein, PD-1 expressing cells among each kind of cell are a population of cells expressing PD-1 at or beyond a certain threshold level, for example, those which are not detected in flow cytometry measurements when negative control fluorescent-labeled antibodies not recognizing PD-1 are used or when fluorescent-labeled antibodies to PD-1 are not used, but which are detected only when fluorescent-labeled antibodies to PD-1 are used. The same is true for CCR7 expressing cells.

Similarly, the MFI of PD-1 expressions in CD8$^+$ T cells, CD3$^+$ cells, Foxp3$^+$ T cells, and Treg cells (Fr. II) can also be measured by, for example, flow cytometry, respectively. Herein, these MFIs can be used to calculate a ratio thereamong instead of the respective numbers of expression (expression levels) per cell. In determining the number of antigen molecules expressed per cell, publically known measurement methods using fluorescent-labeled beads (e.g., methods using BD QuantiBRITE (registered trademark) PE Kit and Quantum (registered trademark) FITC MESF Kit, etc.) used to create calibration curves for antigen molecule quantification may be used as appropriate. As a unit of the number of cell surface antigen molecules expressed (expression level), used in these assays, for example, Molecules of Equivalent Soluble Fluorochrome (MESF) may be used.

In the present specification, the "percentage (%) of PD-1 expressing cells among CD8$^+$ T cells" is synonymous with the term "ratio (%) of PD-1 expressing cells among CD8$^+$ cells" or "percentage (%) of PD-1 expression among CD8$^+$ T cells", and the relationship among these definitions is true with respect to the percentage (%) of PD-1 expressing cells among CD4$^+$ T cells, Foxp3$^+$ T cells, Treg cells (Fr. II) and Treg cells (Fr. III), respectively.

In the present specification, the meaning "prior to administration of the agent containing an immune checkpoint inhibitory substance as an active ingredient" or "prior to administration of an immune checkpoint inhibitor" also include the case where the agent containing the immune checkpoint inhibitory substance as an active ingredient is administered for the first time without any treatment histories, as well as a case of being prior to administration of the same agent when having a history of treatment with the same immune checkpoint inhibitor or other anti-neoplastic agents (including immune checkpoint inhibitors other than the same immune checkpoint inhibitor).

The term "about" used in the present specification means that it may vary below or beyond the indicated value within a range of 10%. Alternatively, it means that those which become the same values by rounding are also included.

Examples of preferable combinations of the two sets of evaluation items constituting the biomarker of the present invention include each combination listed in the following (A) to (C), those are, (A) a combination of (1) (i) the percentage (%) of CCR7 expressing cells among CD8$^+$ T cells in tumor tissue or blood from a patient with malignant tumor, or (ii) the number of PD-1 expressing cells among the CD8$^+$ T cells, the common logarithm of the same number of cells, or the common logarithm of the value given by adding 1 to the same number of cells, and (2) the ratio of the MFI of PD-1 expression in the CD8$^+$ T cells to the MFI of PD-1 expression in the same origin Foxp3$^+$ T cells, or the square root of the ratio;

(B) a combination of (1) any one selected from (i) the percentage (%) of PD-1 expressing cells among Treg cells (Fr.III) in tumor tissue or blood from a patient with malignant tumor, (ii) the ratio of the MFI of PD-1 expression in the same origin CD8$^+$ T cells to the MFI of PD-1 expression in the same origin Foxp3$^+$ T cells, or the square root of the ratio, (iii) the percentage (%) of PD-1 expressing cells among the Foxp3$^+$ T cells, (iv) the percentage (%) of PD-1 expressing cells among the same origin Treg cells (Fr. II), and (v) the percentage (%) of PD-1 expressing cells among the same origin CD4$^+$ T cells, and (2) the percentage (%) of PD-1 expressing cells among the CD8$^+$ T cells, and (C) a combination of (1) the ratio of the MFI of PD-1 expression in the CD3$^+$ cells to the MFI of PD-1 expression in the Treg cells (Fr. II), or the square root of the ratio, and (2) the percentage (%) of PD-1 expressing cells among the CD4$^+$ T cells.

Furthermore, specific conditions for identifying a patient with malignant tumor which can or cannot be expected to benefit from immune checkpoint inhibitors in combination of two sets of the same predetermined evaluation items can be predetermined according to the following procedure.

That is, (1) measuring two sets of predetermined evaluation items for a patient with malignant tumor prior to administration of an immune checkpoint inhibitor, (2) administering the immune checkpoint inhibitor, (3) determining the efficacy of the immune checkpoint inhibitor in a patient using a predetermined determining method, (4) plotting each patient determined as being effective or ineffective based on the measured values in the two sets of evaluation items, respectively, (5) deriving, by machine learning, a classification line such that the fα value becomes maximized when one or more classification lines (discrimination lines) dividing (discriminating) the effective group and ineffective group are varied in arbitrary values represented by the parameter: α value (a value of 0≤α≤1) in weighted F-measure (fα) which is one of evaluation indexes in machine learning, and (6) defining a classification line or combination of plural classification lines derived for the two sets of evaluation items as a specific condition for identifying a patient with malignant tumor by the two sets of evaluation items for each biomarker, respectively.

Herein, fα can be calculated by the following formula:

$$f\alpha = \frac{Recall \times Precision}{\alpha \times Recall + (1-\alpha) \times Precision}$$ [Formula 75]

and the α value in the formula, for example, can be set as 0.5 in case that both are distributed so as to include as many effective patients as possible but not to include as many ineffective patients as possible, and in case that the effective ones are majority, for example, that both are distributed so as to include as many effective patients as possible, the α value can be set to 0.05 while in case that both are distributed so as not to include as many ineffective patients as possible, for example, the α value can be set to 0.95. Herein, the term "Recall" in the formula means the reproduction rate, which is the percentage of patients in which it was predicted to be effective under the efficacy assessment out of the patients in which it was actually effective, and can be calculated by the following formula:

$$Recall = \frac{[True-Positive]}{[True-Positive]+[False-Negative]}$$ [Formula 76]

[wherein the term "True-Positive" represents the number of patients in which it was correctly predicted out of patients in which it was predicted to be effective under the dichotomous classification based on whether the immune checkpoint inhibitor is effective or not, and the term "False-Negative" represents the number of patients in which it was incorrectly predicted to be effective out of patients in which it was predicted to be ineffective] On the other hand, the term "Precision" in the preceding formula for fα means the rate of conformity, which is the percentage of patients in which it is actually effective out of patients in which it was predicted to be effective under the efficacy assessment, and can be calculated by the following formula:

$$Precision = \frac{[True-Positive]}{[True-Positive]+[False-Positive]}$$ [Formula 77]

[wherein the term "False-Positive" represents the number of patients in which it was incorrectly predicted to be effective out of patients in which it was predicted to be effective under the dichotomous classification, and other symbols have the same meanings as above]

In addition to the above-mentioned weighted F value f(α), accuracy, specificity, or a composite index containing them can also be used in setting the specific conditions constituting the biomarker of the present invention. For example, it can be determined by ROC analysis (Receiver Operating Characteristic analysis) (see Clinical Pathology 42(6): 585-590, 1994).

For example, if the tumor is solid cancer, the efficacy of the immune checkpoint inhibitor can be determined according to Complete Response (CR), Partial Response (PR), Progressive Disease (PD), and Stable Disease (SD) which are determined according to the RECIST guidelines (Response Evaluation Criteria in Solid Tumor, 2000). For example, each patient with CR, PR or SD can be determined to be effective (hereinafter, may be described as the "Responder group"), and patients with PD may be determined to be ineffective (hereinafter, may be described as the "Non-Responder group"). Alternatively, it may be determined to be effective in each patient with CR or PR, and may be determined to ineffective in each patient with SD and PD, or it may be determined to be effective in each patient with CR or PR and patient in which SD was maintained for at least 6 months, and may be determined to be ineffective in patients in which SD was maintained only for less than 6 months and patients with PD. The determination based on the same criteria can be made, for example, at up to 12 months, preferably at up to 10 months, more preferably at 8 months and furthermore preferably at 6 months from the start of treatment with immune checkpoint inhibitors. The overall response rate (ORR), progression-free survival (PFS), overall survival (OS), survival rate or median survival time or the like can also be used to determine whether it is effective or not. The patients in which PFS was maintained for 70 days may be determined to be effective while the patients in which PFS was maintained for less than 70 days may be determined to be ineffective.

Biomarker 1

When the percentage (%) of CCR7 expressing cells among CD8$^+$ T cells in tumor tissue or blood and the ratio of the MFI of PD-1 expression in the CD8$^+$ T cells to the MFI of PD-1 expression in the same origin Foxp3$^+$ T cells are selected as the two sets of evaluation items, a patient with malignant tumor in which they meet the condition represented by (1) the following formula:

$$Y_1 \geq a_{1-1} \times X_1 + Y_{1-1}$$ [Formula 78]

[wherein $Y_1$ represents the percentage (%) of CCR7 expressing cells among the CD8$^+$ T cells, $a_{1-1}$ represents a value of about −637, $X_1$ represents the square root of the ratio of the MFI of PD-1 expression in the CD8$^+$ T cells to the MFI of PD-1 expression in the Foxp3$^+$ T cells, and $Y_{1-1}$ represents an arbitrary value from about 784 to about 914], or (2) the two conditions represented by (i) the following formula:

$$Y_1 \leq a_{1-2} \times X_1 + Y_{1-2}$$ [Formula 79]

[wherein $a_{1-2}$ represents a value of about −24.0, $Y_{1-2}$ represents an arbitrary value from about 39.0 to about 50.9, and other symbols have the same meanings as above], and (ii) the following formula:

$$Y_1 \leq a_{1-3} \times X_1 + Y_{1-3}$$ [Formula 80]

[wherein $a_{1-3}$ represents a value of about 666, $Y_{1-3}$ represents an arbitrary value from about −652 to about −522, and other symbols have the same meanings as above] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Figure 1:
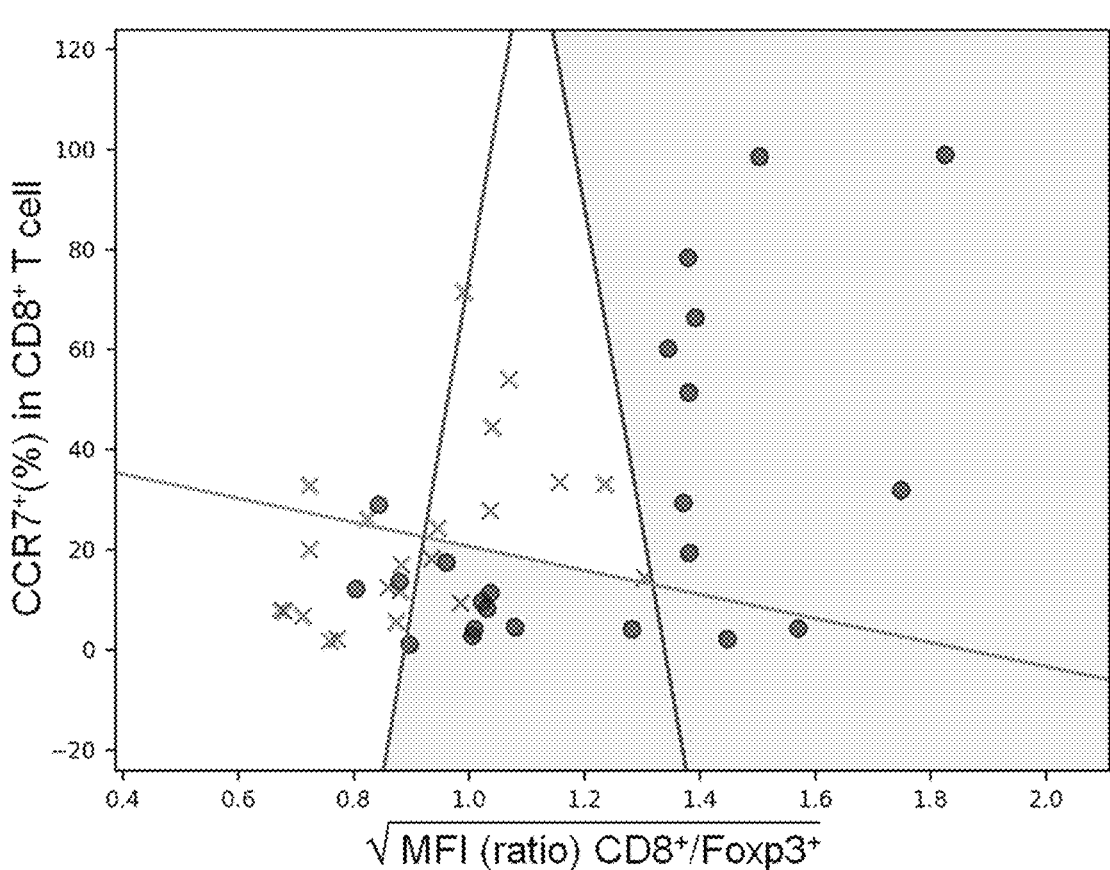
FIG. 1 It shows a result in which the Responder group (black circles in the figure) and Non-responder group (x marks in the figure) among patients with gastric cancer (29 cases) and patients with non-small cell lung cancer (16 cases) treated with Nivolumab were plotted on a graph with the percentage (%) of CCR7 expressing cells among CD8+ T cells in tumor tissue of each of the patient before administration of Nivolumab on the vertical axis, and the square root of the ratio of the MFI of PD-1 expression in the CD8+ T cells to the MFI of PD-1 expression in the same origin Foxp3+ T cells on the horizontal axis. The three solid lines in the figure represent classification lines (discrimination lines) derived by machine learning using the weighted f-measure (fα) as an indicator so that the value of fα is maximized when the α value is 0.5, and the shaded area on the right side of the figure indicates that a patient with tumor plotted therein can be expected to benefit from Nivolumab.

Herein, $Y_{1-1}$ in the preceding formula is preferably an arbitrary value from about 784 to about 853 or an arbitrary value from about 853 to about 914, and more preferably about 853, $Y_{1-2}$ is preferably an arbitrary value from about 44.6 to about 50.9 or an arbitrary value from about 39.0 to about 44.6, and more preferably about 44.6, and $Y_{1-3}$ is preferably an arbitrary value from about −591 to about −522 or an arbitrary value from about −652 to about −591, and more preferably about −591. When the $\alpha$ value in the weighted f-value (f$\alpha$) is set to 0.95, $Y_{1-1}$, $Y_{1-2}$ and $Y_{1-3}$ are about 914, about 39.0 and about −652, respectively, and when the $\alpha$ value is set to 0.05, $Y_{1-1}$, $Y_{1-2}$ and $Y_{1-3}$ are about 784, about 50.9 and about −522, respectively. When the $\alpha$ value is set to 0.5, $Y_{1-1}$, $Y_{1-2}$, and $Y_{1-3}$ are about 853, about 44.6 and about −591, respectively, but in selecting a patient with malignant tumor which can be expected to benefit more from the immune checkpoint inhibitor, the combination of the preceding conditions (the combination of the classification lines represented by the three solid lines in FIG. 1) is defined by the values of $Y_{1-1}$, $Y_{1-2}$, and $Y_{1-3}$ when the $\alpha$ value is set to 0.5 is most preferable.

Biomarker 2

When the respective percentages (%) of PD-1 expressing cells among Treg cells (Fr.III) and CD8$^+$ T cells in tumor tissue or blood are selected as the two sets of evaluation items, a patient with malignant tumor in which they meet (1) the condition represented by the following formula:

$$Y_2 \geq a_{24} \times X_2 + Y_{2-1} \qquad \text{[Formula 81]}$$

[wherein $Y_2$ represents the percentage (%) of PD-1 expressing cells among the Treg cells (Fr. III), and $a_{2-1}$ represents a value of about 0.765, $X_2$ represents the percentage (%) of PD-1 expressing cells among the CD8$^+$ T cells, and $Y_{2-1}$ represents an arbitrary value from about 50.6 to about 59.2], or (2) the condition represented by the following formula:

$$Y_2 \leq a_{2-2} \times X_2 + Y_{2-2} \qquad \text{[Formula 82]}$$

[wherein $a_{2-2}$ represents a value of about 1.56, $Y_{2-2}$ represents an arbitrary value from about −44.1 to −14.5, and other symbols have the same meanings as above] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{2-1}$ in the preceding formula is preferably an arbitrary value from about 50.6 to about 54.1 or an arbitrary value from about 54.1 to about 59.2, and more preferably about 54.1, and $Y_{2-2}$ is preferably an arbitrary value from about −26.6 to −14.5 or an arbitrary value from about −44.1 to about −26.6, and more preferably about −26.6. When the $\alpha$ value in the weighted F value (f$\alpha$) is set to 0.95, $Y_{2-1}$ and $Y_{2-2}$ are about 59.2 and about −44.1, respectively, and when the $\alpha$ value is set to 0.05, $Y_{2-1}$ and $Y_{2-2}$ are about 50.6 and about −14.5, respectively. When the $\alpha$ value is set to 0.5, $Y_{2-1}$ and $Y_{2-2}$ are about 54.1 and about −26.6, respectively, but in selecting a patient with malignant tumor which can be expected to benefit more from the immune checkpoint inhibitor, the combination of the preceding conditions defined by the values of $Y_{2-1}$ and $Y_{2-2}$ when the $\alpha$ value is set to 0.5 (the combination of the classification lines represented by the two solid lines in FIG. 2) is most preferable.

Biomarker 3

When the number of PD-1 expressing cells among the CD8$^+$ T cells in tumor tissue or blood and the ratio of the MFI of PD-1 expression in the CD8$^+$ T cells to the MFI of PD-1 expression in the same origin Foxp3$^+$ T cells are selected as the two sets of evaluation items, a patient with malignant tumor in which they meet (1) the condition represented by (i) the following formula:

$$\text{Log}_{10}(Y_3+1) \geq a_{3-1} \times X_3 + Y_{3-1} \qquad \text{[Formula 83]}$$

[wherein $Y_3$ represents the number of PD-1 expressing cells among the CD8$^+$ T cells, $a_{3-1}$ represents a value to about −1.59, $X_3$ represents the square root of the ratio of the MFI of PD-1 expression in the CD8$^+$ T cells to the same MFI in the Foxp3$^+$ T cells, and $Y_{3-1}$ represents an arbitrary value from about 4.09 to about 4.89], or
(ii) the following formula:

$$\text{Log}_{10}(Y_3) \geq a_{3-1} \times X_3 + Y_{3-1} \qquad \text{[Formula 84]}$$

[wherein all symbols have the same meanings as above], or (2) the condition represented by (i) the following formula:

$$\text{Log}_{10}(Y_3+1) \geq a_{3-2} \times X_3 + Y_{3-2} \qquad \text{[Formula 85]}$$

[wherein $a_{3-2}$ represents a value of about −9.05, $Y_{3-2}$ represents an arbitrary value from about 10.7 to about 13.3, and other symbols have the same meanings as above], or
(ii) the following formula:

$$\text{Log}_{10}(Y_3) \geq a_{3-2} \times X_3 + Y_{3-2} \qquad \text{[Formula 86]}$$

[wherein all symbols have the same meanings as above] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{3-1}$ in the preceding formula is preferably an arbitrary value from about 4.09 to about 4.42 or an arbitrary value from about 4.42 to about 4.89, and more preferably about 4.42, and $Y_{3-2}$ is preferably an arbitrary value from about 11.7 to about 13.3 or an arbitrary value from about 10.7 to about 11.7, and more preferably about 11.7. When the $\alpha$ value in the weighted F value (f$\alpha$) is set to 0.95, $Y_{3-1}$ and $Y_{3-2}$ are about 4.89 and about 13.3, respectively, and when the $\alpha$ value is set to 0.05, $Y_{3-1}$ and $Y_{3-2}$ are about 4.09 and about 10.7, respectively. When the $\alpha$ value is set to 0.5, $Y_{3-1}$ and $Y_{3-2}$ are about 4.42 and about 11.7, respectively, but in selecting a patient with malignant tumor which can be expected to benefit more from the immune checkpoint inhibitor, the combination of the preceding conditions defined by the values of $Y_{3-1}$ and $Y_{3-2}$ when the $\alpha$ value is set to 0.5 (the combination of the classification lines represented by the two solid lines in FIG. 3) is most preferable.

Biomarker 4

When the ratio of the MFI of PD-1 expression in CD8$^+$ T cells in tumor tissue or blood to the MFI of PD-1 expression in the same origin Foxp3$^+$ T cells and the percentage (%) of PD-1 expressing cells among the CD8$^+$ T cells are selected as the two sets of evaluation items, a patient with malignant tumor in which they meet (1) the condition represented by the following formula:

$$Y_4 \geq a_{4-1} \times X_4 + Y_{4-1} \qquad \text{[Formula 87]}$$

[wherein $Y_4$ represents the square root of the ratio of the MFI of PD-1 expression in the CD8$^+$ T cells to the MFI of PD-1 expression in the Foxp3$^+$ T cells, $a_{4-1}$ represents a value of about –0.00273, $X_4$ represents the percentage (%) of PD-1 expressing cells among the CD8$^+$ T cells, and $Y_{4-1}$ represents an arbitrary value from about 0.905 to about 1.46], or (2) the condition represented by the following formula:

$$Y_4 \geq a_{4-2} \times X_4 + Y_{4-2} \qquad \text{[Formula 88]}$$

[wherein $a_{4-2}$ represents a value of about –0.0294, $Y_{4-2}$ represents an arbitrary value from about 2.18 to 3.31, and other symbols have the same meanings as above] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{4-1}$ in the preceding formula is preferably an arbitrary value from about 0.905 to about 1.18 or an arbitrary value from about 1.18 to about 1.46, and more preferably about 1.18, and $Y_{4-2}$ is preferably an arbitrary value from about 2.74 to about 3.31 or an arbitrary value from about 2.18 to about 2.74, and more preferably about 2.74. When the $\alpha$ value in the weighted F value (f$\alpha$) is set to 0.95, $Y_{4-1}$ and $Y_{4-2}$ are about 1.46 and about 3.31, respectively, and when the $\alpha$ value is set to 0.05, $Y_{4-1}$ and $Y_{4-2}$ are about 0.905 and about 2.18, respectively. When the $\alpha$ value is set to 0.5, $Y_{4-1}$ and $Y_{4-2}$ are about 1.18 and about 2.74, respectively, but in selecting a patient with malignant tumor which can be expected to benefit more from the immune checkpoint inhibitor, the combination of the preceding conditions defined by the values of $Y_{4-1}$ and $Y_{4-2}$ when the $\alpha$ value is set to 0.5 (the combination of the classification lines represented by the two solid lines in FIG. 4) is most preferable.

Biomarker 5

When the respective percentages (%) of PD-1 expressing cells among Foxp3$^+$ T cells and CD8$^+$ T cells in tumor tissue or blood are selected as the two sets of evaluation items, a patient with malignant tumor in which they meet the condition represented by the following formula:

$$Y_5 \geq a_5 \times X_5 + Y_{5-1} \qquad \text{[Formula 89]}$$

[wherein $Y_5$ represents the percentage (%) of PD-1 expressing cells among the Foxp3$^+$ T cells, $a_5$ represents a value of about 2.34, $X_5$ represents the percentage (%) of PD-1 expressing cells among the CD8$^+$ T cells, and $Y_{5-1}$ represents an arbitrary value from about –117 to about 131] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{5-1}$ in the preceding formula is preferably an arbitrary value from about –117 to about –54.4 or an arbitrary value from about –54.4 to about 131, and more preferably about –54.4. When the $\alpha$ value in the weighted F value (f$\alpha$) is set to 0.95, $Y_{5-1}$ is about –117, when the $\alpha$ value is set to 0.05, $Y_{5-1}$ is about 131. When the $\alpha$ value is set to 0.5, $Y_{5-1}$ is about –54.4, but in selecting a patient with malignant tumor which can be expected to benefit more from the immune checkpoint inhibitor, the preceding condition defined by the value of $Y_{5-1}$ when the $\alpha$ value is 0.5 (the classification line represented by the solid line in FIG. 5) is most preferable.

Biomarker 6

When the respective percentages (%) of PD-1 expressing cells among Treg cells (Fr.II) and CD8$^+$ T cells in tumor tissue or blood are selected as the two sets of evaluation items, a patient with malignant tumor in which they meet (1) the condition represented by the following formula:

$$Y_6 \geq a_{6-1} \times X_6 + Y_{6-1} \qquad \text{[Formula 90]}$$

[wherein $Y_6$ represents the percentage (%) of PD-1 expressing cells among the Treg cells (Fr. II), $a_{6-1}$ represents a value of about 1.69, $X_6$ represents the percentage (%) of PD-1 expressing cells among the CD8$^+$ T cells, and $Y_{6-1}$ represents an arbitrary value from about 21.4 to about 44.1], or (2) the condition represented by the following formula:

$$Y_6 \leq a_{6-2} \times X_6 + Y_{6-2} \qquad \text{[Formula 91]}$$

[wherein $a_{6-2}$ represents a value of about 1.78, $Y_{6-2}$ represents an arbitrary value from about –80.6 to about –21.0, and other symbols have the same meanings as above] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{6-1}$ in the preceding formula is preferably an arbitrary value from about 21.4 to about 31.8 or an arbitrary value from about 31.8 to about 44.1, more preferably about 31.8, and $Y_{6-2}$ is preferably an arbitrary value from about –48.2 to about –21.0 or an arbitrary value from about –80.6 to about –48.2. more preferably, about –48.2. When the $\alpha$ value in the weighted F value (f$\alpha$) is set to 0.95, $Y_{6-1}$ and $Y_{6-2}$ are about 44.1 and about –80.6, respectively, and when the $\alpha$ value is set to 0.05, $Y_{6-1}$ and $Y_{6-2}$ are about 21.4 and about –21.0, respectively. When the $\alpha$ value is set to 0.5, $Y_{6-1}$ and $Y_{6-2}$ are about 31.8 and about –48.2, respectively, but in selecting a patient with malignant tumor which can be expected to benefit more from the immune checkpoint inhibitor, the combination of the preceding conditions defined by the values of $Y_{6-1}$ and $Y_{6-2}$ when the $\alpha$ value is set to 0.5 (the combination of the classification lines represented by the two solid lines in FIG. 6) is most preferable.

Biomarker 7

When the respective percentages (%) of PD-1 expressing cells among CD4$^+$ T cells and CD8$^+$ T cells in tumor tissue or blood are selected as the two sets of evaluation items, a patient with malignant tumor in which they meet (1) the condition represented by the following formula:

$$Y_7 \leq a_{7-1} \times X_7 + Y_{7-1} \qquad \text{[Formula 92]}$$

[wherein $Y_7$ represents the percentage (%) of PD-1 expressing cells among the CD4$^+$ T cells, and $a_{7-1}$ represents a value of about 0.227, $X_7$ represents the percentage (%) of PD-1 expressing cells among the CD8$^+$ T cells, and $Y_{7-1}$ represents an arbitrary value from about –13.9 to about 4.03], or (2) the condition represented by the following formula:

$$Y_7 \leq a_{7-2} \times X_7 + Y_{7-2} \qquad \text{[Formula 93]}$$

[wherein $a_{7-2}$ represents a value of about 3.32, $Y_{7-2}$ represents an arbitrary value from about –199 to about 58.2, and other symbols have the same meanings as above] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{7\text{-}1}$ in the preceding formula is preferably an arbitrary value from about −13.9 to about −6.56 or an arbitrary value from about −6.56 to about 4.03, more preferably about −6.56, and $Y_{7\text{-}2}$ is preferably an arbitrary value from about −93.5 to about 58.2 or an arbitrary value from about −199 to about −93.5, more preferably about −93.5. When the α value in the weighted F value (fα) is set to 0.95, $Y_{7\text{-}1}$ and $Y_{7\text{-}2}$ are about −13.9 and about −199, respectively, and when the α value is set to 0.05, $Y_{7\text{-}1}$ and $Y_{7\text{-}2}$ are about 4.03 and about 58.2, respectively. When the α value is set to 0.5, $Y_{7\text{-}1}$ and $Y_{7\text{-}2}$ are about −6.56 and about −93.5, respectively, but in selecting a patient with malignant tumor which can be expected to benefit more from the immune checkpoint inhibitor, the combination of the preceding conditions defined by the values of $Y_{7\text{-}1}$ and $Y_{7\text{-}2}$ when the α value is set to 0.5 (the combination of the classification lines represented by the two solid lines in FIG. 7) is most preferable.

Biomarker 8

When the ratio of the MFI of PD-1 expression in the same origin $CD3^+$ cells to the MFI of PD-1 expression in Treg cells (Fr. II) in tumor tissue or blood and the percentage (%) of PD-1 expressing cells among the same origin $CD4^+$ T cells are selected as the two sets of evaluation items, a patient with malignant tumor in which they meet the condition represented by the following formula:

$$a_{8\text{-}1}{\times}X_8+Y_{8\text{-}1}\leq Y_8\leq a_{8\text{-}2}{\times}X_8+Y_{8\text{-}2} \qquad \text{[Formula 94]}$$

[wherein $Y_8$ represents the square root of the ratio of the MFI of PD-1 expression in the $CD3^+$ cells to the MFI of PD-1 expression in the Treg cells (Fr. II), $a_{8\text{-}1}$ represents a value of about −0.00338, $a_{8\text{-}2}$ represents a value of about 0.270, $X_8$ represents the percentage (%) of PD-1 expressing cells among the $CD4^+$ T cells, $Y_{8\text{-}1}$ represents an arbitrary value from about 0.939 to about 1.37 and $Y_{8\text{-}2}$ represents an arbitrary value from about −6.98 to about −0.654] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $Y_{8\text{-}1}$ in the preceding formula is preferably an arbitrary value from about 0.939 to about 1.17 or an arbitrary value from about 1.17 to about 1.37, more preferably about 1.17, and $Y_{8\text{-}2}$ is preferably an arbitrary value from about −4.10 to about −0.654 or an arbitrary value from about −6.98 to about −4.10, more preferably about −4.10. When the α value in the weighted F value (fα) is set to 0.95, $Y_{8\text{-}1}$ and $Y_{8\text{-}2}$ are about 1.37 and about −6.98, respectively, and when the α value is set to 0.05, $Y_{8\text{-}1}$ and $Y_{8\text{-}2}$ are about 0.939 and about −0.654, respectively. When the α value is set to 0.5, $Y_{8\text{-}1}$ and $Y_{8\text{-}2}$ are about 1.17 and −4.10, respectively, but in selecting a patient with malignant tumor which can be expected to benefit more from the immune checkpoint inhibitor, the combination of the preceding conditions defined by the values of $Y_{8\text{-}1}$ and $Y_{8\text{-}2}$ when the α value is set to 0.5 (the combination of the classification lines represented by the two solid lines in FIG. 8) is most preferable.

Biomarker 9

When the value given by subtracting the MFI of PD-1 expression in the same origin $CD8^+$ T cells from the MFI of PD-1 expression in $Foxp3^+$ T cells in tumor tissue or blood is selected as the evaluation item, a patient with malignant tumor in which they meet the condition represented by the following formula:

$$Y_{9\text{-}1}-_{9\text{-}2}\leq a_9 \qquad \text{[Formula 95]}$$

[wherein $Y_{9\text{-}1}$ represents the MFI of PD-1 expression in the $Foxp3^+$ T cells, $Y_{9\text{-}2}$ represents the MFI of PD-1 expression in the $CD8^+$ T cells, and $a_9$ represents an arbitrary from about −716 to about 166 (cut-off value)] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $a_9$ in the preceding formula is preferably an arbitrary value from about −462 to about 166 or from about −716 to about −3.96, more preferably an arbitrary value from about −462 to about −3.96, and furthermore is preferably about −208.

Biomarker 10

When the value given by subtracting the MFI of PD-1 expression in the same origin $CD8^+$ T cells from the MFI of PD-1 expression in Treg cells (Fr. II) is selected as the evaluation item, a patient with malignant tumor in which they meet the condition represented by the following formula:

$$Y_{10\text{-}1}-Y_{10\text{-}2}\leq a_{10} \qquad \text{[Formula 96]}$$

[wherein $Y_{10\text{-}1}$ represents the MFI of PD-1 expression in the Treg cells (Fr. II), $Y_{10\text{-}2}$ represents the MFI of PD-1 expression in the $CD8^+$ T cells, and $a_{10}$ represents an arbitrary value from about −842 to about 133 (cut-off value)] can be selected as a patient with malignant tumor which can be expected to benefit more from the immune checkpoint inhibitor, and a patient in which they do not meet the same two conditions can be selected as a patient with malignant tumor which cannot be expected to benefit from the immune checkpoint inhibitor.

Herein, $a_{10}$ in the preceding formula is preferably an arbitrary value from about −505 to about 133 or from about −842 to about −2.40, more preferably an arbitrary value from about −505 to about −2.40, and furthermore preferably about −131.

[Applicable Diseases and Patients]

Examples of the malignant tumors to which the therapeutic agents or methods for identifying patients of the present invention can be applied include, in case of solid cancer, one or more cancers selected from malignant melanoma (e.g., malignant melanoma in skin, oral mucosal epithelium or orbit, etc.), non-small cell lung cancer (e.g., squamous non-small cell lung cancer and non-squamous non-small cell lung cancer), small cell lung cancer, head and neck cancer (e.g., oral cancer, nasopharyngeal cancer, oropharyngeal cancer, hypopharyngeal cancer, laryngeal cancer, salivary gland cancer and tongue cancer), renal cell carcinoma (e.g., clear cell renal cell carcinoma), breast cancer, ovarian cancer (e.g., serous ovarian cancer and ovarian clear cell adenocarcinomas), nasopharyngeal cancer, uterine cancer (e.g., cervical cancer, endometrial cancer, and endometrial cancer), anal cancer (e.g., anal canal cancer), colorectal cancer (e.g., MSI-H and/or dMMR positive colorectal cancer), rectum cancer, colon cancer, hepatocellular carcinoma, esophageal cancer, esophageal adenocarcinoma, gastric cancer, esophagogastric junction cancer, small intestine cancer, pancreatic cancer, urothelial cancer (e.g., bladder cancer, upper urinary tract cancer, ureteral cancer, renal pelvis cancer and urethral tract cancer), prostate cancer, fallopian tube cancer, primary peritoneal cancer, malignant pleural mesothelioma, gallbladder cancer, bile duct cancer, biliary tract cancer, skin cancer (e.g., uveal melanoma and Merkel cell carcinoma), testicular cancer (germ cell tumor), vaginal cancer, vulvar cancer, penile cancer, endocrine cancer, thyroid cancer, parathyroid cancer, adrenal cancer, spinal tumor, brain tumor (e.g., glioma (e.g., glioblastoma and gliosarcoma) and meningioma), squamous cell carcinoma, bone/soft tissue sarcomas (e.g., Ewing sarcoma, childhood rhabdomyosarcoma, uterine leiomyosarcoma, chondrosarcoma, lung sarcoma, osteosarcoma and congenital fibrosarcoma) and Kaposi's sarcoma.

In case of hematological cancer, examples thereof include one or more cancers selected from multiple myeloma, malignant lymphoma (e.g., non-Hodgkin's lymphoma (e.g., follicular lymphoma, diffuse large B-cell lymphoma, MALT lymphoma, fungoid mycosis, Sezary syndrome, chronic or acute lymphocytic leukemia, peripheral T-cell lymphoma, extranodal NK/T-cell lymphoma, adult T-cell leukemia, B-cell lymphoblastic leukemia and T-cell lymphoblastic leukemia and lymphoplasmacytic lymphoma) and Hodgkin's lymphoma (e.g., classical Hodgkin's lymphoma and nodular lymphocyte-predominant Hodgkin's lymphoma)), leukemia (e.g., acute myeloid leukemia and chronic myeloid leukemia), primary central nervous system malignant lymphoma, myelodysplastic syndrome and myeloproliferative syndrome.

In the present specification, examples of the term "treating malignant tumor" include therapies (i) to decrease the proliferation of tumor cells, (ii) to reduce symptoms caused by malignant tumor, (iii) to improve the quality of life of a patient with malignant tumor, (iv) to reduce the dosage of other already administered other anti-neoplastic drugs or cancer therapeutic adjuvants and/or (v) to prolong the survival of a patient with malignant tumor. The term "suppressing the progress of malignant tumor" means to delay the progress of malignant tumor, to stabilize symptoms associated with malignant tumor and to reverse the progress of symptoms. Furthermore, the term "suppressing the recurrence of malignant tumor" means to prevent the recurrence of malignant tumor in a patient in which cancer lesion had been completely or substantially eliminated or removed by treatment of malignant tumor or cancer resection surgery.

In the present invention, the immune checkpoint inhibitor can be prescribed to a patient with malignant tumor which meets the condition of at least any one of Biomarkers 1 to 10 according to the present invention and is the following patient with malignant tumor, that is, (a) a patient with malignant tumor on which the therapeutic effects of other anti-neoplastic drugs are insufficient or not sufficient, or patient with malignant tumor worsened after treatment with other anti-neoplastic drugs, (b) a patient with incurable or unresectable, metastatic, recurrent, refractory and/or distant metastatic malignant tumor, (c) a patient with malignant tumor in which TPS or CPS is 50% or more, 25% or more, 10% or more, 5% or 1% or more, (d) a patient with MSI-H or dMMR malignant tumor, (e) a patient with BRAF V600E mutation-positive malignant melanoma or non-small cell lung cancer, (f) a patient with EGFR gene mutation-positive or ALK fusion gene-positive malignant tumor or (g) a patient with malignant tumor with TMB high frequency.

On the other hand, in the present invention, the immune checkpoint inhibitor may be required to be prescribed to a patient with malignant tumor which meets the condition of at least any one of Biomarkers 1 to 10 according to the present invention and is the following patient with malignant tumor, that is, (a) a patient with malignant tumor without any histories of treatment of other anti-neoplastic drugs, (b) a patient with malignant tumor in which TPS or CPS is less than 50%, less than 25%, less than 10%, less than 5% or less than 1%, (c) a patient with malignant tumor without MSI-H and/or dMMR or with MSI-L, (d) a patient with BRAF V600 wild type malignant melanoma or non-small cell lung cancer, (e) a patient with EGFR gene mutation-negative and/or ALK fusion gene-negative non-small cell lung cancer or (f) a patient with malignant tumor with TMB low frequency.

Furthermore, it can be prescribed as a postoperative adjuvant therapy for preventively suppressing the recurrence or metastasis after surgical resection of malignant tumor or preoperative adjuvant therapy which is performed before surgical resection.

Herein, examples of "other anti-neoplastic drugs" include anti-neoplastic drugs listed in the section [combination and combination preparation] below, those are, alkylating agents, platinum preparations, antimetabolite antagonists (e.g., anti-folates, pyridine metabolism inhibitors and purine metabolism inhibitors), ribonucleotide reductase inhibitors, nucleotide analogs, topoisomerase inhibitors, microtubule polymerization inhibitors, microtubule depolymerization inhibitors, antitumor antibiotics, cytokine preparations, anti-hormonal drugs, molecular targeting drugs, and cancer immunotherapeutic drugs. Furthermore, the sentence "the therapeutic effects of anti-neoplastic drugs are insufficient or not sufficient" means, for example, the case to be still determined as stable (SD) or progression (PD) according to RECIST by even treatment with anti-neoplastic drugs.

[Prescription]

The dosage of the immune checkpoint inhibitor according to the present invention varies depending on age, body weight, symptoms, therapeutic effect, administration method, treatment time and the like, but usually it is orally administered at a range from 1 ng to 1000 mg per dose for an adult once to several times per day, or parenterally administered at a range of 0.1 ng to 100 mg per dose for an adult once to several times a day, or continuously administered intravenously for a period ranging from 30 minutes to 24 hours per day. Of course, as described above, since the dosage varies depending on various conditions, a dosage smaller than the preceding dose may be sufficient, or it may be required to administer it over that range.

For example, if it is the anti-PD-1 antibody, Nivolumab, it is administered with the following usage and dosage, which can be administered to an adult patient at (1) 1 mg/kg (body weight) per dose every 3 weeks, (2) 3 mg/kg (body weight) per dose every 2 weeks, (3) 2 mg/kg (body weight) per dose every 3 weeks, (4) 80 mg per dose every 3 weeks, (5) 240 mg per dose every 2 weeks, (6) 360 mg per dose every 3 weeks or (7) 480 mg per dose every 4 weeks by intravenous drip infusion.

In particular, Nivolumab is administered to a patient with malignant melanoma at 3 mg/kg (body weight) per dose every 2 weeks or 2 mg/kg (body weight) per dose every 3 weeks by intravenous drip infusion, and it is administered to each patient with non-small cell lung cancer, renal cell cancer, classical Hodgkin's lymphoma, head and neck cancer, gastric cancer or malignant pleural mesothelioma at 3 mg/kg (body weight) per dose every 2 weeks by intravenous drip infusion. Furthermore, as another usage and dosage, for example, Nivolumab is administered to each patient with malignant melanoma, non-small cell lung cancer, renal cell carcinoma, urothelial carcinoma, MSI-H or dMMR-positive colorectal cancer, gastric cancer, esophageal cancer, hepatocellular carcinoma, small cell lung cancer or malignant pleural mesothelioma, at 240 mg per dose every 2 weeks or 480 mg per dose 4 weeks, by intravenous drip infusion. Furthermore, as yet another usage and dosage, for example, to a patient with malignant melanoma, in combination with Ipilimumab (at 3 mg/kg (body weight) once a day 4 times every 3 weeks, by intravenous drip infusion), Nivolumab may be administered at 1 mg/kg (body weight) per dose 4 times every 3 weeks followed by being administered at 3 mg/kg (body weight) per dose every 2 weeks, by intravenous drip infusion, or it may be administered at 80 mg per dose 4 times every 3 weeks followed by being administered at 240 mg per dose every 2 weeks or 480 mg per dose every 4 weeks by intravenous drip infusion. In addition, for example, to a patient with renal cell cancer or MSI-H or dMMR-positive colorectal cancer, in combination with Ipilimumab (at 3 mg/kg (body weight) once a day 4 times every 3 weeks, by intravenous drip infusion), Nivolumab may be administered at 240 mg per dose 4 times every 3 weeks, followed by being administered at 240 mg per dose every 2 weeks or 480 mg per dose every 4 weeks by intravenous drip infusion.

If it is Pembrolizumab, which is an anti-PD-1 antibody as well, it can be administered to an adult patient at (1) 200 mg per dose every 3 weeks, (2) 400 mg per dose every 6 weeks, or (3) 2 mg/kg (body weight) (up to 200 mg at a time) per dose every 3 weeks, by intravenous drip infusion. In particular, to each patient with malignant melanoma, non-small cell lung cancer, small cell lung cancer, classical Hodgkin's lymphoma, head and neck cancer, MSI-H solid cancer or colorectal cancer, urothelial carcinoma, cervical cancer, uterine body cancer, primary mediastinal B cell lymphoma, hepatocellular carcinoma, gastric cancer, esophageal cancer or Merkel cell carcinoma, Pembrolizumab is administered at 200 mg per dose every 3 weeks or 400 mg per dose every 6 weeks by intravenous drip infusion. Furthermore, as another usage and dosage, for example, to each patient with classical Hodgkin's lymphoma in children aged 2 years or older, MSI-H solid cancer or colorectal cancer, primary mediastinal B-cell lymphoma or Merkel cell carcinoma, Pembrolizumab is administered at 2 mg/kg (body weight) (up to 200 mg at a time) per dose every 3 weeks by intravenous drip infusion.

If it is Cemiplimab-rwlc, which is an anti-PD-1 antibody as well, it can be administered to an adult patient at 350 mg per dose every 3 weeks, by intravenous drip infusion. In particular, to a patient with spinous cell carcinoma, it is administered at the same usage and dosage.

On the other hand, if it is the anti-PD-L1 antibody, Avelumab, it can be administered to an adult patient at 10 mg/kg (body weight) per dose every 2 weeks by intravenous drip infusion. In particular, to a patient with Merkel cell carcinoma, Avelumab is administered at 10 mg/kg (body weight) per dose every 2 weeks by intravenous drip infusion. Furthermore, to a patient with renal cell carcinoma, in combination with Axitinib, it is administered at the same usage and dosage. If it is Atezolizumab, which is an anti-PD-L1 antibody as well, it is administered to an adult patient at (1) 840 mg per dose every 2 weeks, (2) 1200 mg per dose every 3 weeks or (3) 1680 mg dose every 4 weeks by intravenous drip infusion. In particular, to a patient with non-small cell lung cancer or small cell lung cancer previously treated with chemotherapy or urothelial carcinoma, Atezolizumab is administered at the above usage and dosage, herein, in combination with other anti-neoplastic drugs (Bevacizumab, Paclitaxel and Carboplatin) for a patient with non-small cell lung cancer previously untreated with chemotherapy, or in combination with other anti-neoplastic drugs (Carboplatin and Etoposide) for a patient with small cell lung cancer previously untreated with chemotherapy, it is administered at 1200 mg per dose every 3 weeks. Furthermore, for a patient with triple negative breast cancer, in combination with paclitaxel, Atezolizumab is administered at 840 mg per dose every 2 weeks by intravenous drip infusion.

Furthermore, if it is Durvalumab, which is an anti-PD-L1 antibody as well, to a patient with non-small cell lung cancer or urothelial carcinoma, it is administered at 10 mg/kg (body weight) per dose every 2 weeks by intravenous drip infusion.

If it is the anti-CTLA-4 antibody, Ipilimumab, it is administered to an adult patient at (1) 3 mg/kg (body weight) once a day or (2) 1 mg/kg (body weight) once a day once a day, 4 times every 3 weeks by intravenous drip infusion. In particular, to a patient with malignant melanoma, alone or in combination with Nivolumab, Ipilimumab is administered at 3 mg/kg (body weight) once a day, 4 times every 3 weeks by intravenous drip infusion, and to a patient with renal cell carcinoma or MSI-H colorectal cancer, in combination with Nivolumab, Ipilimumab is administered at 1 mg/kg (body weight) once a day, 4 times every 3 weeks by intravenous drip infusion.

[Combination and Combination Preparation]

In order to (1) suppress the progression of, suppress the recurrence of and/or enhance the therapeutic effect on malignant tumor, (2) decrease the dosage of other combined drugs, and/or (3) reduce the side effects of other combined drugs, the therapeutic agent or the like of the present invention may be used in combination with one or more kinds of other drugs (mainly, anti-neoplastic drug) to be used for the purpose above of treating malignant tumors. In the present invention, the form in which it is prescribed in combination with other drugs may be of a combination preparation which both components are mixed in one preparation or of separated preparations. If administering the therapeutic agent or the like of the present invention and other drugs separately, the therapeutic agent or the like of the present invention may be administered initially followed by administration of other drugs, or other drugs may be administered initially followed by administration of the therapeutic agent or the like of the present invention, and both may be administered simultaneously for a certain period. Furthermore, the administration methods of the respective drugs may be the same or different. Depending on the nature of the drug, it can also be provided as a kit containing the therapeutic agent or the like of the present invention and other drugs. Herein, the dosage of other drugs can be appropriately selected based on a dosage clinically used. Furthermore, other drugs may be administered in combination of two or more kinds of other drugs at an appropriate ratio. In addition, examples of other drugs include those which would be found in the future, as well as those which have been found to date.

Examples of anti-neoplastic drugs, exemplified as a main example of other drugs, include an alkylating drug (e.g., Dacarbazine, Nimustine, Temozolomide, Fotemustine, Bendamustine, Cyclophosphamide, Ifosfamide, Carmustine, Chlorambucil and Procarbazine, etc.), platinum preparation (e.g., Cisplatin, Carboplatin, Nedaplatin and Oxaliplatin, etc.), antimetabolite (e.g., anti-folate (e.g., Pemetrexed, Leucovorin and Methotrexate, etc.), pyridine metabolism inhibitor (e.g., TS-1 (registered trademark), 5-fluorouracil, UFT, Carmofur, Doxifluridine, FdUrd, Cytarabine and Capecitabine, etc.), purine metabolism inhibitor (e.g., Fludarabine, Cladribine and Nelarabine, etc.), ribonucleotide reductase inhibitor, nucleotide analog (e.g., Gemcitabine etc.), topoisomerase inhibitor (e.g., Irinotecan, Nogitecan and Etoposide, etc.), microtubule polymerization inhibitor (e.g., Vinblastine, Vincristine, Vindesine, Vinorelbine and Eribulin, etc.), microtubule depolymerization inhibitor (e.g., Docetaxel and Paclitaxel), antitumor antibiotics (e.g., Bleomycin, Mitomycin C, Doxorubicin, Daunorubicin, Idarubicin, Etoposide, Mitoxantrone, Vinblastine, Vincristine, Peplomycin, Amrubicin, Aclarubicin and Epirubicin, etc.), cytokine preparation (e.g., IFN-α2a, IFN-α2b, Peg IFN-α2b, natural IFN-β and Interleukin-2, etc.), anti-hormonal drug (e.g., Tamoxifen, Fulvestrant, Goserelin, Leuprorelin, Anastrozole, Letrozole and Exemestane, etc.), molecular targeting drug, cancer immunotherapeutic drug, other antibody drugs and the like.

Herein, examples of the molecular targeting drugs include an ALK inhibitor (e.g., Crizotinib, Ceritinib, Ensartinib, Alectinib and Lorlatinib, etc.), BCR-ABL inhibitor (e.g., Imatininib and Dasatinib, etc.), EGFR inhibitor (e.g., Erlotinib, EGF816, Afatinib, Osimertinib mesilate, Gefitinib and Rociletinib, etc.), B-RAF inhibitor (e.g., Sorafenib, Vemurafenib, TAK-580, Dabrafenib, Encorafenib, LXH254, Emurafenib and Zanubrutinib (BGB-3111), etc.), VEGFR inhibitor (e.g., Bevacizumab, Apatinib, Lenvatinib, Aflibercept and Axitinib, etc.), FGFR inhibitor (e.g., AZD4547, Vofatmab (B-701), Roblitinib (FGF401) and Pemigatinib (INCB054828), etc.), c-Met inhibitor (e.g., Savolitinib, Merestinib, Capmatinib, INC280 and Glesatinib, etc.), Axl inhibitor (e.g., ONO-7475 and Bemcentinib (BGB324), etc.), MEK inhibitor (e.g., Cobimetinib, Binimetinib, Selumetinib and Trametinib, etc.), CDK inhibitor (e.g., Dinaciclib, Abemaciclib, Palbociclib and Trilaciclib, etc.), BTK inhibitor (e.g., Ibrutinib and Acalabrutinib, etc.), PI3K-δ/γ inhibitor (e.g., Umbrali sib (TGR-1202), Parsacli sib (INCB050465) and IPI-549, etc.), JAK-1/2 inhibitor (e.g., Itacitinib and Ruxolitinib, etc.), ERK inhibitor (e.g., SCH 900353 etc.), TGFbR1 inhibitor (e.g., Galunisertib etc.), Cancer cell sternness kinase inhibitor (e.g., Amcasertib etc.), FAK inhibitor (e.g., Defactinib etc.), Syk/FLT3 dual inhibitor (e.g., Mivavotinib (TAK-659) etc.), ATR inhibitor (e.g., Ceralasertib (AZD6738) etc.), Weel kinase inhibitor (e.g., Adavosertib (AZD1775) etc.), multi-tyrosine kinase inhibitor (e.g., Sunitinib, Pazopanib, Cabozantinib, Regorafenib, Nintedanib, Sitravatinib and Midostaurin, etc.), mTOR inhibitor (e.g., Temsirolimus, Everolimus, Vistusertib and Irinotecan, etc.), HDAC inhibitor (e.g., Vorinostat, Rominostatin, Entinostat, Chidamide, Mocetinostat, Citarinostat, Panobinostat and Valproate, etc.), PARP inhibitor (e.g., Niraparib, Olaparib, Veliparib, Rucaparib and Beigene-290, etc.), Aromatase inhibitor (e.g., Exemestane and Letrozole, etc.), EZH2 inhibitor (e.g., Tazemestat etc.), Galectin-3 inhibitor (e.g., Belapectin (GR-MD-02) etc.), STAT3 inhibitor (e.g., Napabucasin etc.), DNMT inhibitor (e.g., Azacitidine), BCL-2 inhibitor (e.g., Navitoclax and Venetoclax, etc.), SMO inhibitor (e.g., Vismodegib etc.), Hsp90 inhibitor (e.g., XL888 etc.), γ-tubulin-specific inhibitor (e.g., Glaziovianin A and Plinabulin, etc.), HIF2α inhibitor (e.g., PT2385 etc.), Glutaminase inhibitor (e.g., CB-839 etc.), E3 ligase inhibitor (e.g., Avadomide etc.), Nrf2 activator (e.g., Omaveloxolone etc.), Arginase inhibitor (e.g., CB-1158 etc.), cell cycle inhibitor (e.g., Trabectedin etc.), Ephrin B4 inhibitor (e.g., sEphB4-HAS etc.), IAP antagonist (e.g., Birinapant etc.), anti-Her2 antibody (e.g., Trastuzumab, Trastuzumab emtansine, Trastuzumab beta, Trastuzumab deruxtecan, Trastuzumab duocarmazine, Pertuzumab, Margetuximab, Disitamab, Disitamab vedotin, Gancotamab, Timigutuzumab, Zanidatamab, Zenocutuzumab, R48 and ZW33, etc.), anti-HER1 antibody (e.g., Cetuximab, Panitumumab, Cetuximab sarotalocan, Depatuxizumab, Depatuxizumab mafodotin, Futuximab, Laprituximab, Laprituximab emtansine, Matuzumab, Modotuximab, Petosemtamab, Tomuzotuximab, Losatuximab, Losatuximab vedotin, Serclutamab, Serclutamab talirine, Imgatuzumab, Futuximab, Zalutumumab, Necitumumab and Nimotuzumab etc.), anti-HER3 antibody (e.g., Duligotuzumab, Elgemtumab, Istiratumab, Lumretuzumab, Zenocutuzumab, Patritumab, Patritumab deruxtecan and Seribantumab, etc.), anti-CD 40 antibody (e.g., Bleselumab, Dacetuzumab, Iscalimab, Lucatumumab, Mitazalimab, Ravagalimab, Selicrelumab, Teneliximab, ABBV-428 and APX005M, etc.), anti-CD70 antibody (e.g., Cusatuzumab, Vorsetuzumab, Vorsetuzumab mafodotin and ARGX-110, etc.), anti-VEGF antibody (e.g., Bevacizumab, Bevacizumab beta, Ranibizumab, Abicipar pegol, Aflibercept, Brolucizumab, Convercept, Dilpacimab, Faricimab, Navicixizumab, Varisacumab and IMC-1C11 etc.), anti-VEGFR1 antibody (e.g., Icrucumab etc.), anti-VEGFR2 antibody (e.g., Ramucirumab, Alacizumab, Alacizumab pegol, Olinvacimab, Pegdinetanib and AMG596, etc.), anti-CD20 antibody (e.g., Rituximab, Blontuvetmab, Epitumomab, Ibritumomab tiuxetan, Ocaratuzumab, Ocrelizumab, Technetium ($^{99}$mTc) nofetumomab merpentan, Tositumomab, Veltuzumab, Ofatumumab, Nofetumomab, Ofatumumab, Ublituximab and Obinutuzumab etc.), anti-CD30 antibody (e.g., Brentuximab vedotin and Iratumumab, etc.), anti-CD38 antibody (e.g., Daratumumab, Isatuximab, Mezagitamab, AT13/5 and MOR202, etc.), anti-TNFRSF10B antibody (e.g., Benufutamab, Conatumumab, Drozitumab, Lexatumumab, Tigatuzumab, Eftozanermin alfa and DS-8273a, etc.), anti-TNFRSF10A antibody (e.g., Mapatumumab etc.), anti-MUC1 antibody (e.g., Cantuzumab, Cantuzumab ravtansine, Clivatuzumab, Clivatuzumab tetraxetan, Yttrium ($^{90}$Y) clivatuzumab tetraxetan, Epitumomab, Epitumomab cituxetan, Sontuzumab, Gatipotuzumab, Nacolomab, Nacolomab tafenatox, 7F11C7, BrE-3, CMB-401, CTM01 and HMFG1, etc.), anti MUC5AC antibody (e.g., Ensituxumab etc.), anti-MUC16 antibody (e.g., Oregovomab, Abagovomab, Igovomab, and Sofituzumab vedotin, etc.), anti-DR5 antibody (e.g., DS-8273a etc.), anti-CA125 antibody (e.g., Oregovomab etc.), anti-DLL4 antibody (e.g., Demcizumab, Dilpacimab, Navicixizumab and Enoticumab, etc.), anti-fucosyl GM1 antibody (e.g., BMS-986012 etc.), anti-gpNMB antibody (e.g., Glembatumumab vedotin etc.), anti-Mesothelin antibody (e.g., Amatuximab, Anetumab ravtansine, Anetumab corixetan, RG7784 and BMS-986148, etc.), anti-MMP9 antibody (e.g., Andecaliximab etc.), anti-GD2 antibody (e.g., Dinutuximab, Dinutuximab beta, Lorukafusp alfa, Naxitamab, 14G2a, MORAb-028, Surek, TRBs07 and ME361, etc.), anti-c-Met antibody (e.g., Emibetuzumab, Onartuzumab, Telisotuzumab and Telisotuzumab vedotin, etc.), anti-FOLR1 antibody (e.g., Farletuzumab, Mirvetuximab and Mirvetuximab soravtansine, etc.), anti-CD79b antibody (e.g., Iladatuzumab, Iladatuzumab vedotin, and Polatuzumab vedotin, etc.), anti-DLL3 antibody (e.g., Rovalpituzumab and Rovalpituzumab tesirine, etc.), anti-CD51 antibody (e.g., Abituzumab, Etaracizumab and Intetumumab, etc.), anti-EPCAM antibody (e.g., Adecatumumab, Catumaxomab, Edrecolomab, Oportuzumab monatox, Citatuzumab bogatox and Tucotuzumab celmoleukin, etc.), anti-CEACAM5 antibody (e.g., Altumomab, Arcitumomab, Cergutuzumab amunaleukin, Labetuzumab, Labetuzumab govitecan, $^{90}$Y-cT84.66, AMG211, BW431/26, CE25/B7, COL-1 and T84.66 MSA, etc.), anti-CEACAM6 antibody (e.g., Tinurilimab etc.), anti-FGFR2 antibody (e.g., Aprutumab, Aprutumab ixadotin and Bemarituzumab, etc.), anti-CD44 antibody (e.g., Bivatuzumab mertansine etc.), anti-PSMA antibody (e.g., Indium ($^{111}$In) capromab pendetide, $^{177}$Lu-J591 and ES414, etc.), anti-Endoglin antibody (e.g., Carotuximab etc.), anti-IGF1R antibody (e.g., Cixutumumab, Figitumumab, Ganitumab, Dalotuzumab, Teprotumumab and Robatumumab, etc.), anti-TNFSF11 antibody (e.g., Denosumab etc.), anti-GUCY2C antibody (e.g., Indusatumumab vedotin etc.), anti-SLC39A6 antibody (e.g., Ladiratuzumab vedotin etc.), anti-SLC34A2 antibody (e.g., Lifastuzumab vedotin etc.), anti-NCAM1 antibody (e.g. Lorvotuzumab mertansine and N901, etc.), anti-ganglioside GD3 antibody (e.g. Ecromeximab and Mitumomab, etc.), anti-AMHR2 antibody (e.g. Murlentamab etc.), anti-CD37 antibody (e.g. Lilotomab, Lutetium ($^{177}$lu) lilotomab satetraxetan, Naratuximab, Naratuximab emtansine and Otlertuzumab, etc.), anti-IL1RAP antibody (e.g., Nidanilimab etc.), anti-PDGFR2 antibody (e.g., Olaratumab and Tovetumab, etc.), anti-CD200 antibody (e.g., Samalizumab etc.), anti-TAG-72 antibody (e.g., Anatumomab mafenatox, Minretumomab, Indium ($^{111}$In) satumomab pendetide, CC49, HCC49, and M4, etc.), anti-SLITRK6 antibody (e.g., Sirtratumab vedotin etc.), anti-DPEP3 antibody (e.g., Tamrintamab pamozirine etc.), anti-CD19 antibody (e.g. Axicabtagene ciloleucel, Coltuximab ravtansine, Denintuzumab mafodotin, Inebilizumab, Loncastuximab, Loncastuximab tesirine, Obexelimab Tafasitamab, Taplitumomab paptox and huAnti-B4, etc.), anti-NOTCH2/3 antibody (e.g., Tarextumab etc.), anti-tenascin C antibody (e.g., Tenatumomab etc.), anti-AXL antibody (e.g., Enapotamab, Enapotamab vedotin, and Tilvestamab, etc.), anti-STEAP1 antibody (e.g., Vandortuzumab vedotin etc.), anti-CTAA16 antibody (e.g., Technetium ($^{99}$mTc) votumumab etc.), anti-CLDN18 antibody (e.g., Zolbetuximab etc.), anti-GM3 antibody (e.g., Racotumomab, FCGR1 and H22, etc.), anti-PSCA antibody (e.g., MK-4721 etc.), anti-FN extra domain B antibody (e.g., AS1409 etc.), anti-HAVCR1 antibody (e.g., CDX-014 etc.), anti-TNFRSF4 antibody (e.g., MEDI6383 etc.), anti-FAP antibody/IL-2 fusion protein (e.g., RO6874281), anti-CEA antibody/IL-2 fusion protein (e.g., Cergutuzumab amunaleukin), anti-HER1-MET bispecific antibody (e.g., Amivantamab etc.), anti-HER1-MET bispecific antibody (e.g., Amivantamab etc.), anti-EPCAM-CD3 bispecific antibody (e.g., Solitomab and Catumaxomab), anti-Ang2-VEGF bispecific antibodies (e.g., Vanucizumab), anti-HER2-CD3 bispecific antibody (e.g., Ertumaxomab), anti-HER3-IGF1R bispecific antibody (e.g., Istiratumab), anti-PMSA-CD3 bispecific antibody (e.g., Pasotuximab), anti-HER1-LGR5 bispecific antibody (e.g., Petosemtamab), anti-SSTR2-CD3 bispecific antibody (e.g., Tidutamab), anti-CD30-CD16A bispecific antibody (e.g., AFM13 etc.), anti-IL3RA-CD3 bispecific antibody (e.g., Flotetuzumab and Vibecotamab), anti-GPRC5D-CD3 bispecific antibody (e.g., Talquetamab), anti-TNFRSF17-CD3 bispecific antibody (e.g., Teclistamab), anti-CLEC12A-CD3 bispecific antibody (e.g., Tepoditamab), anti-HER2-HER3 bispecific antibody (e.g., Zenocutuzumab), anti-CEA-CD3 bispecific antibody (e.g., Cibisatamab and RO6958688), anti-CD3-CD19 bispecific antibody (e.g., Duvortuxizumab and Blinatumomab, etc.), anti-CD20-CD3 bispecific antibody (e.g., Plamotamab, Odronextamab, Mosunetuzumab, Glofitamab, Epcoritamab and REGN 1979, etc.) and the like.

Furthermore, examples of the cancer immunotherapeutic drugs include an anti-PD-1 antibody (e.g., Nivolumab, Cemiplimab (REGN-2810), Penbrolizumab (MK-3475), Spartalizumab (PDR-001), Tislelizumab (BGB-A317), AMP-514 (MEDI0680), Dostarlimab (ANB011/TSR-042), Toripalimab (JS001), Camrelizumab (SHR-1210), Genolimzumab (CBT-501), Sintilimab (IBI308), Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM 388D4, ENUM 244C8, GLS1010, CS1003, BAT-1306, AK103, BI 754091, LZM009, CMAB819, Sym021, SSI-361, JY034, HX008, ISU106 and CX-188, etc.), anti-PD-L1 antibody (e.g., Atezolizumab (RG7446/MPDL3280A), Avelumab (PF-06834635/MSB0010718C), Durvalumab (MEDI4736), Manelimab, Pacmilimab, Envafolimab, Cosibelimab, BMS-936559, STI-1014, HLX20, SHR-1316, CS1001 (WBP3155), MSB2311, BGB-A333, KL-A167, AK106, AK104, ZKAB001, FAZ053, CBT-502 (TQB2450) and JS003, etc.), PD-1 antagonist (e.g., AUNP-12, each compound of BMS-M1 to BMS-M10, BMS-1, BMS-2, BMS-3, BMS-8, BMS-37, BMS-200, BMS-202, BMS-230, BMS-242, BMS-1001, BMS-1166, each compound of Incyte-1 to Incyte-6, each compound of CAMC-1 to CAMC-4, RG_1 and DPPA-1, etc.), PD-L1/VISTA antagonist (e.g., CA-170), PD-L1/TIM3 antagonist (e.g., CA-327), anti-PD-L2 antibody, PD-L1 fusion protein, PD-L2 fusion protein (e.g., AMP-224 etc.), anti-CTLA-4 antibody (e.g., Ipilimumab (MDX-010), Nurulimab, Zalifrelimab (AGEN1884) and Tremelimumab, etc.), anti-LAG-3 antibody (e.g., Relatlimab (BMS-986016/ONO-4482), Encelimab, Ieramilimab (LAG525), Fianlimab (REGN3767), and Mavezelimab (MK-4280), etc.), LAG fusion protein (e.g., IMP321 etc.), anti-Tim3 antibody (e.g., MBG453 and Cobolimab (TSR-022), etc.), anti-KIR antibody (e.g., Lirilumab (BMS-986015/ONO-4483), IPH2101, LY3321367 and MK-4280, etc.), anti-BTLA antibody, anti-TIGIT antibody (e.g., Tiragolumab, Etigilimab, Vibostolimab (MTIG-7192A/RG-6058/RO-7092284) and BMS-986207 (ONO-4686)), anti-VISTA antibody (e.g., Onvatilimab (JNJ-61610588) etc.), anti-CD137 antibody (e.g., Urelumab (ONO-4481/BMS-663513) and Utomilumab (PF-05082566), etc.), anti-CSF-1R antibody or CSF-1R inhibitor (e.g., Cabiralizumab (FPA008/BMS-986227/ONO-4687), Ecactuzumab (RG7155/RO5509554), LY3022855, Axatilimab, MCS-110, IMC-CS4, AMG820, Pexidartinib, BLZ945 and ARRY-382, etc.), anti-OX40 antibody (e.g., MEDI 6469, Ivuxolimab (PF-04518600), MEDI0562, MEDI6383, Efizonerimod, GSK3174998, BMS-986178 and MOXR0916, etc.), anti-HVEM antibody, anti-CD27 antibody (e.g., Varlilumab (CDX-1127) etc.), anti-GITR antibody or GITR fused protein (e.g., Efaprinermin alfa, Efgivanermin alfa, MK-4166, INCAGN01876, GWN323 and TRX-518, etc.), anti-CD28 antibody, anti-CCR4 antibody (e.g., Mogamulizumab etc.), anti-B7-H3 antibody (e.g., Enoblituzumab, Mirzotamab, Mirzotamab clezutoclax and Omburtamab, etc.), anti-ICOS agonist antibody (e.g., Vopratelimab (JTX-2011) and GSK3359609, etc.), anti-CD4 antibody (e.g., MTRX-1011A, TRX-1, Ibalizumab, huB-F5, Zanolimumab, 4162W94, Clenoliximab, Keliximab, AD-519, PRO-542, Cedelizumab, TNX-355, Dacetuzumab, Tregalizumab, Priliximab, MDX-CD4, CAMPATH-9 and IT1208, etc.), anti-DEC-205 antibody/NY-ESO-1 fusion protein (e.g., CDX-1401 etc.), anti-SLAMF7 antibody (e.g., Azintuxizumab, Azintuxizumab vedotin and Elotuzumab, etc.), anti-CD73 antibody (e.g., Oleclumab and BMS-986179, etc.), pegylated IL-2 (e.g., Bempegaldesleukin (NKTR-214) etc.), anti-CD40 agonist antibody (e.g., ABBV-428, APX005M and RO7009789, etc.), IDO inhibitor (e.g., Epacadostat, Indoximod and BMS-986205, etc.), TLR agonist (e.g., Motolimod, CMP-001, G100, Tilsotolimod (IMO-2125), SD-101 and MEDI9197, etc.), adenosine A2A receptor antagonist (e.g., Preladenant, AZD4635, PBF 509 and CPI-444, etc.), anti-NKG2A antibody (e.g., Monalizazumab etc.), anti-CSF-1 antibody (e.g., PD0360324 etc.), immunopotentiating agent (e.g., PV-10 etc.), IL-15 superagonist (e.g., ALT-803 etc.), soluble LAG3 (e.g., Eftilagimod alpha (IMP 321) etc.), anti-CD47 antibody or CD47 antagonist (e.g., ALX148 etc.), IL-12 antagonist (e.g., M9241 etc.) and the like.

Furthermore, examples of other antibody drugs include an anti-IL-1β antibody (e.g., Canakinumab etc.), anti-CCR2 antibody (e.g., Plozalizumab etc.) and the like.

[Formulation]

When the immune checkpoint inhibitory substance or immune checkpoint inhibitor of the present invention is administered alone or in combination with other drugs, it is used in form of solid preparation or liquid preparation for oral administration, sustained-release preparation or controlled-release preparation for oral administration, or injection, external preparation, inhalant, suppository or the like for parenteral administration.

Examples of the solid preparation for oral administration include tablets, pills, capsules, powders, granules and the like, and examples of the capsules include hard capsules, soft capsules and the like.

In case of the solid preparation, the immune checkpoint inhibitory substance of the present invention may be used as it is or by mixing with any one of an excipient (e.g., lactose, mannitol, glucose, microcrystalline cellulose and starch, etc.), binder (e.g., hydroxylpropylcellulose, polyvinylpyrrolidone and magnesium aluminometasilicate, etc.), disintegrant (e.g., calcium fibrin glycolate etc.), lubricant (e.g., magnesium stearate etc.), stabilizer, solubilizer (e.g., glutamic acid and aspartic acid, etc.) and the like so as to be formulated according to conventional methods. If necessary, it may be coated with a coating agent (e.g., sucrose, gelatin, hydroxypropylcellulose and hydroxypropylmethylcellulose phthalate, etc.), or may be coated with two or more layers. Further, it may also be contained in a capsule made of a substance which is easily absorbed by the body, such as gelatin.

The liquid preparation for oral administration may contain, if necessary, any one or more of kinds of pharmaceutically acceptable aqueous solution, suspension, emulsion, syrup, elixir and the like. Furthermore, this liquid preparation may further contain any one or more of kinds of a wetting agent, sweetening agent, flavoring agent, aromatic agent, preservative, buffering agent or the like.

The sustained-release preparation for oral administration may contain may also contain a binder and thickener, in addition to a sustained-release base agent, and examples of thereof include a gum arabic, agar, polyvinylpyrrolidone, sodium alginate, propylene glycol alginate, carboxyvinyl polymer, carboxymethyl cellulose, sodium carboxymethyl cellulose, guar gum, gelatin, hydroxypropyl methyl cellulose, hydroxypropyl cellulose, polyvinyl alcohol, methyl cellulose, hydroxyethyl methyl cellulose or the like.

If using the injection or transfusion for drip infusion, the injection or transfusion may be in any form of aqueous solution, suspension or emulsion, and may be formulated as a solid formulation with a pharmaceutically acceptable carrier so that it can be dissolved, suspended or emulsified by adding a solvent when needed. As a solvent which is used in the injection or transfusion for drip infusion, for example, distilled water for injection, physiological saline, glucose solution and isotonic solution (e.g., a solution of sodium chloride, potassium chloride, glycerin, mannitol, sorbitol, boric acid, borax or propylene glycol, etc.), and the like can be used.

Herein, examples of the "pharmaceutically acceptable carrier" include a stabilizer, solubilizer, suspending agent, emulsifier, soothing agent, buffer, preservative, antiseptic agent, pH adjuster, antioxidant and the like. As the stabilizer, for example, various amino acids, albumin, globulin, gelatin, mannitol, glucose, dextran, ethylene glycol, propylene glycol, polyethylene glycol, ascorbic acid, sodium hydrogen sulfite, sodium thiosulfate, sodium edetate, sodium citrate, dibutylhydroxytoluene or the like can be used. As the solubilizer, for example, alcohol (e.g., ethanol etc.), polyalcohol (e.g., propylene glycol and polyethylene glycol, etc.), nonionic surfactant (e.g., Polysorbate 20 (registered trademark), Polysorbate 80 (registered trademark) and HCO-50, etc.), etc.) or the like can be used. As the suspending agent, for example, glyceryl monostearate, aluminium monostearate, methyl cellulose, carboxymethyl cellulose, hydroxymethyl cellulose, sodium lauryl sulfate or the like can be used. As the emulsifier, for example, gum arabic, sodium alginate, tragacanth or the like can be used. As the soothing agent, for example, benzyl alcohol, chlorobutanol, sorbitol or the like can be used. As the buffer, phosphate buffer, acetate buffer, borate buffer, carbonate buffer, citrate buffer, Tris buffer, glutamate buffer, epsilon aminocaproate buffer or the like can be used. As the preservative, for example, methyl paraoxybenzoate, ethyl paraoxybenzoate, propyl paraoxybenzoate, butyl paraoxybenzoate, chlorobutanol, benzyl alcohol, benzalkonium chloride, dehydro sodium acetate, sodium edetate, boric acid, borax or the like can be used. As the antiseptic agent, for example, benzalkonium chloride, paraoxybenzoic acid, chlorobutanol or the like can be used. As the pH adjuster, for example, hydrochloric acid, sodium hydroxide, phosphoric acid, acetic acid or the like can be used. As the antioxidant, for example, (1) a water-soluble antioxidant such as ascorbic acid, cysteine hydrochloride, sodium bisulfate, sodium metabisulfite, sodium sulfite and the like, (2) an oil-soluble antioxidant such as ascorbyl palmitate, butylated hydroxyanisole, butylated hydroxytoluene, lecithin, propyl gallate, α-tocopherol and the like, or (3) a metal chelating agent such as citric acid, ethylenediaminetetraacetic acid, sorbitol, tartaric acid, phosphoric acid and the like can be used.

The injection or transfusion for drip infusion can be produced by sterilizing it at the final step or by aseptic operation methods, for example, filtering with a filter or the like, followed by filling a sterile container. Alternatively, the injection or transfusion for drip infusion may be used by dissolving a sterile powder obtained by vacuum drying and freeze-drying (which may contain a powder of pharmaceutically acceptable carrier) in a suitable solvent before use.

The external preparation for parenteral administration can be used in a form of a propellant, inhalant, spray, aerosol, ointment, gel, cream, poultice, patch, liniment, nasal drop or the like, which is prepared by publically known methods or in usually used formulation.

The propellant, inhalant and spray may contain a stabilizer such as sodium bisulfite, other than commonly used diluents and buffer giving isotonicity, for example, an isotonic agent such as sodium chloride, sodium citrate and citric acid. The method for producing the spray is described in, for example, U.S. Pat. Nos. 2,868,691 and 3,095,355, in detail.

Examples of the inhalants include an aerosol agent, inhalant powder or inhalant liquid, and the inhalant liquid may be used in a form of being dissolved or suspended in water or other appropriate mediums before use.

These inhalants can be manufactured according to publically known methods, for example, if it is an inhalant liquid, it can be prepared by appropriately selecting a preservative (e.g., benzalkonium chloride and paraben, etc.), coloring agent, buffer (e.g., sodium phosphate and sodium acetate, etc.), isotonicity agent (e.g., sodium chloride and concentrated glycerin, etc.), thickener (e.g., carboxyvinyl polymer etc.), absorption enhancer or the like, if necessary. If it is an inhalant powder, it can be prepared by appropriately selecting a lubricant (e.g., stearic acid and salt thereof, etc.), binder (e.g., starch and dextrin, etc.), excipient (e.g., lactose and cellulose, etc.), coloring agent, preservative (e.g., benzalkonium chloride and paraben, etc.), absorption enhancer or the like, if necessary.

When administering the inhalant liquid, a nebulizer (e.g., atomizer and nebulizer, etc.) is usually used while when administering the inhalant powder, an inhaler for a powdered medicine is usually used.

The ointment is prepared in a publically known or commonly used formulation, for example, can be prepared by mixing or melting the immune checkpoint inhibitory substance of the present invention in base. An ointment base can be selected from publically known or commonly used ones, which is used by mixing with, for example, one or more kinds selected from a higher fatty acid or higher fatty acid ester (e.g., adipic acid, myristic acid, palmitic acid, stearic acid, oleic acid, adipic acid ester, myristic acid ester, palmitic acid ester, stearic acid ester and oleic acid ester, etc.), waxes (e.g., beeswax, whale wax and ceresin, etc.), surfactant (e.g., polyoxyethylene alkyl ether phosphate etc.), higher alcohol (e.g., cetanol, stearyl alcohol and cetostearyl alcohol, etc.), silicone oil (e.g., dimethyl polysiloxane etc.), hydrocarbons (e.g., hydrophilic petrolatum, white petrolatum, purified lanolin and liquid paraffin, etc.), glycols (e.g., ethylene glycol, diethylene glycol, propylene glycol, polyethylene glycol and macrogol, etc.), vegetable oil (e.g., castor oil, olive oil, sesame oil and turpentine oil, etc.), animal oil (e.g., mink oil, egg yolk oil, squalane and squalene, etc.), water, absorption promoter and anti-rash agent. Furthermore, it may contain a moisturizing agent, preservative, stabilizer, antioxidant, flavoring agent or the like.

The gel is prepared in a publically known or commonly used formulation, for example, can be prepared by melting the immune checkpoint inhibitory substance of the present invention in base. A gel base is selected from publically known or commonly used ones, which is used by mixing with, for example, one or more kinds selected from a lower alcohol (e.g., ethanol and isopropyl alcohol, etc.), gelling agent (e.g., carboxymethyl cellulose, hydroxyethyl cellulose, hydroxypropyl cellulose and ethyl cellulose, etc.), neutralizing agent (e.g., triethanolamine and diisopropanolamine, etc.), surfactant (e.g., polyethylene glycol monostearate etc.), gums, water, absorption promoter and anti-rash agent. Furthermore, it may contain a preservative, antioxidant, flavoring agent or the like.

The cream is prepared in a publically known or commonly used formulation, for example, can be prepared by melting or emulsifying the immune checkpoint inhibitory substance of the present invention in base. A cream base is selected from publically known or commonly used ones, which is used by mixing with, for example, one or more kinds selected from a higher fatty acid ester, lower alcohol, hydrocarbons, polyhydric alcohol (e.g., propylene glycol and 1,3-butylene glycol, etc.), higher alcohol (e.g., 2-hexyldecanol and cetanol, etc.), emulsifier (e.g., polyoxyethylene alkyl ethers and fatty acid esters, etc.), water, absorption promoter and anti-rash agent. Furthermore, it may contain a preservative, antioxidant, flavoring agent or the like.

The poultice is prepared in a publically known or commonly used formulation, for example, can be prepared by melting the immune checkpoint inhibitory substance of the present invention in base and spreading and coating it on a support as a kneaded product. A poultice base is selected from publically known or commonly used ones, which is used by mixing with, for example, one or more kinds selected from a thickener (e.g., polyacrylic acid, polyvinylpyrrolidone, arabic gum, starch, gelatin and methylcellulose, etc.), wetting agent (e.g., urea, glycerin and propylene glycol, etc.), filler (e.g., kaolin, zinc oxide, talc, calcium and magnesium, etc.), water, solubilizing agent, tackifier and anti-rash agent. Furthermore, it may contain a preservative, antioxidant, flavoring agent or the like.

The patch is prepared in a publically known or commonly used formulation, for example, can be prepared by melting the immune checkpoint inhibitory substance of the present invention in base and spreading and coating it on a support. A patch base is selected from publically known or commonly used ones, which is used by mixing with, for example, one or more kinds selected from a polymer base, fats and oils, higher fatty acid, tackifier and anti-rash agent. Furthermore, it may contain a preservative, antioxidant, flavoring agent or the like.

The liniment is prepared in a publically known or commonly used formulation, for example, can be prepared by dissolving, suspending or emulsifying the immune checkpoint inhibitory substance of the present invention in one or more kinds selected from water, an alcohol (e.g., ethanol and polyethylene glycol, etc.), higher fatty acid, glycerin, soap, emulsifier, suspending agent and the like. Furthermore, it may contain a preservative, antioxidant, flavoring agent or the like.

Examples of other compositions for parenteral administration include a suppository for rectal administration and pessary for vaginal administration which contain the immune checkpoint inhibitor of the present invention and are prescribed by conventional methods.

[Test and Measurement Kits]

The present invention also includes inventions regarding test or assay kits for measuring the evaluation items constituting Biomarkers 1 to 10 of the present invention, respectively. The test or assay kit may be based on, for example, flow cytometry in case of measuring the respective MFIs of PD-1 expressions in $CD8^+$ T cells, $CD3^+$ T cells, $Foxp3^+$ T cells, Treg cells (Fr. II) and Treg cells (Fr. III) whereas it may be based on flow cytometry or immunostaining, in case of measuring the respective numbers of $CD8^+$ T cells, $CD4^+$ T cells, $Foxp3^+$ T cells, Treg cells (Fr. II) and Treg cells (Fr. III) and the number of PD-1 expressing cells thereamong, as well as the number of CCR7 expressing $CD8^+$ T cells. In all cases, flow cytometry-based test or assay kits are preferred.

The contents of all patent documents and non-patent documents or references explicitly cited in the present specification may be incorporated herein as a part of the present specification.

The present invention will be described in more detail by the following examples, but the scope of the present invention is not limited thereto. A person skilled in the art can make various changes and modifications, based on the description of the present invention, and such changes and modifications are also included in the present invention.

EXAMPLES

Example 1: Verification of the Biomarker for Determining the Efficacy of Nivolumab, Based on the Percentage (%) of CCR7 Expressing Cells Among $CD8^+$ T Cells and the Ratio of the Respective MFIs of PD-1 Expressions in $CD8^+$ T Cells and $Foxp3^+$ T Cells (Biomarker 1)

The number of CCR7 expressing cells among $CD8^+$ T cells and the respective PD-1 expressions in the $CD8^+$ T cells and Foxp3$^+$ T cells, derived from tumor tissues of patients with gastric cancer (29 cases) and patients with non-small cell lung cancer (16 cases), before administration of Nivolumab were measured by flow cytometry, and the percentage (%) of CCR7 expressing cells among the CD8$^+$ T cells and the ratio of the MFI of PD-1 expression in the CD8$^+$ T cells to the MFI of PD-1 expression in the Foxp3$^+$ T cells were calculated, respectively.

Among the above patients to which Nivolumab was administered according to the prescribed prescription, the Responder group (23 patients in which PFS was maintained for 70 days) and Non-Responder group (22 patients in which PFS was less than 70 days) were plotted on a graph with the percentage (%) of CCR7 expressing cells in each patient thereof on the vertical axis and the square root of the ratio on the horizontal axis (see FIG. 1), respectively.

Three solid lines in the figure represent classification lines derived by machine learning using the weighted f-measure (f$\alpha$) as an indicator so that the value of f$\alpha$ becomes maximized when the $\alpha$ value is 0.5, and it was confirmed that if Nivolumab is hypothetically administered to the 22 patients with tumor plotted in the closed, shaded area on the right side of the figure, separated by the classification lines, 20 thereamong (efficacy rate: 90.9%) would be expected to benefit therefrom.

Example 2: Verification of the Biomarker for Determining the Efficacy of Nivolumab, Based on the Respective Percentages (%) of PD-1 Expressing Cells Among Treg Cells (Fr.III) and CD8$^+$ T Cells (Biomarker 2)

The respective PD-1-expressions among Treg cells (Fr.III) and CD8$^+$ T cells, derived from tumor tissues of patients with gastric cancer (29 cases) and patients with non-small cell lung cancer (17 cases), before administration of Nivolumab were measured by flow cytometry, and the percentages (%) of PD-1-expressions among those cells were calculated, respectively.

Among the above patients to which Nivolumab was administered according to the prescribed prescription, the Responder group (23 patients) and Non-Responder group (23 patients) (both groups are defined in the same way as that in Example 1) were plotted on a graph with the percentage (%) of PD-1 expressing cells among the Treg cells (Fr.III) in each patient thereof on the vertical axis and the percentages (%) of PD-1 expressing cells among the CD8$^+$ T cells on the horizontal axis (see FIG. 2), respectively.

Two solid lines in the figure represent classification lines derived by the same machine learning as above, and it was confirmed that if Nivolumab is hypothetically administered to the 27 patients with tumor plotted in the closed, shaded area on the upper left and lower right side of the figure, separated by the classification lines, 22 thereamong (efficacy rate: 81.5%) would be expected to benefit therefrom.

Example 3: Verification of the Biomarker for Determining the Efficacy of Nivolumab, Based on the Number of PD-1 Expressing Cells Among CD8$^+$ T Cells and the Ratio of the Respective MFIs of PD-1 Expressions in Foxp3$^+$ T Cells and CD8$^+$ T Cells (Biomarker 3)

The number of PD-1 expressing cells among CD8$^+$ T cells and the PD-1 expressions in Foxp3$^+$ T cells and CD8$^+$ T cells, derived from tumor tissues of patients with gastric cancer (29 cases) and patients with non-small cell lung cancer (17 cases), before administration of Nivolumab were measured by flow cytometry, and the ratio of the MFI of PD-1 expression in the CD8$^+$ T cells to the MFI of PD-1 expression in the Foxp3$^+$ T cells was calculated.

Among the above patients to which Nivolumab was administered according to the prescribed prescription, the Responder group (23 patients) and Non-Responder group (23 patients) (both groups are defined in the same way as that in Example 1) were plotted on a graph with the common logarithm of the value given by adding 1 to the number of PD-1 expressing cells in each patient thereof on the vertical axis and the square root of the ratio on the horizontal axis (see FIG. 3), respectively.

Two solid lines in the figure represent classification lines derived by the same machine learning as above, and it was confirmed that if Nivolumab is hypothetically administered to the 22 patients with tumor plotted in the closed, shaded area, except for that on the lower left side of the figure, separated by the classification lines, 19 thereamong (efficacy rate: 86.4%) would be expected to benefit therefrom.

Example 4: Verification of the Biomarker for Determining the Efficacy of Nivolumab, Based on the Ratio of the MFIs of PD-1 Expressions in Foxp3$^+$ T Cells and CD8$^+$ T Cells and the Percentage (%) of PD-1 Expressing Cells Among CD8$^+$ T Cells (Biomarker 4)

The PD-1 expressions in CD8$^+$ T cells and Foxp3$^+$ T cells, derived from tumor tissues of patients with gastric cancer (29 cases) and patients with non-small cell lung cancer (17 cases), before administration of Nivolumab were measured by flow cytometry, respectively, and the ratio of the MFI of PD-1 expression in the CD8$^+$ T cells to the MFI of PD-1 expression in the Foxp3$^+$ T cells and the percentage (%) of PD-1 expressing cells among the CD8$^+$ T cells were calculated, respectively.

Among the above patients to which Nivolumab was administered according to the prescribed prescription, the Responder group (23 patients) and Non-Responder group (23 patients) (both groups are defined in the same way as that in Example 1) were plotted on a graph with the square root of the ratio in each patient thereof on the vertical axis and the percentage (%) on the horizontal axis (see FIG. 4), respectively.

Two solid lines in the figure represent classification lines derived by the same machine learning as above, and it was confirmed that if Nivolumab is hypothetically administered to the 22 patients with tumor plotted in the closed, shaded area, except for that on the lower left side of the figure, separated by the classification lines, 18 thereamong (efficacy rate: 81.8%) would be expected to benefit therefrom.

Example 5: Verification of the Biomarker for Determining the Efficacy of Nivolumab, Based on the Respective Percentages (%) of PD-1 Expressing Cells Among Foxp3$^+$ T Cells and CD8$^+$ T Cells (Biomarker 5)

The PD-1 expressions in Foxp3$^+$ T cells and CD8$^+$ T cells, derived from tumor tissues of patients with gastric cancer (29 cases) and patients with non-small cell lung cancer (17 cases), before administration of Nivolumab were measured by flow cytometry, respectively, and the percentages (%) of PD-1 expressing cells were calculated, respectively.

Among the above patients to which Nivolumab was administered according to the prescribed prescription, the Responder group (23 patients) and Non-Responder group (23 patients) (both groups are defined in the same way as that in Example 1) were plotted on a graph with the percentage (%) of PD-1 expressing cells among the Foxp3$^+$ T cells in each patient thereof on the vertical axis and the percentage (%) of PD-1 expressing cells among the CD8$^+$ T cells on the horizontal axis (see FIG. 5), respectively.

A solid line in the figure represent a classification line derived by the same machine learning as above, and it was confirmed that if Nivolumab is hypothetically administered to the 28 patients with tumor plotted in the shaded area on the right side of the figure, separated by the classification line, 21 thereamong (efficacy rate: 75%) would be expected to benefit therefrom.

Example 6: Verification of the Biomarker for
Determining the Efficacy of Nivolumab, Based on
the Respective Percentages (%) of PD-1 Expressing
Cells Among Treg Cells (Fr.II) and CD8$^+$ T Cells
(Biomarker 6)

The PD-1 expressions in Treg cells (Fr.II) and CD8$^+$ T cells, derived from tumor tissues of patients with gastric cancer (29 cases) and patients with non-small cell lung cancer (17 cases), before administration of Nivolumab were measured by flow cytometry, respectively, and the percentages (%) of PD-1 expressing cells were calculated, respectively.

Among the above patients to which Nivolumab was administered according to the prescribed prescription, the Responder group (23 patients) and Non-Responder group (23 patients) (both groups are defined in the same way as that in Example 1) were plotted on a graph with the percentage (%) of PD-1 expressing cells among the Treg cells (Fr.II) in each patient thereof on the vertical axis and the percentage (%) of PD-1 expressing cells among the CD8$^+$ T cells on the horizontal axis (see FIG. 6), respectively.

Two solid lines in the figure represent classification lines derived by the same machine learning as above, and it was confirmed that if Nivolumab is hypothetically administered to the 22 patients with tumor plotted in the shaded area on the upper left and lower right side of the figure, separated by the classification lines, 19 thereamong (efficacy rate: 86.4%) would be expected to benefit therefrom.

Example 7: Verification of the Biomarker for
Determining the Efficacy of Nivolumab, Based on
the Respective Percentages (%) of PD-1 Expressing
Cells Among CD4$^+$ T Cells and CD8$^+$ T Cells
(Biomarker 7)

The PD-1 expressions in CD4$^+$ T cells and CD8$^+$ T cells, derived from tumor tissues of patients with gastric cancer (29 cases) and patients with non-small cell lung cancer (18 cases), before administration of Nivolumab were measured by flow cytometry, respectively, and the percentages (%) of PD-1 expressing cells were calculated, respectively.

Among the above patients to which Nivolumab was administered according to the prescribed prescription, the Responder group (24 patients) and Non-Responder group (23 patients) (both groups are defined in the same way as that in Example 1) were plotted on a graph with the percentage (%) of PD-1 expressing cells among the CD4$^+$ T cells in each patient thereof on the vertical axis and the percentage (%) of PD-1 expressing cells among the CD8$^+$ T cells on the horizontal axis (see FIG. 7), respectively.

Two solid lines in the figure represent classification lines derived by the same machine learning as above, and it was confirmed that if Nivolumab is hypothetically administered to the 29 patients with tumor plotted in the shaded area, except for that on the upper left side of the figure, separated by the classification lines, 22 thereamong (efficacy rate: 75.9%) would be expected to benefit therefrom.

Example 8: Verification of the Biomarker for
Determining the Efficacy of Nivolumab, Based on
the Ratio of the Respective MFIs of PD-1
Expressions in Treg Cells (Fr. II) and CD3$^+$ T Cells
and the Percentage (%) of PD-1 Expressing Cells
Among CD4$^+$ T Cells (Biomarker 8)

The respective PD-1 expressions in Foxp3$^+$ T cells, Treg cells (Fr.II) and CD4$^+$ T cells derived from tumor tissues of patients with gastric cancer (29 cases) and patients with non-small cell lung cancer (18 cases), before administration of Nivolumab were measured by flow cytometry, and the ratio of the MFI of PD-1 expression in the CD3$^+$ T cells to the MFI of PD-1 expression in the Treg cells (Fr.II) and the percentage (%) of PD-1 expressing cells among the CD4$^+$ T cells were calculated, respectively.

Among the above patients to which Nivolumab was administered according to the prescribed prescription, the Responder group (22 patients which were diagnosed as CR, PR or SD) and Non-Responder group (25 patients which were diagnosed as PD) were plotted on a graph with the square root of the ratio in each patient thereof on the vertical axis and the percentage (%) on the horizontal axis (see FIG. 8), respectively.

Two solid lines in the figure represent classification lines derived by the same machine learning as above, and it was confirmed that if Nivolumab is hypothetically administered to the 21 patients with tumor plotted in the shaded area on the upper right side of the figure, separated by the classification lines, 17 thereamong (efficacy rate: 81.0%) would be expected to benefit therefrom.

Example 9: Verification of the Biomarker for
Determining the Efficacy of Nivolumab, Based on
the Respective MFIs of PD-1 Expressions in
Foxp3$^+$ T Cells and CD8$^+$ T Cells (Biomarker 9)

The respective MFIs of PD-1 expressions in Foxp3$^+$ T cells and CD8$^+$ T cells derived from tumor tissues of patients with gastric cancer (29 cases) and patients with non-small cell lung cancer (18 cases), before administration of Nivolumab were measured by flow cytometry, and the value given by subtracting the MFI of PD-1 expression in the CD8$^+$ T cells from the MFI of PD-1 expression in the Foxp3$^+$ T cells were calculated.

Among the above patients to which Nivolumab was administered according to the prescribed prescription, the Responder group (12 patients which were diagnosed as CR or PR) and Non-Responder group (35 patients which were diagnosed as SD or PD) were plotted on a graph based on the value of each patient thereof (see FIG. 10), respectively.

A dotted solid line in the figure represent a classification line derived by ROC analysis, and it was confirmed that if Nivolumab is hypothetically administered to the 13 patients with tumor having a value less than or equal to that indicated by the classification line (−208) (sensitivity=0.833; specificity=0.914 in ROC analysis), 10 thereamong (efficacy rate: 76.9%) would be expected to benefit therefrom.

Example 10: Verification of the Biomarker for Determining the Efficacy of Nivolumab, Based on the Respective MFIs of PD-1 Expressions in Treg Cells (Fr.II) and CD8$^+$ T Cells (Biomarker 10)

The respective MFIs of PD-1 expressions in Treg cells (Fr.II) and CD8$^+$ T cells derived from tumor tissues of patients with gastric cancer (29 cases) and patients with non-small cell lung cancer (18 cases), before administration of Nivolumab were measured by flow cytometry, and the value given by subtracting the MFI of PD-1 expression in the CD8$^+$ T cells from the MFI of PD-1 expression in the Treg cells (Fr.II) were calculated.

Among the above patients to which Nivolumab was administered according to the prescribed prescription, the Responder group (12 patients which were diagnosed as CR or PR) and Non-Responder group (35 patients which were diagnosed as SD or PD) were plotted on a graph based on the value of each patient thereof (see FIG. 10), respectively.

A dotted solid line in the figure represent a classification line derived by ROC analysis, and it was confirmed that if Nivolumab is hypothetically administered to the 12 patients with tumor having a value less than or equal to that indicated by the classification line (−131) (sensitivity=0.833; specificity=0.943 in ROC analysis), 10 thereamong (efficacy rate: 83.3%) would be expected to benefit therefrom.

INDUSTRIAL APPLICABILITY

By analyzing the combination of the two specific sets of evaluation items and the specific conditions defined by each combination of the two sets, it is possible to identify a patient with malignant tumor which can be expected to benefit more from an immune checkpoint inhibitor.

The invention claimed is:

1. A method for suppressing a progression of, suppressing a recurrence of and/or treating a malignant tumor, said method comprising:

(I) identifying a patient having any one of the conditions selected from the following items (a) to (c), wherein:

(a) is condition (a1) represented by formula:

$$Y_1 \geq a_{1\text{-}1} \times X_1 + Y_{1\text{-}1}$$

wherein $Y_1$ represents a percentage (%) of CCR7 expressing cells among CD8$^+$ T cells in a tumor tissue or blood from the patient with the malignant tumor prior to administration of an immune checkpoint inhibitor, $a_{1\text{-}1}$ represents about −637, $X_1$ represents a square root of a ratio of mean fluorescence intensity (MFI) of PD-1 expression in the CD8$^+$ T cells to MFI of PD-1 expression in Foxp3$^+$ T cells in the tumor tissue or blood from said patient, and $Y_{1\text{-}1}$ represents an arbitrary value from about 784 to about 914, or condition (a2) represented by two formulas:

$$Y_1 \leq a_{1\text{-}2} \times X_1 + Y_{1\text{-}2} \text{ and } Y_1 \leq a_{1\text{-}3} \times X_1 + Y_{1\text{-}3},$$

wherein $Y_1$ represents a percentage (%) of CCR7 expressing cells among the CD8$^+$ T cells in the tumor tissue or blood from said patient, $a_{1\text{-}2}$ represents about −24.0, $X_1$ represents a square root of a ratio of MFI of PD-1 expression in the CD8$^+$ T cells to MFI of PD-1 expression in the Foxp3$^+$ T cells in the tumor tissue or blood from said patient, Y 1-2 represents an arbitrary value from about 39.0 to about 50.9, $a_{1\text{-}3}$ represents about 666, and $Y_{1\text{-}3}$ represents an arbitrary value from about −652 to about −522;

(b) is condition (b1) represented by formula:

$$\text{Log}_{10}(Y_3+1) \geq a_{3\text{-}1} \times X_3 + Y_{3\text{-}1} \quad \text{or} \quad \text{Log}_{10}(Y_3) \geq a_{3\text{-}1} \times X_3 + Y_{3\text{-}1},$$

wherein $Y_3$ represents a number of PD-1 expressing cells among the CD8$^+$ T cells in the tumor tissue or blood from said patient, $a_{3\text{-}1}$ represents about −1.59, $X_3$ represents the square root of the ratio of MFI of PD-1 expression in the CD8$^+$ T cells to MFI of PD-1 expression in the Foxp3$^+$ T cells in the tumor tissue or blood from of said patient, and $Y_{3\text{-}1}$ represents an arbitrary value from about 4.09 to about 4.89, or condition (b2) represented by formula:

$$\text{Log}_{10}(Y_3+1) \geq a_{3\text{-}2} \times X_3 + Y_{3\text{-}2} \quad \text{or} \quad \text{Log}_{10}(Y_3) \geq a_{3\text{-}2} \times X_3 + Y_{3\text{-}2},$$

wherein $Y_3$ represents a number of PD-1 expressing cells among the CD8$^+$ T cells in the tumor tissue or blood from said patient, $a_{3\text{-}2}$ represents about −9.05, $X_3$ represents the square root of the ratio of MFI of PD-1 expression in the CD8$^+$ T cells to MFI of PD-1 expression in the Foxp3$^+$ T cells in the tumor tissue or blood from said patient, and $Y_{3\text{-}2}$ represents an arbitrary value from about 10.7 to about 13.3; and (c) the condition is represented by formula:

$$a_{8\text{-}1} \times X_8 + Y_{8\text{-}1} \leq Y_8 \leq a_{8\text{-}2} \times X_8 + Y_{8\text{-}2},$$

wherein $Y_8$ represents a square root of a ratio of MFI of PD-1 expression in CD3$^+$ cells to MFI of PD-1 expression in Fraction II Treg cells in the tumor tissue or blood from said patient, $a_{8\text{-}1}$ represents about −0.00338, $X_8$ represents a percentage (%) of PD-1 expressing cells among CD4$^+$ T cells in the tumor tissue or blood from said patient, $Y_{8\text{-}1}$ represents an arbitrary value from about 0.939 to about 1.37, $a_{8\text{-}2}$ represents about 0.270, and $Y_{8\text{-}2}$ represents an arbitrary value from about −6.98 to about −0.654; and (II) administering an effective dose of the immune checkpoint inhibitor to the patient identified in (I).

2. The method according to claim 1, wherein in (a) $Y_{1\text{-}1}$ represents 853, $Y_{1\text{-}2}$ represents 44.6, and $Y_{1\text{-}3}$ represents −591, in (b) $Y_{3\text{-}1}$ represents 4.42 and $Y_{3\text{-}2}$ represents 11.7, and in (c) $Y_{8\text{-}1}$ represents 1.17 and $Y_{8\text{-}2}$ represents −4.10.

3. A method for suppressing a progression of, suppressing a recurrence of and/or treating a malignant tumor, said method comprising:

(I) identifying a patient having a following condition:

in a tumor tissue or blood from said patient prior to administration of an immune checkpoint inhibitor a combination of items (1) and (2) below:

(1) any one selected from items (i) to (v):

(i) a percentage (%) of PD-1 expressing cells among Fraction III Treg cells, (ii) a percentage (%) of PD-1 expressing cells among Foxp3$^+$ T cells, (iii) a percentage (%) of PD-1 expressing cells among Fraction II Treg cells, (iv) a square root of a ratio of MFI of PD-1 expression in CD8$^+$ T cells to MFI of PD-1 expression in the Foxp3$^+$ T cells, and (v) a percentage (%) of PD-1 expressing cells among CD4$^+$ T cells; and (2) a percentage (%) of PD-1 expressing cells among the CD8$^+$ T cells, meets conditions selected from items (a) to (e), corresponding to items (i) to (v), respectively:

(a) condition represented by formula:

$$Y_2 \geq a_{2\text{-}1} \times X_2 + Y_{2\text{-}1},$$

wherein $Y_2$ represents the percentage (%) of item (i), $a_{2\text{-}1}$ represents about 0.765, $X_2$ represents the percentage (%) of item (2), and $Y_{2\text{-}1}$ represents an arbitrary value from about 50.6 to about 59.2, or formula:

$$Y_2 \leq a_{2\text{-}2} \times X_2 + Y_{2\text{-}2},$$

wherein $Y_2$ represents the percentage (%) of item (i), $a_{2\text{-}2}$ represents about 1.56, $X_2$ represents the percentage (%) of item (2), and $Y_{2\text{-}2}$ represents an arbitrary value from about −44.1 to about 14.5;

(b) condition represented by formula:

$$Y_5 \geq a_5 \times X_5 + Y_{5\text{-}1},$$

wherein $Y_5$ represents the percentage (%) of item (ii), as represents about 2.34, $X_5$ represents the percentage (%) of item (2), and $Y_{5\text{-}1}$ represents an arbitrary value from about −117 to about 131;

(c) condition represented by formula:

$$Y_6 \geq a_{6\text{-}1} \times X_6 + Y_{6\text{-}1},$$

wherein $Y_6$ represents the percentage (%) of item (iii), $a_{6\text{-}1}$ represents about 1.69, $X_6$ represents the percentage (%) of item (2), and $Y_{6\text{-}1}$ represents an arbitrary value from about 21.4 to about 44.1, or formula:

$$Y_6 \leq a_{6\text{-}2} \times X_6 + Y_{6\text{-}2},$$

wherein $Y_6$ represents the percentage (%) of item (iii), $a_{6\text{-}2}$ represents about 1.78, $X_6$ represents the percentage (%) of item (2), and $Y_{6\text{-}2}$ represents an arbitrary value from about −80.6 to about −21.0;

(d) condition represented by formula:

$$Y_4 \geq a_{4\text{-}1} \times X_4 + Y_{4\text{-}1},$$

wherein $Y_4$ represents a square root of item (iv), $a_{4\text{-}1}$ represents about −0.00273, $X_4$ represents the percentage (%) of item (2), and $Y_{4\text{-}1}$ represents an arbitrary value from about 0.905 to about 1.46, or formula:

$$Y_4 \geq a_{1\text{-}2} \times X_4 + Y_{4\text{-}2},$$

wherein $Y_4$ represents the square root of item (iv), $a_{4\text{-}2}$ represents about −0.0294, $X_4$ represents the percentage (%) of item (2), and $Y_{4\text{-}2}$ represents an arbitrary value from about 2.18 to about 3.31; and (e) condition represented by formula:

$$Y_7 \leq a_{7\text{-}1} \times X_7 + Y_{7\text{-}1},$$

wherein $Y_7$ represents the percentage (%) of item (v), $a_{7\text{-}1}$ represents about 0.227, $X_7$ represents the percentage (%) of item (2), and $Y_{7\text{-}1}$ represents an arbitrary value from about −13.9 to about 4.03, or formula:

$$Y_7 \leq a_{7\text{-}2} \times X_7 + Y_{7\text{-}2},$$

wherein $Y_7$ represents the percentage (%) of item (v), $a_{7\text{-}2}$ represents about 3.32, $X_7$ represents the percentage (%) of item (2), and $Y_{7\text{-}2}$ represents an arbitrary value from about −199 to about 58.2; and (II) administering an effective dose of the immune checkpoint inhibitor to the patient identified in (I).

4. The method according to claim 3, wherein in (a) $Y_{2\text{-}1}$ represents 54.1 and $Y_{2\text{-}2}$ represents −26.6, in (b) $Y_{5\text{-}1}$ represents −54.4, in (c) $Y_{6\text{-}1}$ represents 31.8 and $Y_{6\text{-}2}$ represents −48.2, in (d) $Y_{4\text{-}1}$ represents 1.18 and $Y_{4\text{-}2}$ represents 2.74, and in (e) $Y_{7\text{-}1}$ represents −6.56 and $Y_{7\text{-}2}$ represents −93.5.

5. The method according to claim 3, wherein an active ingredient of the immune checkpoint inhibitor is an anti-PD-1 antibody, anti-PD-L1 antibody, PD-1 antagonist, PD-L1/VISTA antagonist, PD-L1/TIM3 antagonist, anti-PD-L2 antibody, PD-L1 fusion protein, PD-L2 fusion protein, anti-CTLA-4 antibody, anti-LAG-3 antibody, LAG-3 fusion protein, anti-Tim3 antibody, anti-KIR antibody, anti-BTLA antibody, anti-TIGIT antibody, anti-VISTA antibody, anti-CSF-1R antibody or CSF-1R inhibitor.

6. The method according to claim 5, wherein the anti-PD-1 antibody is Nivolumab, Cemiplimab, Pembrolizumab, Spartalizumab, Tislelizumab, Dostarlimab, Toripalimab, Camrelizumab, Genolimzumab, Sintilimab, Lodapolimab, Retifanlimab, Balstilimab, Serplulimab, Budigalimab, Prolgolimab, Sasanlimab, Cetrelimab, Zimberelimab, Penpulimab, AMP-514, STI-A1110, ENUM 388D4, ENUM 244C8, GLS010, CS1003, BAT-1306, AK103, BI 754091, LZM009, CMAB819, Sym021, SSI-361, JY034, HX008, ISU106 or CX-188.

7. The method according to claim 5, wherein the anti-PD-L1 antibody is Atezolizumab, Avelumab, Durvalumab, Manelimab, Pacmilimab, Envafolimab, Cosibelimab, BMS-936559, STI-1014, HLX20, SHR-1316, CS1001, MSB2311, BGB-A333, KL-A167, AK106, AK104, ZKAB001, FAZ053, CBT-502 or JS003.

8. The method according to claim 5, wherein the anti-CTLA-4 antibody is Ipilimumab, Zalifrelimab, Nurulimab or Tremelimumab.

9. The method according to claim 5, wherein the malignant tumor is a solid cancer or a hematological cancer.

10. The method according to claim 9, wherein the solid cancer is one or more cancers selected from malignant melanoma, non-small cell lung cancer, small cell lung cancer, head and neck cancer, renal cell carcinoma, clear cell renal cell carcinoma, breast cancer, ovarian cancer, serous ovarian cancer, ovarian clear cell adenocarcinomas, nasopharyngeal cancer, uterine cancer, anal cancer, colorectal cancer, rectum cancer, colon cancer, hepatocellular carcinoma, esophageal cancer, esophageal adenocarcinoma, gastric cancer, esophagogastric junction cancer, small intestine cancer, pancreatic cancer, urothelial cancer, prostate cancer, fallopian tube cancer, primary peritoneal cancer, malignant pleural mesothelioma, gallbladder cancer, bile duct cancer, biliary tract cancer, skin cancer, testicular cancer, vaginal cancer, vulvar cancer, penile cancer, endocrine cancer, thyroid cancer, parathyroid cancer, adrenal cancer, spinal tumor, brain tumor, squamous cell carcinoma, bone/soft tissue sarcomas and Kaposi's sarcoma.

11. The method according to claim 3, wherein the patient with a malignant tumor has no history of treatment with other anti-neoplastic drugs.

12. The method according to claim 3, wherein a percentage (%) of PD-L1 expressing tumor cells among tumor cells in the malignant tumor tissue (TPS) or a total percentage (%) of PD-L1 positive tumor cells, lymphocytes and macrophages among tumor cells in the malignant tumor tissue (CPS) is less than 50%.

13. The method according to claim 3, wherein the malignant tumor is a malignant tumor without high-frequency microsatellite instability (MSI-H) and/or deficient mismatch repair (dMMR).

14. The method according to claim 3, wherein a tumor mutation burden (TMB) of the malignant tumor is low frequency.

* * * * *